US009128094B2

(12) United States Patent
Cheng

(10) Patent No.: US 9,128,094 B2
(45) Date of Patent: *Sep. 8, 2015

(54) HIGH THROUGHPUT CELL-BASED HPV IMMUNOASSAYS FOR DIAGNOSIS AND SCREENING OF HPV-ASSOCIATED CANCERS

(75) Inventor: Shuling Cheng, Fremont, CA (US)

(73) Assignee: OncoHealth Corp., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/520,021

(22) PCT Filed: Dec. 16, 2010

(86) PCT No.: PCT/US2010/060765
§ 371 (c)(1),
(2), (4) Date: Jun. 29, 2012

(87) PCT Pub. No.: WO2011/084598
PCT Pub. Date: Jul. 14, 2011

(65) Prior Publication Data
US 2012/0282595 A1  Nov. 8, 2012

Related U.S. Application Data

(60) Provisional application No. 61/335,540, filed on Jan. 8, 2010.

(51) Int. Cl.
  *C12Q 1/70*   (2006.01)
  *G01N 33/53*   (2006.01)
  *G01N 33/574*   (2006.01)
  *G01N 33/569*   (2006.01)

(52) U.S. Cl.
  CPC .... *G01N 33/57411* (2013.01); *G01N 33/56983* (2013.01); *G01N 2333/025* (2013.01)

(58) Field of Classification Search
  CPC .................. C07K 2317/33; G01N 33/56983; G01N 33/571; G01N 2333/025; G01N 2369/10
  See application file for complete search history.

(56) References Cited

U.S. PATENT DOCUMENTS

| | | |
|---|---|---|
| 3,633,999 A | 1/1972 | Buckles |
| 4,511,220 A | 4/1985 | Scully |
| 4,619,508 A | 10/1986 | Shibuya et al. |
| 4,744,615 A | 5/1988 | Fan et al. |
| 4,851,978 A | 7/1989 | Ichihara |
| 5,045,447 A | 9/1991 | Minson |
| 5,057,411 A | 10/1991 | Lancasater et al. |
| 5,061,025 A | 10/1991 | Debesis |
| 5,109,465 A | 4/1992 | Klopotek |
| 5,183,755 A | 2/1993 | Ohmoto et al. |
| 5,224,200 A | 6/1993 | Rasmussen et al. |
| 5,233,460 A | 8/1993 | Partlo et al. |
| 5,307,207 A | 4/1994 | Ichihara |
| 5,315,427 A | 5/1994 | Rauch et al. |
| 5,328,785 A | 7/1994 | Smith et al. |
| 5,357,365 A | 10/1994 | Ipposhi et al. |
| 5,401,627 A | 3/1995 | Dillner et al. |
| 5,415,995 A | 5/1995 | Schoolnik et al. |
| 5,453,814 A | 9/1995 | Aiyer |
| 5,561,081 A | 10/1996 | Takenouchi et al. |
| 5,591,574 A | 1/1997 | Orth et al. |
| 5,610,733 A | 3/1997 | Feldman et al. |
| 5,621,529 A | 4/1997 | Gordon et al. |
| 5,629,161 A | 5/1997 | Muller et al. |
| 5,662,410 A | 9/1997 | Suganuma |
| 5,665,535 A | 9/1997 | Orth et al. |
| 5,679,509 A | 10/1997 | Wheeler et al. |
| 5,695,770 A | 12/1997 | Raychaudhuri et al. |
| 5,699,191 A | 12/1997 | Fork |
| 5,754,278 A | 5/1998 | Kurtz |
| 5,876,723 A | 3/1999 | Cole et al. |
| 5,888,888 A | 3/1999 | Talwar et al. |
| 5,914,389 A | 6/1999 | Huibregtse et al. |

(Continued)

FOREIGN PATENT DOCUMENTS

| | | |
|---|---|---|
| CN | 1675550 | 9/2005 |
| CN | 03825051.9 | 11/2005 |

(Continued)

OTHER PUBLICATIONS

Kashmiri et al. SDR grafting—a new approach to antibody humanization. Methods 2005, vol. 36, Issue 1, pp. 25-34.*
Tamura et al. Structural Correlates of an Anticarcinoma Antibody: Identification of Specifically-Determining Residues (SDRs) and Development of a Minimally Immunogenic Antibody Variant by Retention of SDRs only. The Journal of Immunology 2000, vol. 164, Issue 3, pp. 1432-1441.*
Greenspan et al. Defining epitopes: Its not as easy as it seems. Nature Biotechnology 1999, vol. 17, pp. 936-937.*
Wu et al. Analysis of mutations in the E6/E7 oncogenes and L1 gene of human papillomavirus 16 cervical cancer isolates from China. Journal of General Virology 2006, vol. 87, pp. 1181-1188.*

(Continued)

*Primary Examiner* — Louise W Humphrey
(74) *Attorney, Agent, or Firm* — Yi-Shan Yang; Fenwick & West LLP

(57) ABSTRACT

Methods for quantifying an HPV protein expression in a clinical sample are disclosed. The quantifying methods include the process for obtaining the clinical sample. Such a clinical sample is consisted of a population of cells that are susceptible to infection by an HPV. The quantifying methods also include the process for depositing the clinical sample into a container. The clinical sample is contacted with the first antibody that specifically binds to an HPV protein which is expressed by an HPV-infected cell under a condition that promotes specific binding of the first antibody to the HPV protein expressed by the population of cells. The methods further include the process for quantifying the specific binding of the first antibody and thereby quantifying the HPV protein expression in the clinical sample. The assay provides an objective test to identify patients with high-grade precursor from cytology samples before biopsy.

23 Claims, 23 Drawing Sheets

(56) References Cited

U.S. PATENT DOCUMENTS

| | | | |
|---|---|---|---|
| 6,013,262 A | 1/2000 | Frazer et al. | |
| 6,228,578 B1 | 5/2001 | Impraim et al. | |
| 6,329,167 B1 | 12/2001 | Patterson | |
| 6,355,424 B1 | 3/2002 | Lorincz et al. | |
| 6,420,106 B1 | 7/2002 | Gyllensten et al. | |
| 6,489,105 B1 | 12/2002 | Matlashewski et al. | |
| 6,524,825 B1 | 2/2003 | Mizzen et al. | |
| 6,528,278 B2 | 3/2003 | Patterson et al. | |
| 6,709,832 B1 | 3/2004 | Von Knebel Doeberitz et al. | |
| 6,743,593 B2 | 6/2004 | Hu | |
| 6,827,933 B2 | 12/2004 | Orth et al. | |
| 6,884,786 B1 | 4/2005 | Kieny et al. | |
| 6,890,514 B2 | 5/2005 | Mathur et al. | |
| 6,900,035 B2 | 5/2005 | Mizzen et al. | |
| 6,933,123 B2 | 8/2005 | Hu et al. | |
| 6,939,687 B2 | 9/2005 | Patterson | |
| 7,001,995 B1 | 2/2006 | Neeper et al. | |
| 7,078,061 B2 | 7/2006 | Debad et al. | |
| 7,157,233 B2 | 1/2007 | Fischer et al. | |
| 7,361,460 B2 | 4/2008 | Williams et al. | |
| 7,399,467 B2 | 7/2008 | Lu et al. | |
| 7,455,973 B2 | 11/2008 | Fischer et al. | |
| 7,501,261 B2 | 3/2009 | Meijer et al. | |
| 7,510,838 B2 | 3/2009 | Fischer et al. | |
| 7,838,215 B2 | 11/2010 | Gombrich et al. | |
| 7,888,032 B2 | 2/2011 | Patterson | |
| 2001/0034021 A1 | 10/2001 | Muller et al. | |
| 2003/0044870 A1 | 3/2003 | Sehr et al. | |
| 2003/0190602 A1 | 10/2003 | Pressman et al. | |
| 2004/0018487 A1* | 1/2004 | Lu et al. | 435/5 |
| 2004/0170644 A1 | 9/2004 | Mailere et al. | |
| 2004/0175695 A1 | 9/2004 | Debad et al. | |
| 2004/0260157 A1 | 12/2004 | Montes et al. | |
| 2005/0037017 A1 | 2/2005 | Mizzen et al. | |
| 2005/0037342 A1 | 2/2005 | Mathur et al. | |
| 2005/0042600 A1 | 2/2005 | Hu et al. | |
| 2005/0142541 A1* | 6/2005 | Lu et al. | 435/5 |
| 2005/0147621 A1 | 7/2005 | Higgins et al. | |
| 2005/0159386 A1 | 7/2005 | Kieny et al. | |
| 2005/0255460 A1 | 11/2005 | Lu et al. | |
| 2005/0255468 A1 | 11/2005 | Ridder et al. | |
| 2005/0260566 A1 | 11/2005 | Fischer et al. | |
| 2006/0029943 A1 | 2/2006 | Hermonat et al. | |
| 2006/0039919 A1 | 2/2006 | Chang et al. | |
| 2006/0121516 A1 | 6/2006 | Norman et al. | |
| 2006/0147906 A1 | 7/2006 | Zwerschke et al. | |
| 2006/0153864 A1 | 7/2006 | Gissmann et al. | |
| 2006/0154238 A1 | 7/2006 | Hu et al. | |
| 2006/0160069 A1 | 7/2006 | Chau et al. | |
| 2006/0172285 A1 | 8/2006 | Patterson | |
| 2006/0269967 A1 | 11/2006 | Chen et al. | |
| 2006/0286595 A1 | 12/2006 | Fischer et al. | |
| 2007/0065810 A1 | 3/2007 | Schlegel et al. | |
| 2007/0099199 A1 | 5/2007 | Lu et al. | |
| 2007/0117167 A1 | 5/2007 | Malinowski et al. | |
| 2007/0166699 A1 | 7/2007 | Zwerschke et al. | |
| 2007/0190529 A1 | 8/2007 | Ridder et al. | |
| 2008/0038738 A1 | 2/2008 | Weigum et al. | |
| 2008/0267982 A1 | 10/2008 | Kiselev et al. | |
| 2009/0047660 A1 | 2/2009 | Lu et al. | |
| 2009/0075377 A1 | 3/2009 | Lu et al. | |
| 2009/0104597 A1 | 4/2009 | Gombrich et al. | |
| 2009/0148864 A1 | 6/2009 | Fischer et al. | |

FOREIGN PATENT DOCUMENTS

| | | |
|---|---|---|
| EP | 0256321 | 2/1988 |
| GB | 2379220 | 5/2003 |
| JP | 2002296274 | 10/2002 |
| JP | 2007503208 | 2/2007 |
| JP | 2007537705 | 12/2007 |
| TW | 95142312 | 11/2006 |
| TW | 100100781 | 1/2010 |
| TW | 201012932 | 4/2010 |
| TW | 201043958 | 12/2010 |
| WO | W9700888 | 1/1997 |
| WO | WO9910375 | 3/1999 |
| WO | WO0204007 A2 | 1/2002 |
| WO | WO2004085683 | 10/2004 |
| WO | WO2005008248 | 1/2005 |
| WO | 2005063286 | 7/2005 |
| WO | W02005/063286 | 7/2005 |
| WO | WO2005088311 | 9/2005 |
| WO | WO2006083984 | 8/2006 |
| WO | WO2007059492 | 5/2007 |
| WO | WO2007095320 | 8/2007 |
| WO | WO2009042488 | 4/2009 |
| WO | 2009079192 | 6/2009 |
| WO | WO2009151632 | 12/2009 |
| WO | WO2009151633 | 12/2009 |
| WO | WO2010129821 | 11/2010 |
| WO | WO2011084598 | 7/2011 |

OTHER PUBLICATIONS

Caceres-Cortes et al. Implication of Tyrosine Kinase Receptor and Steel Factor in Cell Density-dependent Growth in Cervical Cancers and Leukemia. Cancer Research 2001, vol. 61, pp. 6281-6289.*

Non-final Office Action for U.S. Appl. No. 12/456,054 dated Sep. 25, 2012.

Final Office Action for U.S. Appl. No. 12/456,053 dated Sep. 24, 2012.

JH Joen et al., "Immunocytochemical detection of HPV16E7 in cervical smear." 2007. Experimental and Molecular Medicine, vol. 39, No. 5, 621-628.

C Liang et al., "Biomarkers of HPV in Head and Neck Squamous Cell Carcinoma." 2012, Cancer Research. Published online Sep. 18, 2012.

D Holzinger et al., "Viral RNA Patterns and High Viral Load Realiably Define Oropharynx Carcinomas wit hActive HPV16 Involvement." 2012, Cancer Research. Published online Sep. 18, 2012.

AG Ostor et al., "Natural History of Cervical Intraepithelial Neoplasia: A Critical Review." 1993 International Journal of Gyncological Pathology. 12:186-192.

J Melnikow et al., 1998. "Natural history of Cervical Squamous Intraepithelial Lesions: A meta-Analysis." 1998 vol. 92, No. 4, pp. 727-735.

European Patent Office Communication dated Dec. 3, 2012 for Application No. 09762929.9, PCT/US2009003538.

Oltersdorf et al., 1987. "Identification of Human Papillomavirus Type 16 E7 Protein by Monoclonal Antibodies." J. Gen. Virol. 68, 2933-2938.

Jochmus et al., 1999. "Chimeric Virus-like Partiles of the Human Papillomavirus Type 16 (HPV 16) as a Prophylactic and Therapeutic Vaccine." Archives of Medical Research. 30, 269-274.

HyTest News. Mar. 2008, pp. 1-8. Advanced ImmunoChemical, Finland.

Mattil-Fritz et al., 2008. "Immunotherapy of equine sarcoid: dose-escalation trial for the use of chimeric papullomavirus-like particles." Journal of General Virology 89, 138-147.

Rizk et al., 2008. "Reactivity pattern of 92 monoclonal antibodies with 15 human papillomavirus types." Journal of General Virology, 89, 117-129.

Non-final Office action for U.S. Appl. No. 12/456,053 dated Apr. 6, 2012.

Final Office action for U.S. Appl. No. 12/456,054 dated Apr. 16, 2012.

European Patent Office Communication dated Jun. 6, 2013 for Application No. 10842601.6.

European Patent Office Communication dated Jul. 18, 2013 for Application No. 10772861.0.

Non-final Office action dated Jul. 3, 2013 for U.S. Appl. No. 12/456,055.

Santer et al., 2007 Carcinogenesis, vol. 28 No. 12 pp. 2511-2520. "Human papillomavirus type 16 E7 oncoprotein inhibits apoptosis mediated by nuclear insulin-like growth factor-binding protein-3 by enhancing its ubiquitin/proteasome-dependent degradation."

Non-final Office action dated Jul. 11, 2013 for U.S. Appl. No. 13/585,509.

(56) References Cited

OTHER PUBLICATIONS

China Patent Office Communication dated Jul. 19, 2013 for Application No. 201080020175.9.
Taiwan Patent Office Communication dated Aug. 22, 2013 for Application No. 100100781.
Zhao et al., 2013 Cancer Prevention Research. Published OnlineFirst Jul. 22, 2013. "An Evaluation of Novel, Lower-Cost Molecular Screening Test for Human Papillomavirus in Rural China."
Shi et al., 2009 American Journal of Epidemiology vol. 170 No. 6. 708-716. "Human papillomavirus testing for cervical cancer screening: results from a 6-year prospective study in rural China."
Belinson et al., Am J. Clin Pathol 2011; 135:790-795. "A population-based clinical trial comparing endocervical high-risk HPV testing using hybrid capture 2 and Cervista from the SHENCAST II study."
Dockter et al., 2009 Journal of Clinical Viroogy 45, 51: 539-547. "Analytical characterization of the APTIMA HPV assay."
Wong et al., 2011 Journal of Clinical Virology 51 (2011) 136-138. "Efficacy of Abbott real time high risk HPV test in evaluation of atypical squamous cells of undetermined significance from and Asian screening population."
Branca et al., 2005 Am J Clin Pathol 124: 113-121. "Survivin as a marker of cervical intraepithelial neoplasia and high-risk human papillomavirus and a predictor of virus clearance and prognosis in cervical cancer."
Branca et al., 2006 J Clin Pathol 59: 40-47. "Aberrant expression of VEFG-C is related to grade of cervical intraepithelial neoplasia (CIN) and high risk HPV but does not predict virus clearance after treatment of CIN or prognosis of cervical cancer."
Lambert et al., 2006 Experimental and Molecular Pathology 80: 192-196. "p16INK4A expression in cervical premalignant and malignant lesion."
Giannoudis et al., 2000 British J. Cancer 81:424-7. "Differential expression of p53 and p21 in low grade cervical squamous intraepithelial lesions infected with low, intermediate, and high risk human papillomaviruses."
Saqi et al., 2002 "Overexpression of p16INK4A in liquid-based specimens (SurePath) as marker of cervical dysplasia and neoplasia." 27: 365-370.
Park et al., 1998 "HPV-16-releated proteins as the serologic markers in cervical neoplasis." Gynecologic oncology 69, 47-55.
Lie et al., 1999 Int J Gynecol Pathol 18(1): 5-11."Expression of p53, MDM2, and p21 proteins in high-grade cervical intraepithelial neoplasia and relationship to human papillomavirus infection."
Arbyn et al., 2009. J Cell Mol Med. vol. 13 No. 4 648-659. "Triage of women with equivocal or low-grade cervical cytology results: a meta-analysis of the HPV test positivity rate".
Andersson et al., 2006. International Journal of Oncology 29: 705-711. "Expression of E6/E7 mRNA from 'high risk' human papillomavirus in relation to CIN grade, viral load and p16INK4a".
Balasubramanian et al., Cancer Epidemiol Biomarkers Prey 2009;18:3008-3017. "Evaluation of an ELISA for p16INK4a as a Screening Test for Cervical Cancer".
Cardenas-Turanzas et al., Gyn Oncology 107 (2007) S138-S146. "The clinical effectiveness of optical spectroscopy for the in vivo diagnosis of cervical intraepithelial neoplasia: Where are we?".
Castle et al., 2010. AACCP. Benefits and risks of HPV testing in cervical cancer screening See Online/Articles DOI:10.1016/S1470-2045(09)70360-2.
Castle et al., American Journal of Obstetrics & Gynecology Oct. 2007 "Risk assessment to guide the prevention of cervical cancer".
Choi et al., Biosensors and Bioelectronics 20 (2005) 2236-2243. "Adenoviral p53 effects and cell-specific E7 protein-protein interactions of human cervical cancer cells".
Cole et al., Journal of Virology, Jun. 1986, vol. 58. No. 3. p. 991-995. "Genome Organization and Nucleotide Sequence of Human Papillomavirus Type 33, Which Is Associated with Cervical Cancer".
Cole et al., J. Mol. Biol. (1987) 193, 599-608. "Nucleotide Sequence and Comparative Analysis of the Human Papillomavirus Type 18 Genome Phylogeny of Papillomaviruses and Repeated Structure of the E6 and E7 Gene Products".

Sawaya 2008 Annals of Internal Medicine vol. 148 • No. 7 p557 "Adding Human Papillomavirus Testing to Cytology for Primary Cervical Cancer Screening: Shooting First and Asking Questions Later".
Fuchs et al., Journal of Virology, May 1986, p. 626-634. vol. 58, No. 2 "Epidermodysplasia Verruciformis-Associated Human Papillomavirus 8: Genomic Sequence and Comparative Analysis".
Garcia-Alai et al., Biochemistry 2007, 46, "High-Risk HPV E6 Oncoproteins Assemble into Large Oligomers that Allow Localization of Endogenous Species in Prototypic HPV-Transformed Cell Lines".
Kulasingam et al., Obstetrics & Gynecology vol. 107, No. 2, Part 1, February 2006 Cost-effectiveness of Extending Cervical Cancer Screening Intervals Among Women With Prior Normal Pap Tests.
Mao et al., Int. J. Cancer: 120, 2435-2438 (2007) "Evaluation of a new p16INK4a ELISA test and a high-risk HPV DNA test for cervical cancer screening: Results from proof-of-concept study".
Molden et al., Int. J. Cancer: 114, 973-976 (2005) "Predicting CIN2 when detecting HPV mRNA and DNA by PreTect HPV-Proofer and consensus PCR: a 2-year follow-up of women with ASCUS or LSIL Pap smear".
Marimatsu et al., Am J Clin Pathol 2005;123:716-723 "High-Throughput Cervical Cancer Screening Using Intracellular Human Papillomavirus E6 and E7 mRNA Quantification by Flow Cytometry".
NCCN Clinical Practice Guidelines in Oncology™ v.2. 2007 Cervical Cancer Screening.
Negri et al., Am J Surg Pathol 2008;32:1715-1720 "p16ink4a and HPV L1 Immunohistochemistry is Helpful for Estimating the Behavior of Low-grade Dysplastic Lesions of the Cervix Uteri".
Norchip et a;., 22nd. International Papillomavirus Conference, Vancouver, BC, Canada, Apr. 30-May 6, 2005 "Persistent transforming HPV infection may correlate with persistent histologically defined CIN II+ Summary of studies by Frank Karlsen and Hanne Skomedal".
Trope et al., Journal of Clinical Microbiology, Aug. 2009, p. 2458-2464. "Performance of Human Papillomavirus DNA and mRNA Testing Strategies for Women with and without Cervical Neoplasia".
Schiffman et al., Arch Pathol Lab Med—vol. 127, Aug. 2003. "Findings to Date From the ASCUS-LSIL Triage Study (ALTS)." pp. 946-949.
Woodman et al., "The natural history of cervical HPV infection: unresolved issues." Nature Review Cancer, vol. 7 | Jan. 2007 | 11.
Ronco et al., BMC Women's Health 2008, 8:23. "New paradigms in cervical cancer prevention: opportunities and risks">.
Talora et al., Genes Dev. 2002 16: 2252-2263. Specific down-modulation of Notch1 signaling in cervical cancer cells is required for sustained HPV-E6/E7 expression and late steps of malignant transformation.
Tungteakkhun wr al., Arch Virol (2008) 153:397-408. "Cellular binding partners of the human papillomavirus E6 protein".
Sellor et al., Journal of Lower Genital Tract Disease, vol. 15, No. 2, 2011, 169-176. Association of Elevated E6 Oncoprotein With Grade of Cervical Neoplasia Using PDZ InteractionYMediated Precipitation of E6.
Ronco et al., "Effi cacy of human papillomavirus testing for the detection of invasive cervical cancers and cervical intraepithelial neoplasia: a randomised controlled trial:." Published Online Jan. 19, 2010.
Schneider-Gadicke et al., The EMBO Journal vol. 5 No. 9 pp. 2285-2292, 1986. "Different human cervical carcinoma cell lines show similar transcription patterns of human papillomavirus type 18 early genes."
Wentzensen et al., Disease Markers 23 (2007) 315-330. "Biomarkers in cervical cancer screening."
Molder et a;., Cancer Epidemiology Biomarkers and Prevention. 2005, 14, p. 367. Comparison of Human Papillomavirus Messeger DNA and DNA detection: A crodd sectional study of 4136 wk e > 30 years of age with a 2, year fikkiw-up of high=grade squamous intraepitehlial Lesion.
Sawaya et al., 2005. www.nejm.org May 10, 2007. "HPV Vaccination—More Answers, More Questions."

(56) References Cited

OTHER PUBLICATIONS

Perez et al., 2009. 25th International Papillomavirus Conference, Sweden. "Detection of HPV E6/E7 Oncoporteins in Cervical Cancer."
Parkin et al., Int. J. Cancer: 80, 827-841 (1999). "Estimates of the Worldwide Incidence of 25 Major Cancers in 1990."
Schneider et al., 1991 Int. j. Gynecol Pathol. 10:1-14 "Prevalence of Human Papillomavirus Genomes in Tissue from the Lower Genital Tract as Detected by Molecular in situ hybridization."
Segnan et al., 1994 European Journal of Cancer vol. 30, 873-875. "Cervical cancer screening. Human benefits and human costs in the evaluation of screening programmes."
Partridge et al., 2008 J. National Compr. Cancer Network 6: 58-82. Abstract only.
Heck et al., 1992 Proc. Natl. Acad. Sci. USA vol. 89, pp. 4442-4446, May 1992. "Efficiency of binding the retinoblastoma protein correlates with the transforming capacity of the E7 oncoproteins of the human papillomaviruses."
Chellappan et al., 1992 Proc. Natl. Acad. Sci. USA vol. 89, pp. 4549-4553, May 1992. "Adenovirus EIA, simian virus 40 tumor antigen, and human papillomavirus E7 protein share the capacity to disrupt the interaction between transcription factor E2F and the retinoblastoma gene product."
Dyson et al., Science 1989. 243: 934-937. "The Human Papilloma Virus-16 E7 Oncoprotein Is Able to Bind to the Retinoblastoma Gene Product."
Zerfass et al., J. Virol. 1995, 69(10):6389. "Sequential activation of cyclin E and cyclin A gene expression by human papillomavirus type 16 E7 through sequences necessary for transformation."
Zerfass-Thome et al., 1996 Oncogene 13:2323-2330. "Inactivation of the cdk inhibitor p27KIP1 by the human papillomavirus type 16 E7 oncoprotein."
Saint, M., G. Gildengorin, and G. F. Sawaya. 2005. Current Cervical Neoplasia Screening Practices of Obstetriciaqn/ Gynecologists in the US. Am. J. Obstet. Gynecol. 192:414-421.
TIPO Search Report and Communication for Taiwan Invention Patent Application No. 095142312, Mar. 24, 2012. English search report on p. 1.
TIPO Search Report and Communication for Taiwan Invention Patent Application No. 098119611, Mar. 22, 2012. English search report on p. 1.
TIPO Search Report and Communication for Taiwan Invention Patent Application No. 098119612, Mar. 13, 2012. English search report on p. 1.
Volgareva et al., Protein p16 as a marker of dysplastic and neoplastic alterations in cervical epithelial cells. BMC Cancer 2004, 4:58. pp.
Liu et al., Preparation of monoclonal antibodies against human papillomavirus 16 E6 protein. Journal of Monoclonal Antibody, vol. 11 No. 3-4, Dec. 1995. English abstract on p. 3.
Su et al., Expression of human papillomavirus type 16 E6 oncogene production of monoclonal antibodies against HPV 16 E6 protein. Journal of Chinese Microbiology and Immunology, vol. 13 No. 3, 1993. English abstract on p. 4.
Wang et al., Expression of human papillomavirus type 16 L1 and construction of hybridoma cell strain of human papillomavirus type 16 L1 monoclonal antibody. Chin J. Endemiol, Jan. 20, 2007, vol. 26, No. 1. English abstract on p. 1.
EPO Communcation for Application No. 12164498.3 dated on Sep. 28, 2012.
MA Romanos et al., 1995. Production of a phosphorylated GST::HPV-6 E7 Fusion Protein Using a Yeast Expression Vector and Glutathione S-transferase Fusions. Gene. 152, 137-138.
Partial European Search Report for Application No. 12164498, dated Sep. 19, 2012.
T. Ristriani et al., 2001. "Specific Recognition of Four-way DNA Junctions by the C-terminal Zinc-binding Domain of HPV Oncoprotein E6." J. Mol. Biol. 305, 729-739.
KLMC Franken et al., 2000. "Purificaiton of His-Tagged PRoteins by Immobilized Chelate Affinity Chromatography: The Benefits from the Use of Organic Solvent." Protein Expression and Purification 18, 95-99.
Y. Nomine et al., 2001. "A strategy for optimizing the monodispersity of fusion proteins: application to purification of recombinant HPV E6 oncoprotein." Protein Engineering. 14, No. 4 pp. 297-305.
JA DeVoti et al., 2004. "Failure of Gamma Interferon but Not Interleukin-10 Expression in Response to Human Papillomavirus Type 11 E6 PRotein in Respiratory Papillomatosis." Clinical and Vaccine Immunology 11(3) 538-547.
TIPO Search Report and Communication for Taiwan Invention Patent Application No. 098119612, Oct. 5, 2012. Search Report Brief is on p. 1.
European Patent Office Communication dated Jan. 30, 2013 for Application No. 12164498.3-2402/2522756.
Non-final Office Action for U.S. Appl. No. 13/585,509 dated Jan. 15, 2013.
Qiao et al., 2008. "A New HPV-DNA Test for Cervical-Cancer Screening in Developing Regions: a Cross-Sectional Study of Clinical Accuracy in Rural China." Lancet Oncology 9: 929-936.
Zhao et al., 2010. "Performance of High-Risk Human Papillomavirus DNA Testing as a Primary Screening for Cervical Cancer: a Pooled Analysis of Individual Patient Data from 17 Population-Based Studies from China." Lancet Oncology 11: 1160-1171.
Zhao et al., 2011. "Pooled Analysis of a Self-Sampling HPV DNA Test as a Cervical Cancer Primary Screening Method." JNCI 104: 1-11.
Arbyn et al., 2010. "HPV-Based Cervical-Cancer Screening in China." World Health Organization GLOBOCAN 2008. Published online Nov. 12, 2010. http://globocan.iarcfr/.
Wong et al., 2011. "Efficacy of Abbott Real Time High Risk HPV Test in Evaluation of Atypical Squamous Cells of Undetermined Significance from an Asian Screening Population." Journal of Clinical Virology 51, 136-138.
Petignat et al., 2012. "Is It Time to Introduce HPV Seld-Sampling for Primary Cervical Cancer Screening?" Editorial, JNCI. 104 (3): pp. 1-2.
EPO Communication for App. No. 06846299.3, dated May 9, 2012.
Rocha-Zavaleta et al., 1997. British Journal of Cancer 75(8), 1144-1150. Differences in serological IgA responses to recombinant baculovirus-derived human papillomavirus E2 protein in the natural history of cervical neoplasia.
China Patent Office Communication dated Apr. 1, 2013 for Application No. 200980131078.4.
China Patent Office Communication dated Mar. 13, 2013 for Application No. 200980131077.X.
La Selvey et al., 1992 Journal of Virological Methods, 37, 119-128. "An ELISA capture assay for the E7 transforming proteins of HPV16 and HPV18."
H Griesser et al., 2004 Analyt Quant Cytol Histol 26, 241-245. "Correlation of Immunochemical Detection of HPV L1 capsid protein in Pap Smears with Regression of High-Risl HPV Positive Milk/ Moderate Dysplasia."
Advisory action for U.S. Appl. No. 12/456,055 dated Mar. 12, 2012.
Final Office action for U.S. Appl. No. 12/456,076 dated May 24, 2012.
Tindle RW et al., 1990 Journal of General Virology. 71, 1347-1354. "Identification of B epitopes in human papillomavirus type 16 E7 open reading frame protein."
Santa Cruz Biotechnology, Inc. Product Data Sheet for sc-18114 E6-AP (C-19). 2006.
Non-final Office Action for U.S. Appl. No. 12/590,747 dated Aug. 15, 2012.
http://www.biology-online.org/dictionary/Native_protein; Mar. 16, 2010.
SJ Lee et al., J Immunol (2001); 167; 497-504. "Both E6 and E7 Oncoproteins of Human Papillomavirus 16 Inhibit IL-IS-Induced IFN-'Y Production in Human Peripheral Blood Mononuclear and NK Cells."

(56) References Cited

OTHER PUBLICATIONS

S Vazquez-Vega et al., BMC Cancer (2007). 7(Suppl 1), A21. "Expression of viral and cellular cycle proteins and proteinases in cervical carcinoma cell lines as possible immunocytochemical markers of malignant phenotype."
J Doorbar, (2006) Clinical Science 1, 10, 525-541. "Molecular biology of human papillomavirus infection and cervical cancer."
M Fiedler et al., (2004) The FASEB Journal vol. 18 pp. 1120-1122. "High level HPV-16 E7 oncoprotein expression correlates with reduced pRb-levels in cervical biopsies."
KH Kim et al., (1994) Yonsei Medical Journal vol. 35, No. 1, pp. 1-9. "Expression and Localization of Human Papillomavirus Type 16 E6 and E7 Open Reading Frame Proteins in Human Epidermal Keratinocyte."
M Fiedler et al., (2005) Journal of General Virology, 86, 3235-3241. "Expression of the high-risk human papillomavirus type 18 and 45 E7 oncoproteins in cervical carcinoma biopsies."
E Guccione et al., (2002) Virology 283, 20-25. "Comparative Analysis of the Intracellular Location of the High- and Low-Risk Human Papillomavirus Oncoproteins."
H Valdovinos-Torres et al., (2008) The Open Virology Journal vol 2. 15-23. "Different Isoforms of HPV-16 E7 Protein are Present in Cytoplasm and Nucleus."
T Li et al., (2001) Carcinogenesis vol. 22. No. 6 pp. 929-934. "Human papillomavirus type 16 is an important infections factor in the high incidence of esophageal cancer in Anyang area of China."
Blevins et al., Applied and Environmental Microbiology 2007, pp. 1501-1513. "Adaptation of a Luciferase Gene Reporter Aand Iac ExpressionSystem to Borrelia burgdorferi."
EA Mirecka et al., (2006) Protein Expression and Purification 48, 281-291. "Expression and purification of His-tagged HPV16 E7 protein active in pRb binding/".
MS Lechner et al., (1994) Journal of Virology, Jul. 1994, p. 4262-4273. "Inhibition of p53 DNA Binding by Human Papillomavirus E6 Proteins."
B Bjorndal et al., (2003) Protein Expression and Purification 31 (2003) 47-55. "Expression and purification of receptor for activated C-kinase 1 (RACKI)."
ND Christensen et al., (1996) Virology 223, 174-184. "Surface Conformational and Linear Epitopes on HPV-16 and HPV•18 L1 Virus-like Particles as Defined by Monoclonal Antibodies".
Y Nomine et al., (2001) Protein Engineering vol.14 No. 4 pp. 297-305, "A strategy for optimizing the monodispersity of fusion proteins: application to purification of recombinant HPV E6 oncoprotein."
ND Christensen et al., (1994) Journal o/General Virology (1994), 75, 2271-2276. "Assembled baculovirus-expressed human papillomavirus type 11 LI capsid protein virus-like particles are recognized by neutralizing monoclonal antibodies and induce high titres of neutralizing antibodies."
T Oltersdorf et al., (1987) J. gen. Viral. (1987), 68, 2933-2938. "Identification of Human Papillomavirus Type 16 E7 Protein by Monoclonal Antibodies."
P Di Bonito et al., (2006) Infectious Agents and Cancer 2006, 1:6. "Serum antibody response to Human papillomavirus (HPV) infections detected by a novel ELISA technique based on denatured recombinant HPVI6 Li, L2, E4, E6 and E7 proteins."
JF Kearney et al., (1979) The Journal of Immunology, V 123 No. 4 p. 1548-1550. "A New Mouse Myeloma Cell Line That Has Lost Immunoglobulin Expression But Permits the Construction of Antibody-Secreting Hybrid Cell Lines."
K Seedorf et al., The EMBO Journal 1987, vol. 6, pp. 139-144. Identification of Early Proteins of the Human Papilloma Viruses Type 16 (HPV 16) and Type 18 (HPV 18) in Cervical Carcinoma Cells.
D Patel et al., (1989) J. gen. Virol. (1989),70,69-77. "Reactivities of Polyclonal and Monoclonal Antibodies Raised to the Major Capsid Protein of Human Papillomavirus Type 16."

S-H Kee et al., (1997) J. Korean Soc. Microbiol., vol. 32, No. 3, "Generation of Monoclonal Antibodies Against Human Papillomavirus Type16 E7 Protein: Usefulness for Various E7 Detection Systems."
AK Graham et al., (1991) Clin Pathol 1991;44:96-101. "Simultaneous in situ genotyping and phenotyping of human papillomavirus cervical lesions: Comparative sensitivity and specificity."
HG Kochel et al., (1991) Inl. J. Cancer: 48, 682-688. "Occurrence of Antibodies to Lt, L2, E4 and E7 Gene Products of Human Papillomavirus Types 6b, 16 and 18 Among Cervical Cancer Patients and Controls."
AK Ghosh et al., (1993) Int. J. Cancer: 53. 591-596. "Serological Responses to HPV 16 in Cervical Dysplasia and Neoplasia: Correlation of Antibodies to E6 With Cervical Cancer."
SA Jenison et al., (1990) The Journal of Infectious Disease162:60-69. "Evidence of Prevalent Genital-Type Human Papillomavirus Infections in Adults and Children."
T Fule et al., (2006) Virology 348, 289-396. "The presence of human papillomavirus 16 in neural structures and vascular endothelial cells."
Tommasino et al., Oncogene 1993, vol. 8, pp. 195-202. HPV16 E7 Protein Associates with the Protein Kinase p22 CDK2 and Cyclin A.
de Villiers et at., Virology 2004, vol. 324, pp. 17-27. "Classification of Papillomaviruses".
Banks et al., J. gen. Virol. 1987, vol. 68, pp. 1351-1359, "Identification of human papillomavirus type 18 E6 polypeptide in cells derived from human cervical carcinomas".
Thermo Scientific, Product Data Sheet for Human Papilloma Virus type 16-E7 (HPV 16-e7) Ab-1 (TVG701Y) Mouse Monoclonal Antibody. Dec. 8, 2011.
BioDesign Internation, Product Data Sheet for MAb to HPV16 E7 protein 716-218. Feb. 1, 2006.
BioDesign Internation, Product Data Sheet for MAb to HPV16 E7 protein 716-325. Aug. 3, 2005.
Chemicon International, Product Data Sheet for Mouse anti-human Papilloma Virus 16,18 E6 (C1P5) Monoclonal Antibody. Nov. 10, 2000.
Dako, Product Data Sheet for Monoclonal Mouse anti-Human Papillomavirus Clone K1H8. 2010.
G Volgareva et al., BMC Cancer 2004, 4:58. "Protein p16 as a marker of dysplastic and neoplastic alterations in cervical epithelial cells."
Digene Corporation, "hc2 HPV DNA Test," Ref. 5198-1220, 2007, 56 pages.
Matlashewski G., et al. The expression of human papillomavirus type 18E6 proteins in bacteria and the production of anti-E6 antibodies J Gen Virol (1986) 67: 1909-1916.
Radhakrishna pillai et al 1998 High-risk human papillomavirus infection and E6 protein expression in lesions of the uterine cervix Pathobiology 66(5) 240-246.
Ressler et al 2007 High-risk human popillomavirus E7 oncoprotein detection in cervical squamous cell carcinoma Clin Cancer Res 13(23) 7067-7072.
Androphy et al 1987 Identification of the HPV-16 E6 protein from transformed mouse cells and human cervical carcinoma cell lines EMBO 6(4) 989-992.
Andersson et al 2006 Expression of E6/E7 mRNA from high rish human papillomavirus in relation to CIN grade, viral load and p161NK4a Int J oncology 29:70-711.
Keegan et al 2009 Comparison of HPV detection technologies: Hybrid capture 2, preTect HPV prooer and analysis of HPV DNA viral load in HPV 16, HPV 18 and HPV 33 E6/E7 mRNA.
Inoue et al 1990 A novel monoclonal antibody against squamous cell carcinoma Jpn J Cancer res 81:176-182.
European Patent Office Communication dated Oct. 23, 2012 for Application No. 09762928.1, PCT/US2009003537.
Non-final Office Action for U.S. Appl. No. 13/029,131 dated Nov. 9, 2012.
Bosch, et al 1995. Prevalence of human papillomavirus in cervical cancer: a worldwide perspective. J Natl Cancer Inst 87:796-802.
Doeberitz, Magnus Von Knebel "New Molecular tools for efficient screening of cervical cancer", Disease Markers 17 (2001) 123-128.
Fisher, et al. "The Association of Human Papillomavirus Type 16 E6 and E7 Antibodies with stage of Cervical Cancer", Gynecologic Oncology 61,73-78 (1996) Article No. 0099.

(56) References Cited

OTHER PUBLICATIONS

Guimaraes, et al. 2005. "Immunohistochemical expression of p16lNK4a and bcl-2 according to HPV type and to the progression of cervical squamous intraepitheliallesions". J Histochem Cytochem. 53: 509-16).

Hagensee, et al. "Detection of Cervical Antibodies to Human Papillomavirus Type 16 (HPV-16) Capsid Antigens in Relation to Detection of HPV-16 DNA and Cervcal Lesions", The Jourrnal of Infectious Diseases 2000; 181: 1234-9.

Kiviat, et al. 1993. Specific human papillomavirus types as the causal agents of most cervical intraepithelial neoplasia: implications for current views and treatment. J Natl Cancer Inst 85: 934-35.

Koutsky, et al. 1992. A cohort study of the risk of cervical intraepithelial neoplasia grade 2 or 3 in relation to papillomavirus infection. N Engl J med 327:1272-1278. Abstract Only.

Kuroda, et al. 2005. The human papillomavirus E6 and E7 inducible oncogene, hWAPL, exhibits potential as a therapeutic target. Br J Cancer 92:290-3.

Li, et al. 2005. Regulation of apoptosis by papillomavirus E6 oncogene. World J Gastroenterol 11:931-37.

Longworth, et al., 2004. Pathogenesis of human papillomavirus in differentiating epithelia. Microbiol Mol Bioi Rev 68: 362-72.

Madrigal, et al. 1997. In vitro antigene therapy targeting HPV-16 E6 and E7 in cervical carcinoma. Gynecol Oncol 64: 18-25.

Meschede, et al. "Antibodies agains Early Proteins of Human Papillomaviruses as Diagnostic Markers for Invasive Cervical Cancer" Journal of Clinical Microbiology Feb. 1998, pp. 475-480.

Munoz, et al. 2003. Epidemiologic classification of human papillomavirus types associated with cervical cancer. N ENGL J MED 348:518-27.

Park, et al. 1995. Molecular biology of cervical cancer and its precursors. Cancer 76: 1902-13.

Park, et al. "HPV-16-Related Proteins as the Serolgic Markers in Cervical Neoplasia", Gynecologic Oncology 69,47-55 (1998).

Parkin, et al. 1993. Estimates of the worldwide incidence of eighteen major cancers in 1985. Int J Cancer 54:594-606.

Sehr, et al. "A generic capture ELISA for recombinant proteins fused to glutathione S-transferase: validation for HPV serology" Journal of ImmunoloQical Methods 253 (2001) 153-162.

Solomon, et al. 2002. The 2001 Bethesda Systems. Terminology for reportinQ results of cervical cytoloQY. JAMA 287:2114-19.

Studentsov, et al. "Polymer-Based Enzyme-Linked Immunosorbent Assay Using Human Papillomavirus Type 16 (HPV16) Virus-Like Particles Detects HPV 16 Clade-Specific Serologic Responses", Journal of Clinical Microbiology Jul. 2003 pp. 2827-2834.

Sun, et al., "Comparison of Peptide Enzyme-Linked Immunosorbent Assay and Radioimmunoprecipitation Assay with In Vitro-Translated Proteins for Detection of Serum Antibodies to Human Papillomavirus Type 16 E6 and #7 Proteins" Journal of Clinical MicrobioloQY Sep. 1994 pp. 2216-2230.

Tjiong, et al. "Antibodies agains Human Papillomavirus Type 16 and 18 E6 and E7 Proteins in Cervicovaginal Washings and Serum of Patients with Cervical Neoplasia" Virallmjmunolgy vol. 14, No. 4, 2001 pp. 415-424.

Veress, et al. "Human Papillomavirus DNA and Anti-HPV Secretory IgA Antibodies in Cytologically Normal Cervical Specimens" Journal of Medical Virology 43:201-207-(1994).

Viscidi, et al. 1993. Serologic response in human papillomavirus-associated invasive cervical cancer. Int. J. Cancer 55:780-784.

Walboomers, et al. "Human Papillomavirus is a Necessary Cause of Invasive Cervical Cancer Worldwide", Jouranl of PatholoQv 189: 12-19 (1999).

Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.

Zumbach, et al "Antibodies Against Oncoproteins E6 and E7 of Human Papillomavirus Types 16 and 18 in Cervical-Carcinoma Patents from Russia", Int. J. Cancer 85, 313-318 (2000) [Publication of the International Union Against Cancer].

Fitzgerald Industries International Inc., Product Data Sheet for Monoclonal Antibody to human Papillomavirus (Early Protein), Human, Clone BF7. 2006.

Wang et al., Am J. Surg Patholo. 2004, vol. 28. No. 7, pp. 901-908 Detection of Human Papillomavirus DNA and Expression of p16, Rb, p53 proteins in small cell carcinomas of the uterine cervix.

Gabriella et al., BMC Cancer. 2007, vol.7, pp. 25. Characterization of antibodies in single-chain format against the E7 oncoprotein of the human papillomavirus type 16 and their improvement by mutagenesis.

Arbyn, M., P. Sasieni, C. J. L. M. Meijer, C. Clavel, G. Koliopoulos, and J. Dillner. 2006. Chapter 9: Clinical applications of HPV testing: A summary of meta-analyses. Vaccine 24:78-89.

Castle, P. E., J. Dockter, C. Giachetti, F. A. Garcia, M. K. McCormick, A. L. Mitchell, E. B. Holladay, and D. P. Kolk. 2007. A cross-sectional study of a prototype carcinogenic human papillomavirus E6/E7 messenger RNA assay for detection of cervical precancer and cancer. Clinical cancer research : an official journal of the American Association for Cancer Research 13:2599-2605.

Cuschieri, K., and N. Wentzensen. 2008. Human Papillomavirus mRNA and p16 Detection as Biomarkers for the Improved Diagnosis of Cervical Neoplasia. Cancer Edidemiol. Biomarkers Prev. 17:2536-2545.

Dehn, D., K. C. Torkko, and K. R. Shroyer. 2007. Human Papillomavirus Testing and Molecular Markers of Cervical Dysplasia and Carcinoma. Cancer Cytopathology 111:1-14.

O'Sullivan, J. P., R. P. A'Hern, P. A. Chapman, L. Jenkins, R. Smith, and A. a. Nafussi. 1998. A case-control study of truepositive versus false-negative cervical smears in women with cervical intraepithelial neoplasia (CIN) III. Cytopathology 9:155-161.

Yim, E.-K., and J.-S. Park. 2006. Biomarkers in Cervical Cancer. Biomarker Insights 1:215-225.

Schiffman, M., A. G. Glass, N. Wentzensen, B. B. Rush, P. E. Castle, D. R. Scott, J. Buckland, M. E. Sherman, G. Rydzak, P. Kirk, A. T. Lorincz, S. Wacholder, and R. D. Burk. 2011. A long-term prospective study of type-specific human papillomavirus infection and risk of cervical neoplasia among 20,000 women in the Portland Kaiser Cohort Study. Cancer epidemiology, biomarkers & prevention : a publication of the American Association for Cancer Research, cosponsored by the American Society of Preventive Oncology 20:1398-1409.

Schweizer, J., P. S. Lu, C. W. Mahoney, M. Berard-Bergery, M. Ho, V. Ramasamy, J. E. Silver, A. Bisht, Y. Labiad, R. B. Peck, J. Lim, J. Jeronimo, R. Howard, P. E. Gravitt, and P. E. Castle. 2010. Feasibility study of a human papillomavirus E6 oncoprotein test for diagnosis of cervical precancer and cancer. Journal of clinical microbiology 48:4646-4648.

Stoler, M. H., P. E. Castle, D. Solomon, and M. Schiffman. 2007. The Expanded Use of HPV Testing in Gynecologic Practice per ASCCP=Guided Manmagement Requires the Use of Well-Validated Assays. American Journal of Clinical Pathology 127:335-337.

Woodman, C. B. J., S. I. Collins, and L. S. Young. 2007. The natural history of cervical HPV infection: unresolved issues. Nature Reviews Cancer 7:11-22.

Sep. 18, 2013 USPTO Non-Final Office Action for U.S. Appl. No. 12/456,053.

Sep. 30, 2013 USPTO Non-Final Office Action for U.S. Appl. No. 12/456,054.

Sep. 30, 2013 USPTO Final Office Action for U.S. Appl. No. 12/590,747.

Advisory Action for U.S. Appl. No. 12/456,054 dated Jun. 13, 2012.

Japan Patent Office Communication dated Apr. 2, 2013 for Application No. 2011-513504.

Final Office Action for U.S. Appl. No. 12/456,054 dated May 14, 2013.

Taiwan Patent Office Communication dated Apr. 8, 2013 for Application No. 100100781.

Taiwan Patent Office Communication dated Apr. 3, 2013 for Application No. 095142312.

Dorland's Pocket Medical Dictionary, P420, 25th Edition, 1995, W,B, Saunders Company. Philadelphia, Pennsylvania, 19106.

Notice of Allowance for U.S. Appl. No. 12/456,076 dated Aug. 1, 2012.

(56) References Cited

OTHER PUBLICATIONS

Examiner-Initiated Interview Summary and Amendment after Final initiated by the Examiner for U.S. Appl. No. 12/456,076 dated Aug. 1, 2012.
Non-final Office action for U.S. Appl. No. 11/559,366 dated Dec. 5, 2008.
Final Office action for U.S. Appl. No. 11/559,366 dated May 5, 2009.
Notice of Allowance for U.S. Appl. No. 11/559,366 dated Jan. 4, 2010.
Non-final Office action for U.S. Appl. No. 12/082,740 dated Jun. 12, 2009.
Final Office action for U.S. Appl. No. 12/082,740 dated Aug. 20, 2010.
Notice of Allowance for U.S. Appl. No. 12/082,740 dated Mar. 8, 2011.
Non-final Office action for U.S. Appl. No. 12/456,053 dated May 31, 2011.
Non-final Office action for U.S. Appl. No. 12/456,054 dated Aug. 17, 2011.
Non-final Office action for U.S. Appl. No. 12/456,055 dated Jul. 22, 2011.
EPO Communication for App. No. 09762928.1.-1223/2300824, dated Aug. 15, 2011.
Extended European Search Report for App. No. 09762928.1-1223/2300824, dated Jul. 22, 2011.
EPO Communication for App. No. 06846299.3-2402/1951915, dated Apr. 7, 2010.
Extended European Search Report for App. No. 06846299.3-2402/1951915, dated Jan. 8, 2010.
International Search Report for Int'l App. No. PCT/US2009/003537, dated Oct. 8, 2009.
International Search Report for Int'l App. No. PCT/US2009/003538, dated Oct. 15, 2009.
International Search Report for Int'l App. No. PCT/US2010/033944, dated Jul. 2, 2010.
International Preliminary Report on Patentability for Int'l App. No. PCT/US2009/003538, dated Dec. 14, 2010.
International Preliminary Report on Patentability for Int'l App. No. PCT/US2009/003537, dated Dec. 14, 2010.
Written Opinion of the International Searching Authoriy for Int'l App. No. PCT/US2009/003538, dated Oct. 15, 2009.
Written Opinion of the International Searching Authorigy for Int'l App. No. PCT/US2009/003537, dated Oct. 8, 2009.
Written Opinion of the International Searching Authorigy for Int'l App. No. PCT/US2010/033944, dated Jul. 2, 2010.
International Search Report for Int'l App. No. PCT/US2010/060765, dated Mar. 25, 2011.
Written Opinion of the International Searching Authorigy for Int'l App. No. PCT/US2010/0060765, dated Mar. 25, 2011.
International Search Report for Int'l App. No. PCT/US2006/60883, dated Jul. 18, 2007.
International Preliminary Report on Patentability for Int'l App. No. PCT/US2006/60883, dated Jul. 18, 2007.
Written Opinion of the International Searching Authority for Int'l App. No. PCT/US2006/60883, dated Jul. 18, 2007.
EPO Communication for App. No. 06846299.3-2401, dated Oct. 21, 2011.
Final Office action for U.S. Appl. No. 12/456,055 dated Jan. 6, 2012.
Final Office action for U.S. Appl. No. 12/456,053 dated Nov. 17, 2011.
Non-final Office action for U.S. Appl. No. 12/589,692 dated Feb. 7, 2012.
Non-final Office action for U.S. Appl. No. 12/589,641 dated Feb. 6, 2012.
Non-final Office action for U.S. Appl. No. 12/456,076 dated Feb. 9, 2012.
Advisory action for U.S. Appl. No. 12/456,053 dated Jan. 26, 2012.
Advisory action for U.S. Appl. No. 12/082,740 dated Nov. 3, 2010.

Berumen et al., 2001 Asian-American Variants of Human Papillomavirus 16 and Risk for Cervical Cancer: a Case Control Study. Journal of the National Cancer Institute, vol. 93, No. 17.
Bleul et al., 1991 Human Papillomavirus Type 18 E6 and E7 Antibodies in Human Sera: Increased Anti-E7 Prevalence in Cervical Cancer Patients. Journal of Clinical Microbiology, Aug. 1991, pp. 1579-1588.
Bosch et al, 2002 Te Causal Relation between Human Papillomavirus and Cervical Cancer. J. Clinical Pathology, vol. 55, pp. 244-265.
de Villiers 1997. Papillomavirus and HPV typing. Clin. Dermatol 15:199-206.
Zur Hausen 2002. Papillomavirus and cancer: from basic studies to clinical pplication. Nat. rev. Cancer 2: 342-350.
Kreimer, et al. 2005. HPV 16 semiquantitative viral load and serological biomarkers in oral and oropharyngeal squamous cell carcinomas. Int J Cancer 115: 329-32.
Nair, Pillai 2005 Human papillomavirus and disease mechanisms: relevance to oral and cervical cancers Oral Diseases 11, 350-359.
Nindl, et al. 1994. Antibodies against linear and conformational epitopes of the human papillomavirus (HPV) type 16 E6 and E7 oncoproteins in sera of cervical cancer patients. Arch. Virol. 137:341-353.
Sasagawa, et al. 2003. Mucosal immunoglobulin-A and -G responses to oncogenic human papilloma virus capsids. Int J Cancer. Apr. 10, 2003; 104(3): 328-35.
Snijders, et al. 2006 HPV-mediated cervical carcinogenesis: concepts and clinical implications J Pathol 2006; 208: 152-164.
Stacey, et al. 1992. "Expression of human papillomavirus type 16 E6 protein by recombinant baculovirus and use for detection of anti-E6 antibodies in human sera", Journal of General Virology vol. 73, pp. 2337-2345.
Stoppler, et al. 1996 Natural Variants of the Human Papillomavirus Type 16 E6 Protein Differ in Their Abilities to Alter Keratinocyte Differentiation and to Induce p53 Degradation. Journal of Virology, p. 6987-6993 vol. 70, No. 10.
Tornesello, et al. 2004 Analysis of human papillomavirus type-16 variants in Italian women with cervical intraepithelial neoplasia and cervical cancer J Med Virol.; 74(1): 117-26.
Lehtinen, et al.2001. Human papillomavirus infection, risk for subsequent development of cervical neoplasia and associated population attributable fraction. J Clin Virolo 22:117-124.
Mougin, et al. 2001. Epidemiology of cervical papillomavirus infections. Recent knowledge. Press Med 30: 1017-23.
Greenspan et el., 1999 Nature Biotechnology vol. 17, pp. 936-937. "Defining epitopes: Its not as easy as it seems."
Gravitt et al., 2008 Vaccine vol. 26S, K42-K52. "New technologies in cervical cancer screening."
Kashmiri et al., 2005 Methods vol. 36, pp. 25-34. "SDR grafting—a new approach to antibody humanization."
Tamura et al., 2000 J. Immunology vol. 164, pp. 1432-1441. "Structural correlates of an anticarcinoma antibody: identification of specificity-determining residues (SDRs) and development of a minimally immunogenic antibody variant by retention of SDRs only."
Gillison et al., 2008 J Natl Cancer Inst. vol. 100 pp. 407-420. "Distinct risk factor profiles for human papillomavirus type 16-positive and human papillomavirus type 16-nagetive head and neck cancer."
Wu et. al., 2006 Journal of General Virology vol. 87 pp. 1181-1188. "Analysis of mutations in the E6/E7 oncogenes and L1 gene of human papillomavius 16 cervical cancer isolates from China."
Taiwan Patent Office Communication dated Oct. 7, 2013 for Application No. 098119612.
European Patent Office Communication dated Oct. 28, 2013 for Application No. 12164498.3-1404.
Notice of Allowance, U.S. Appl. No. 12/590,747, filed Sep. 30, 2014.
Notice of Allowance, U.S. Appl. No. 13/319,312, filed Oct. 1, 2014.
European Patent Office Communication, EP App. No. 09762929.9, Oct. 13, 2014.
China Patent Office Communication, CN App. No. 201080060962.6, Oct. 17, 2014.
China Patent Office Communication, CN App. No. 200980131078.4, Oct. 30, 2014.
China patent Office COmmunication, CN App. No. 201080020175.9, Nov. 15, 2014.

(56) References Cited

OTHER PUBLICATIONS

Non-Final Office Action, USPTO, U.S. Appl. No. 13/520,021, filed Nov. 26, 2014.
Zhou et el., 1997. "Differential Diagnosis of Infections with Swine Transmissible Gastroenteritis virus and Procine Respiratory coronavirus using fixed-cell blocking ELISA." China Journal of Veterinarian 23 (12) 5-7.
Erdile et al., "2001. Whole cell ELISA for detection of tumor antigen expression in tumor samples." Journal of Immunological Methods 258, 47-53.
China Patent Office Communication, CN App. No. 200980131077.X, Oct. 11, 2014.
Feb. 10, 2015 China Office Communication for App. No. 201080060962.6.
Dec. 18, 2014 Japan Office Communication for App. No. 2012-509989.
Non-final Office action for U.S. Appl. No. 12/456,055 dated Mar. 21, 2014.
Non-final Office action for U.S. Appl. No. 12/590,747 dated Mar. 26, 2014.
Final Office action for U.S. Appl. No. 13/520,021 dated Apr. 14, 2014.
Apgar et al., "The Bethesda System Terminology." Am Fam Physician 2003; 68: 1992-1998.
Kovanda et al., "Characterization of a Novel Cutanous Human Papillomavirus Genotype HPV-125." PLosOne 2011; vol. 6 e22414vol.
Narechania et al., "Phylogenetic incongruence among Oncogenic Genital Alpha Human Papillomaviruses." J. Virol. 2005, 79(24): 15503.
Rudikoff et al., "Single amino acid substitution altering antigen-binding specificity." Proc. Natl. Acad. Sci 1982 vol. 79 1979-1982.
European Patent Office Communication for EPO Patent App. No. 097629299 dated Feb. 27, 2014.
China patent Office Communication for CN Patent App. No. 2010800609626 dated Mar. 10, 2014.
Liu et al., "Fixed-cell immunoperoxidase Technology." China Academic Journal, Production Technology. 1993 vol. 23 No. 2 pp. 37-38.
Taiwan Intellectual Property Office Notice of Allowance for TW Patent App. No. 098119612 dated May 9, 2014.
USPTO Non-Final Office Action dated Dec. 20, 2013 for U.S. Appl. No. 13/520,021.
Caceres-Cortes et al., Implication of Tyrosine Kinase Receptor and Steel Factor in Cell Density-dependent Growth in Cervical Cancers and Leukemias. Cancer Research. 2001;61:6281-6289.
US Patent Office non-final Office action for U.S. Appl. No. 13/319,312, Feb. 28, 2014.
China Patent Office communication for CN Patent App. No. 200980131078.4, Feb. 12, 2014.
Pillai et al., Cancer Epidemiology Biomarkers & Prevention 1996; 5: 329-335. "The presence of human papillomavirus-16/-18 E6, p53, and Bcl-2 protein in cervicovaginal smears from patients with invasive cervical caner".
Pavai et al., Romanian Journal of Morphology and Embryology 2006, 47(3): 229-234. "Comparative detection of high-risk HPV (16, 18, 33) in ervical bioptic material of County Hospital of Tg. Mures."
Japan Patent Office communication for JP Patent App. No. 2012-509989, Jan. 21, 2014.
China Patent Office communication for CN Patent App. No. 200980131077.x, Jan. 24, 2014.
Japan Patent Office Communication for JP Patent App. No. 2011-513505, Jan. 14, 2014.
Taiwan Patent Office Communication, Notice of Allowance, for TW Patent App. No. 95142312, Feb. 11, 2014.
Final Office action for U.S. Appl. No. 13/319,312 dated Jul. 24, 2014.
Final Office action for U.S. Appl. No. 12/590,747 dated Jul. 23, 2014.
Final Office action for U.S. Appl. No. 12/456,055 dated Sep. 9, 2014.
European Patent Office Communication for EPO Patent App. No. 09762929910842601.6 dated Jul. 14, 2014.
European Patent Office Communication for EPO Patent App. No. 12164498.3 dated Jun. 26, 2014.
European Patent Office Communication for EPO Patent App. No. 09762928.1 dated Aug. 26, 2014.
Japan Patent Office Communication for JP Patent App. No. 2011-513504 dated May 2, 2014.
Japan Patent Office Communication for JP Patent App. No. 2012-548021 dated Jul. 15, 2014.
China patent Office Communication for CN Patent App. No. 201080020175.9 dated May 28, 2014.
Notice of Allowance for U.S. Appl. No. 12/456,053 dated Jun. 13, 2014.
Notice of Allowance for U.S. Appl. No. 12/456,054 dated Jun. 13, 2014.

\* cited by examiner

Figure 2
A. Rabbit anti-HPV E7
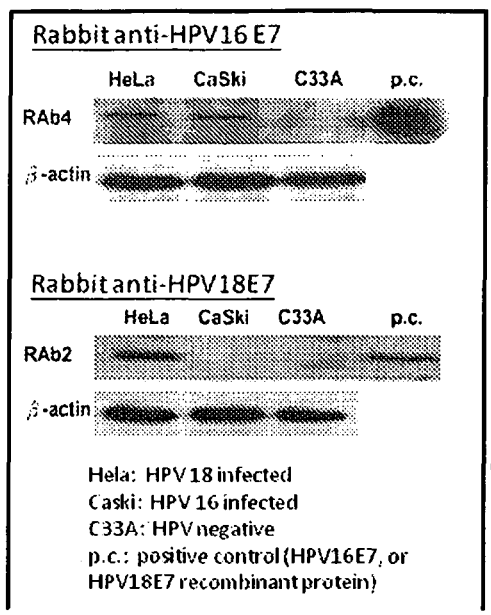
B. Rabbit anti-HPV E6
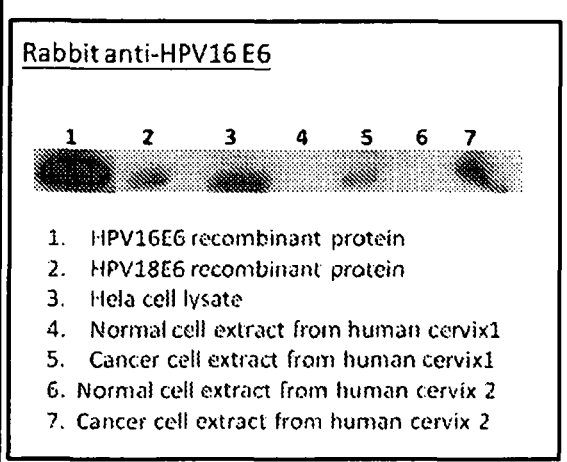

Figure 8A

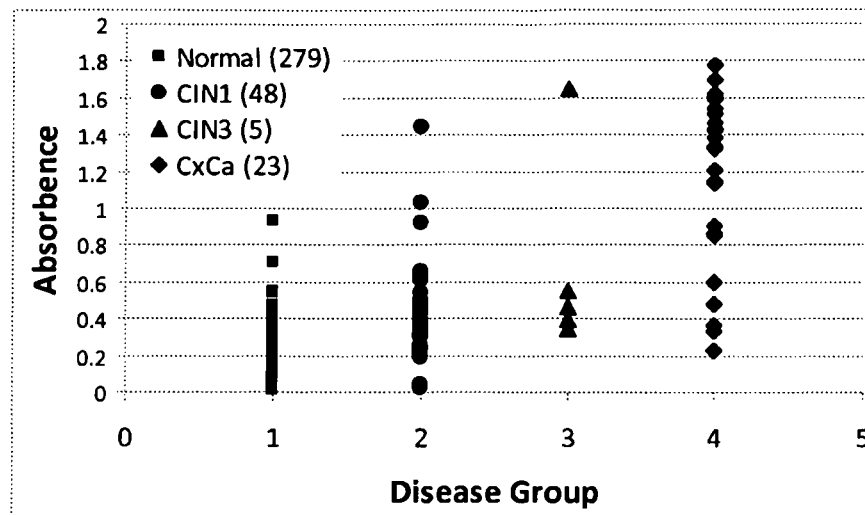

Figure 8B

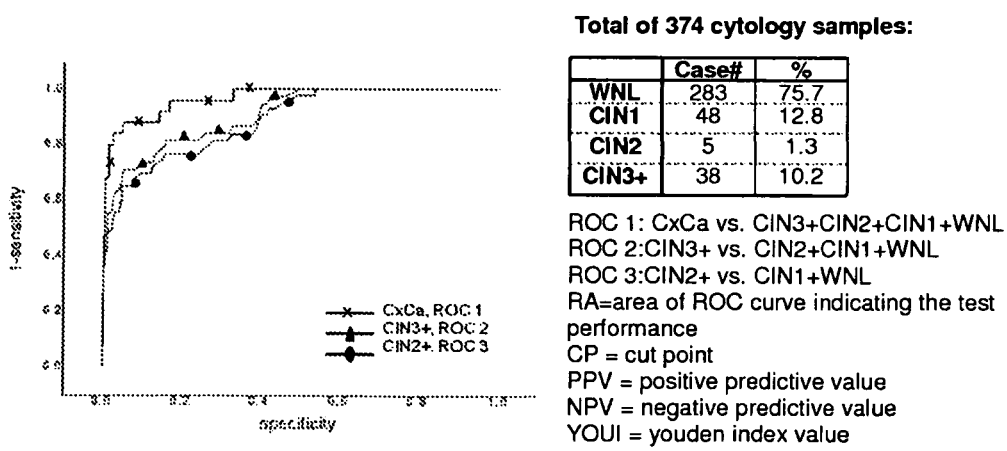

Total of 374 cytology samples:

|      | Case# | %    |
|------|-------|------|
| WNL  | 283   | 75.7 |
| CIN1 | 48    | 12.8 |
| CIN2 | 5     | 1.3  |
| CIN3+| 38    | 10.2 |

ROC 1: CxCa vs. CIN3+CIN2+CIN1+WNL
ROC 2: CIN3+ vs. CIN2+CIN1+WNL
ROC 3: CIN2+ vs. CIN1+WNL
RA = area of ROC curve indicating the test performance
CP = cut point
PPV = positive predictive value
NPV = negative predictive value
YOUI = youden index value

| case/control | RA | CP | SENS | SPEC | YOUI | PPV | NPV |
|---|---|---|---|---|---|---|---|
| CxCa/WNL+CIN1+CIN2+CIN3 | 0.9670 | 0.4735 | 0.8800 | 0.9484 | 0.8284 | 0.5500 | 0.9910 |
| CIN3+/WNL+CIN1+CIN2 | 0.9090 | 0.4600 | 0.7105 | 0.9494 | 0.6599 | 0.6136 | 0.9667 |
| CIN3+/WNL+CIN1 | 0.9110 | 0.4600 | 0.7105 | 0.9517 | 0.6622 | 0.6279 | 0.9663 |
| CIN3+/WNL | 0.9410 | 0.3235 | 0.8158 | 0.9364 | 0.7522 | 0.6327 | 0.9743 |
| CIN2+/WNL+CIN1 | 0.8890 | 0.3250 | 0.7674 | 0.8429 | 0.6103 | 0.3882 | 0.9654 |

Figure 10
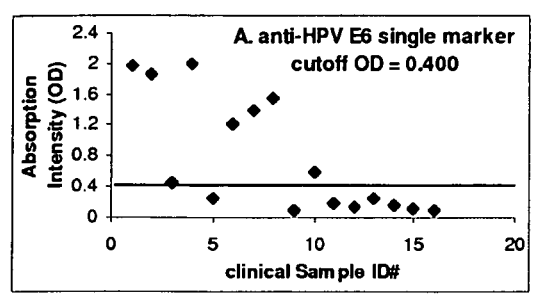
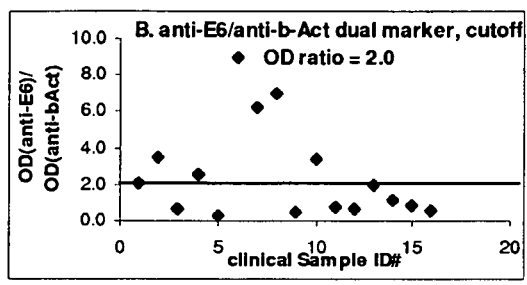

Figure 11

| 110. Obtain a clinical sample comprising a population of cells susceptible to infection by a HPV |
|---|

| 120. Disperse the clinical samples in a collection liquid |
|---|

| 130. Deposit the clinical sample into a container to immobilize the cells on a solid surface |
|---|

| 140. Obtain a first antibody that specifically binds to an HPV protein expressed by an HPV-infected cell |
|---|

| 150. Conduct one or more immunological assays on the clinical sample using the first antibody |
|---|

| 160. Detect, measure and quantify the amount of the, HPV protein that specifically binds to the first antibody expressed in the clinical sample. |
|---|

| 170. Determine a disease grade of the clinical sample based on the quantity of the HPV protein expression in the clinical sample |
|---|

HIGH THROUGHPUT CELL-BASED HPV IMMUNOASSAYS FOR DIAGNOSIS AND SCREENING OF HPV-ASSOCIATED CANCERS

CROSS-REFERENCE TO RELATED APPLICATIONS

This application claims the benefit of U.S. Prov. App. Ser. No. 61/335,540, filed Jan. 8, 2010, titled "High throughput cell-based HPV immunoassays for diagnosis and screening of HPV associated cancers," the contents of which are hereby incorporated by reference for all purposes.

BACKGROUND OF THE INVENTION

Cervical cancer is the second most common cause of cancer deaths in women worldwide, with an incidence about a half million new cases cumulatively resulting in about a quarter of a million deaths every year. In the US, cervical cancer mortality rate has decreased substantially as a result of cervical cancer screening programs that detect precancerous conditions so they can be treated before developing into cancer. The current paradigm for cervical cancer screening is based on the Pap test, a cytologically-based test of cells scraped from the cervix and examined microscopically to detect changes indicating dysplastic cell growth. The test is subjective with significant inter-observer variability, and is limited by low sensitivity and high false positive results. Reports of false-negative rates in cervical cytology have varied widely, from as low as 1.6% to almost 28%. About 4 million abnormal Pap tests are diagnosed in the United States each year as atypical squamous cells of undetermined significance (ASC-US), atypical squamous cells cannot exclude high-grade squamous intraepithelial lesion (ASC-H), low-grade squamous intraepithelial lesion (LSIL), or atypical glandular cells (AGC).

Under current practice guidelines, these cases are referred for colposcopy to further identify the subset of patients that will have clinically significant high-grade lesions (CIN2/3) or endocervical neoplasia on cervical biopsy. By some reports, patients with a cytologic diagnosis of ASC-US (over 2 million cases annually in the US) have only 5% to 17% chance of underlying CIN2/3 on cervical biopsy, and in LSIL (about 1.6 million cases in the US annually), CIN2/3 was found in up to 25%. These data suggest that for about 3 million cases with ASC-US or LSIL on Pap, colposcopy is unnecessary. Although colposcopic biopsy has historically been considered the gold standard, recent reports indicate that cervical biopsies may miss 33% to 50% of high-grade disease because of sampling or diagnostic errors. It therefore may be difficult to differentiate between false positive cervical cytology results and false-negative biopsy results. Therefore, there is strong need for a test to identify high-grade dysplasia to triage patients who can benefit most from intervention.

Although most low grade cervical dysplasias spontaneously regress without ever leading cervical cancer, dysplasia can serve as an indication that increased vigilance is needed. CIN1 is the most common and most benign form of cervical intraepithelial neoplasia and usually resolves spontaneously within two years. Because of this, LSIL results can be managed with a simple "watch and wait" philosophy. However, because there is a 12-16% chance of progression to more severe dysplasia, the physician may want to follow the results more aggressively by performing a colposcopy with biopsy. If the dysplasia progresses, treatment may be necessary. Therefore, what is needed is a method to detect HPV oncoproteins in situ. It would be particularly helpful in ASC-US or LSIL, or CIN1 patients to detect high-grade dysplasia cells and to identify those underlying CIN2 or above who may benefit immediate intervention, and avoid the anxiety associated with the "wait and see" approach.

Infection of specific epithelium cells by Human Papillomaviruses (HPV) and the resulting epithelial proliferation plays an important role for cervical carcinogenesis. About 99 percent of confirmed cervical cancer cases are found to be associated with HPV infection with biopsy-confirmed squamous intraepithelial lesions (SIL) or cervical intraepithelial neoplasia (CIN). The incidence of HPV infection, primarily transmitted through sexual contact, is highest among young women and about 20 million sexually-active men and women worldwide are currently infected. Approximately 1% of the population has genital warts and 4% of women have cervical precancerous lesions, such as low grade of squamous intraepithelial lesion (LSIL) or high grade of squamous intraepithelial lesion (HSIL) or atypical squamous cells of undetermined significance (ASC-US).

These lesions, preferentially observed in women aged 35-40 yrs, are associated with a high risk of progression toward invasive cervical cancer. It is generally thought that persistent HPV infection is essential for developing precancerous epithelial lesions. However, LSIL does not invariably progress to HSIL in women infected with a high-risk HPV strain. In fact, remission occurs in majority of human subjects diagnosed with LSIL. Although 99.7% of cervical cancers are HPV positive, viral genome integration into the host genome is required to facilitate expression of genes triggering development of HSIL or cancer. In fact, only one in every 10 women with persistent HPV infection develop higher grade CIN lesions, such as cervical intraepithelial neoplasia (CIN) grade 2 and grade 3 (CIN2, and CIN3, respectively), which in some cases, ultimately progress into cervical cancer.

Disease stages caused by HPV infection include an early stage HPV infection, a late stage HPV infection, Atypical squamous cells of undetermined significance (ASC-US), Atypical squamous cells, cannot exclude HSIL (ASC-H), Atypical glandular cells (AGC), low grade of squamous intraepithelial lesion (LSIL), high grade of squamous intraepithelial lesion (HSIL), cervical intraneoplasm CIN1, CIN2, CIN3 representing a mild, moderate, or severe cell dysplasia respectively, invasive cervical cancer, adenocarcinoma, or squamous cell carcinoma (SCC).

Nucleic acid-based HPV detection assays have been developed, but are not ideal for prognosing disease risk, in view of high cost, assay operation procedures, the requirements for facility, equipment, and highly trained personnel, and low positive predictive value for CIN. Current DNA-based assays cannot differentiate LSIL from HSIL, nor CIN lesions from non-transforming latent or remissive viral infection. Current mRNA-based assays for E6/E7 mRNA have approximately equivalent sensitivity to HPV DNA testing with higher positive predictive value. There are limited reports of assays to detect E6/E7 oncoproteins in situ. Longworth, M. S., and Laimins, L. A. (2004) Pathogenesis of Human Papillomaviruses in Differentiaing Epithelia, *Microbiology and Molecular Biology Reviews* 68, pp 362-372; and Tungteakkhun, S. S., and Duerksen-Hughes, P. J. (2008) Cellular Binding Partners of the Human Papillomavirus E6 Protein, *Arch. Virol.* 153, pp 397-408. What is needed is a low cost, simple, sensitive and specific assay that can be performed on routine practice of a clinical lab or doctor office and capable of detecting early stage of epithelial lesions, distinguish LSIL from HSIL, or predicting the risk of progression into cervical cancer.

Known protocols for the production of monoclonal antibodies to HPV are generally unsuitable for the production of anti-HPV monoclonal antibodies and cannot be used in immunocytochemical diagnostic tests for screening general human population. Veress, G., Konya, J., Csiky-Meszaros, T., Czegledy, J., and Gergely, L. (1994) Human Papillomavirus DNA and Anti-HPV Secretory IgA Antibodies in Cytologically Normal Cervical Specimens, *Journal of Medical Virology* 43, pp 201-207; Sun, Y., Shan, K. V., Muller, M., Munoz, N., Bosch, X. F., and Viscidi, P. P. (1994) Comparison of Peptide Enzyme-Linked Immunisorbent Assay and Radioimmunoprecipitation Assay with In Vitro-Translated Proteins for Detecti on fo Seruym Antibodies to Human Papillomavirus Type 16 E6 and E7 Proteins, *Journal of Clinical Microbiology* 1994, pp 2216-2220; Meschede, W., Zumbach, K., Braspenning, J., Scheffner, M., Benitez-Bribiesca, L., Luande, J., Gissmann, L., and Pawlita, M. (1998) Antibodies against Early Protein of Human Papillomaviruses as Diagnostic Markers for Invasive Cervical Cancer, *Journal of Clinical Microbiology*, 475-480; Sehr, P., Zymbach, K., and Pawlita, M. (2001) A Generic Capture ELISA for Recombinant Proteins Fused to Glutathione S-Transferase: Validation for HPV Serology, *Journal of Immunological Methods* 253, 153-162; Matlashewski, G., Banks, L., Wu-Liao, J., Spence, P., Pim, D., and Crawford, L. (1986) The Expression of Human Papillomavirus Type 18 E6 Protin in Bacteria and the Production of Anti-E6 Antibodies, *J. Gen. Virol.* 67, 1909-1916. This may reflect the use of recombinant proteins refolded following treatment with denaturants as immunogens for antibody production. Such antibodies react poorly with epitopes presented by native-conformation HPV protein produced by infected human cells. Additionally, epitopes recognized by prior art antibodies may be altered by standard procedures involved in the sampling, fixing and storing of clinical specimens. Other attempts to detect the presence of HPV related antibodies or viral proteins in a human subject by ELISA (enzyme linked immunoabsorbent assays) also generally lead to extremely low assay sensitivity and thus cannot be developed into a commercially suitable diagnostic test. Most of these ELISA assays target a single viral protein or short peptide fragments, which are not able to interact well or bind strongly and specifically to antibodies from the human subject. Specificity and sensitivity of such assays are so low that even using samples from patients confirmed with HPV associated invasive cervical cancer, only 53% of the patient samples were found positive for HPV infection. Nindl, I., Benitez-Bribiesca, L., Berumen, J., N, F., Fisher, S., Gross, G., Lopez-Carillo, L., Muller, M., Tommasino, M., Vazquez-Curiel, A., and Gissmann, L. (1994) Antibodies against Linear and Conformational Epitopes of the Human Papillomavirus (HPV) Type 16 E6 and E7 Oncoproteins in Sera of Cervical Cancer Patients, *Arch. Virol.* 137, 341-353. Given the testing populations come from general screening, with or without low grade, or precancerous lesions, the sensitivity of the assay will be too low to apply for clinical practice. Thus, there is no successful ELISA assay available as a diagnostic tool for clinical samples.

There are only about 15 types out of more than 100 types of HPV variants or strains that are associated with high-risk of CIN or cervical cancer risk. Also, around 70% of cervical cancer cases and 50% of CIN2 and CIN 3 cases are attributed to high-risk HPV type-16 and HPV type-18 infections. However, some progressive cervical cancer cases are related to infection by low risk HPV types, while infection of some HPV types will never progress into cervical cancer. It becomes important to identify those HPV infections and monitor expression of their particularly oncogenic proteins rather than just identify high risk type(s) of HPV infection. Thus, there is a need for detecting HPV oncoproteins as cervical cancer biomarkers to better identify the risk for developing HSIL, other precancerous lesions, or established cervical cancers.

Developing appropriate assays, such as HPV immunoassays, is needed for detection of such HPV oncoproteins or biomarkers for cervical cancer. The presence of E6/E7 oncoproteins in CIN 2 and CIN3 lesions can provide evidence indicating high risk of progression. However, prior art antibodies have limited utility for detecting E6/E7 oncoprotein in situ. M. S., and Laimins, L. A. (2004) Pathogenesis of Human Papillomaviruses in Differentiaing Epithelia, *Microbiology and Molecular Biology Reviews* 68, pp 362-372; and Tungteakkhun, S. S., and Duerksen-Hughes, P. J. (2008) Cellular Binding Partners of the Human Papillomavirus E6 Protein, *Arch. Virol.* 153, pp 397-408. Therefore, there is a need to develop antibodies and immunological assays for detecting HPV oncoproteins as cervical cancer biomarkers to identify HSIL or ≥CIN2 (CIN2 and above), or other precancerous lesions for use in screening for invasive cervical cancer and/or assessing the risk for malignant transformation into cervical cancer and other HPV associated cancers.

SUMMARY OF THE INVENTION

Embodiments of the invention provide methods, monoclonal antibodies, polyclonal antibodies, assays, and kits for detecting HPV infection and HPV related cancer diagnosis, screening, including infection by various HPV genotypes, early and/or late stage HPV-associated or HPV-specific cancers. The anti-HPV antibodies are used in performing HPV high throughput assays on clinical samples. Various immunological assays and kits for detecting HPV infection, cervical cancer, other HPV related cancers, early stage precancerous lesions as well as late stage cancer progression are also provided.

Disclosed are methods for quantifying an HPV protein expression in a clinical sample. The methods include the process for obtaining the clinical sample that includes a population of cells that are susceptible to infection by an HPV. The methods may also include the process for depositing the clinical sample into a container as well as the process for contacting the clinical sample with the first antibody that specifically binds to an HPV protein that is expressed by an HPV-infected cell under a condition that promotes specific binding of the first antibody to the HPV protein expressed by the population of cells. The methods may further include the process for quantifying the specific binding of the first antibody and thereby quantifying the HPV protein expression in the clinical sample.

The clinical sample may optionally include cells that are dispersed in a collection liquid in some embodiments. Such a clinical sample in these embodiments may further optionally include fixed cells.

In some embodiments, the methods may optionally include the process for measuring the cell density of the clinical sample, and the cell density of the clinical sample may optionally be normalized. In some embodiments, the methods may optionally include the process for contacting the clinical sample with a substrate that is selected from a group consisting of a membrane, a bead, and a microtiter well surface.

In some embodiments, the methods may optionally include the process for quantifying HPV protein expression to a predetermined HPV protein expression level threshold. Such process for quantifying HPV protein expression may optionally include normalization of the quantified HPV protein expression based on the number of cells present in the clinical sample. Such process for quantifying HPV protein expression may further optionally include comparison of the quantified HPV protein expression to an HPV protein standard curve. Such process for quantifying HPV protein expression may further optionally associate the predetermined HPV protein expression level threshold with a cancer in the clinical sample, and optionally associate the predetermined HPV protein expression level threshold with a pathological stage of transformation in the clinical sample.

In some embodiments, the predetermined HPV protein expression level threshold is determined from measures of HPV protein expression levels in clinical samples that include diagnosed tumors.

In some embodiments, the clinical sample may optionally include cells that are obtained from a cervical swab or a cervical scrape. The clinical sample may further optionally include cells that are obtained from an oral swab, an oral scrape, an anal swab, or an anal scrape.

In some embodiments, the HPV may be selected from the group consisting of 16, HPV 18, HPV 31, HPV 33, HPV 39, HPV 45, HPV 52, and HPV 5. In some embodiments, the first antibody that specifically binds to more than one HPV protein encoded by more than one HPV may be selected from the group consisting of HPV 16, HPV 18, HPV 31, HPV 33, HPV 39, HPV 45, HPV 52, and HPV 58. In some embodiments, the HPV protein may be selected from the group consisting of an HPV E6 protein and an HPV E7 protein. In some embodiments, the first antibody may specifically bind to an HPV E6 protein and an HPV E7 protein.

In some embodiments, the clinical sample may be deposited into a container that is a sample well of a microtiter plate.

In some embodiments, the methods for quantifying an HPV protein expression in a clinical sample may optionally further include the process of contacting the clinical sample with a labeled secondary antibody that specifically binds to the first antibody.

In some embodiments, the labeled secondary antibody may be selected from the group consisting of a direct label or an indirect label.

In some embodiments, the first antibody may optionally contain a label. Such a label may be selected from the group consisting of a direct label or an indirect label.

In some embodiments, the process for quantifying HPV protein expression may include quantifying a chromogenic substrate produced by an enzymatic label. In some embodiments, the process for quantifying HPV protein express may also include quantifying a fluorescence signal.

In some embodiments, the process for quantifying HPV protein expression may include the process of assessing an HPV-related cancer disease grade in the clinical sample based on the quantified HPV protein expression. Such an HPV-related cancer may optionally be cervical cancer.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of some embodiments and are therefore not to be considered limiting of its scope, for the intention may admit to other equally effective embodiments.

FIG. 2A provides an exemplary Western blot image illustrating detection of HPV 16 E7 recombinant protein, HPV 18 E7 recombinant protein and HPV E7 oncoproteins in cell lysate from cell cervical cancer lines using a polyclonal anti-HPV 16 E7 antibody, and a polyclonal anti HPV 18 E7 antibody.

FIG. 2B provides an exemplary Western blot image illustrating detection of HPV 16 E6 and HPV 18E6 recombinant protein, and HPV E6 oncoprotein in cell lysate from cervical tissues using a polyclonal anti-HPV 16 E6 antibody.

FIG. 8A provides an exemplary histogram showing the individual absorption intensity for each clinical sample of the total 355 cases shown in FIG. 7B.

FIG. 8B provides an exemplary summary of the ROC curve analyzed from the same 355 cytology samples shown in FIGS. 8A and 7B.

FIG. 9A provides an exemplary whole-cell ELISA result shown as absorption intensity for cell lines using anti-β actin antibody to detect the expression level of β-actin protein in HPV positive cell line Hela and HPV negative cell line C33a.

FIG. 10A provides an exemplary whole-cell ELISA result shown as absorption intensity using anti-HPV E6 antibodies to screen 16 clinical samples.

FIG. 10B provides an exemplary whole-cell ELISA result shown as the ratio of absorption intensity using the same mouse anti-HPV E6 and anti-β-actin monoclonal antibodies to screen the same 16 clinical samples tested in FIG. 10A. Signal intensity associated with samples with various amount of cells were normalized based on the signal intensity obtained using anti-β-actin antibody.

FIG. 11 is a flow chart illustrating an example of a method according to an embodiment of the invention.

DETAILED DESCRIPTION

Figures 1A, 1B, 1C:
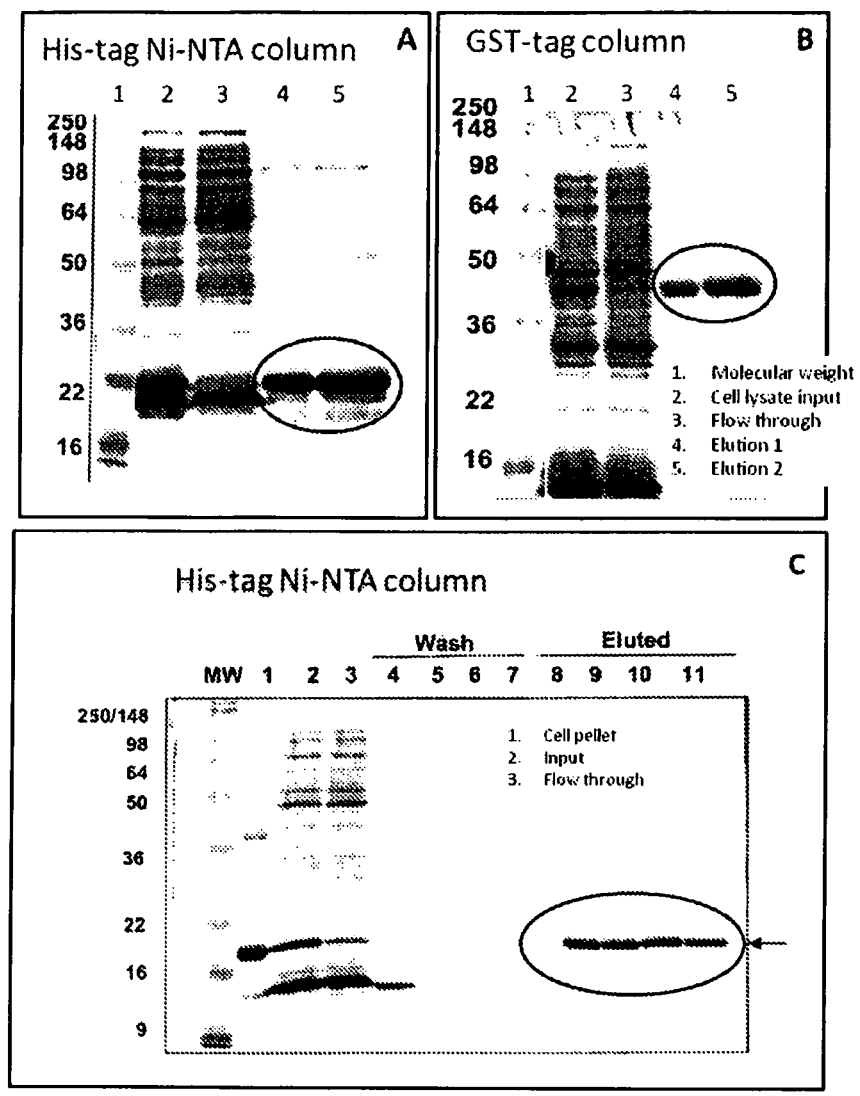
FIG. 1A provides an exemplary gel image for recombinant E7 proteins purified from His-tag Ni-NTA column according to an embodiment of the invention.
FIG. 1B provides an exemplary gel image for recombinant E7 proteins purified from a GST-tag column.
FIG. 1C provides an exemplary gel image for recombinant E6 proteins purified from a His-tag Ni-NTA column.

Papillomaviruses are DNA viruses with a DNA genome, a non-enveloped virion, and an icosahedra capsid. The double-stranded, circular HPV DNA genome contains one coding region for late genes, one coding region for early genes, and a non-coding upstream regulatory region with binding sites for the various transcription factors controlling expression of early and late genes. Two separate open reading frames in the late gene coding region encode viral capsid proteins L1 and L2. These two viral capsid proteins belong to the same class, with capsid protein L1 being the major capsid protein that is highly conserved among different HPV type. Eight open reading frames in the early gene coding region encode eight early viral proteins, designated E1, E2, E3, E4, E5, E6, E7, and E8. Early proteins E6 and E7 are oncoproteins critical for host cell immortalization and transformation as well as for long term viral replication and survival.

Infection by high risk HPVs requires two early viral proteins, E6 and E7, which are oncoproteins because they transform cells in vitro and their presence is needed to maintain malignancy Inhibition of E6 and E7 expression in precancerous or cancer cervical tissue blocks invasive cancer progression. Inside the host tissues, E6 and E7 oncoproteins work by negatively blocking the activities of endogenous host cellular regulatory proteins, p53 and retinoblastoma (Rb) tumor suppression proteins, respectively, to cause inhibition of apoptosis and deregulation of cell cycle, leading to development of cervical cancers. E6 oncoprotein binds to p53, a cellular factor that protects cells against DNA damage and regulates apoptosis, to induce degradation of p53. By reducing the levels of p53 protein, E6 oncoprotein prevents tumor cell death. E7 oncoprotein binds to Rb to induce degradation of Rb, disrupt normal cell cycle, and cause cellular proliferation. The E7 oncoprotein further destabilizes cell control through its interaction with the cyclin-dependent kinase inhibitor protein, p21. HPV E6 and E7 oncoproteins are found to be continuously produced in transformed genital tissues. These interactions set the stage for controlling host cell proliferation and differentiation (i.e., transformation), the first step in the conversion of normal cells to pre-neoplasm cells and ultimately to the full expression of cancer malignancy.

One additional event that appears to play a role in tumor progression is the integration of HPV DNA into the host genome, which frequently disrupts the open reading frame for E2, resulting in over-expression of the E6 and E7 oncoproteins and possibly causing instability of host genome. Additional cofactors and mutational events may be important in the pathogenesis of invasive cervical cancers and may include chromosomal rearrangements, loss of constitutional heterozygosity, and proto-oncogene activation.

Both HPV-16 and HPV-18 are shown to immortalize human keratinocytes in culture and are by far the most common high risk HPV types that induce invasive cervical cancer. Infection by HPV-16 type alone is associated with over 50% of cervical cancer cases, mostly resulting in squamous cell carcinoma. HPV-18 infection is more likely to induce adenocarcinomas. Some studies have indicated that adenocarcinomas in cervical tissues produce more aggressive forms of cancer with a less favorable outcome than cancers resulting from squamous cell carcinomas. This suggests that individuals with HPV-18 infection may have a much poorer prognosis than those with any other form of HPV infection.

In the United States, most Pap results are normal, however, about 4-5 million abnormal Pap test results are found each year. Most abnormal results are mildly abnormal (ASC-US, typically 2-5% of Pap results) or LSIL (about 2% of results), indicating HPV infection. Although most low grade cervical dysplasias spontaneously regress without ever leading cervical cancer, dysplasia can serve as an indication that increased vigilance is needed. CIN1 is the most common and most benign form of cervical intraepithelial neoplasia and usually resolves spontaneously within two years. Because of this, LSIL results can be managed with a simple "watch and wait" philosophy. However, because there is a 12-16% chance of progression to more severe dysplasia, the physician may want to follow the results more aggressively by performing a colposcopy with biopsy. If the dysplasia progresses, treatment may be necessary. Therefore, it is useful to provide HPV E6E7 ICC assay along with the Pap smear test for detecting HPV oncoproteins in situ, particularly helpful in ASC-US or LSIL, or CIN1 patients to detect high-grade dysplasia cells and to identify those underlying CIN2 or above who may benefit immediate intervention, and avoid anxiety for "wait and see".

High grade squamous intraepithelial lesion or HSIL or HGSIL indicates moderate or severe cervical intraepithelial neoplasia or carcinoma in situ. It is usually diagnosed following a Pap test. In some cases these lesions can lead to invasive cervical cancer, if not followed appropriately. HGSIL does not mean that cancer is present. Of all women with HGSIL results, 2% or less have invasive cervical cancer at that time, however about 20% would progress to having invasive cervical cancer without treatment. To combat this progression, HGSIL is usually followed by an immediate colposcopy with biopsy to sample or remove the dysplastic tissue. This tissue is sent for pathology testing to assign a histological classification that is more definitive than a Pap smear result. HGSIL generally corresponds to the histological classification of CIN2 or CIN3. Therefore, it is helpful to provide HPV E6E7 IHC assay along with HE (Hematoxylin and eosin stain) or HPV E6E7 ICC assay along with the Pap test for detecting HPV E6E7 oncoproteins in situ, particularly helpful in identifying CIN2/CIN3 patients.

Embodiments of the present invention provide various immunoassays and monoclonal antibodies against HPV oncoproteins as biomarkers such that over-expression of, e.g., E6, E7 oncoproteins from high-grade dysplasia cells infected by high risk and low risk HPV types can be detected by one or more antibodies. Various embodiments provide HPV whole cell immunoassay detecting the presence or amount of HPV oncoproteins present in cervical cells to identify patients with high-grade or precancerous lesions without invasive procedure In some embodiments, the binding of the one or more antibodies with the one or more proteins from one or more Papillomavirus types present in the biological samples can be examined under a microscope, detecting the presence of an agent reacting with the tagged one or more antibodies, wherein the agent includes a colorimetric agent, a fluorescent chromogen, and combinations thereof. The biological sample can include cervical cells, cervical tissues, cervical swabs, body fluids, serum, blood, tumors, cell cultures, biopsies, and combination thereof. The biological sample can be obtained from a group of people as referral due to abnormal Pap test results or as general population for routine screening of cervical cancer.

According to certain embodiments of the invention, a method of screening human subjects for Papillomavirus infection can be conducted by a whole-cell immunological assay on the solid phase of the microtiter plate containing a thin layer of human cells to intracellularly detect one or more Papillomavirus proteins from one or more Papillomavirus types present in the biological sample on the microtiter plate. The thin layer is a monolayer of cervical cells.

According to certain embodiments of the invention, one or more whole-cell immunoassays on microtiter plate containing the thin layer of the clinical cytology sample can be conducted to bind the human cells with one or more antibodies generated against one or more purified recombinant Papillomavirus proteins, or generated against one or more cellular proteins affected by HPV infection, at least one antibody is capable of recognizing a Papillomavirus oncoprotein to detect one or more proteins from one or more Papillomavirus types present in the thin layer of the clinical cytology sample on the surface of the microtiter plate. The Papillomavirus oncoprotein includes but not limited to, HPV-16 E6 protein, HPV-16 E7 protein, HPV-18 E6 protein, HPV-18 E7 protein, and combinations thereof. The cellular proteins include but not limited to, p16$^{INK}$4a, pRB, p53, E2F, E2F activated cell cycle protein, cyclin dependent kinase, CDK4, CDK6, Ki-67 (MIB-1), MYC protein, cyclin-A, cyclin-B, cyclin-E, telomerase-TERC, MCM2, TOP2A, heat shock protein 40 (HSP$_{40}$), heat shock protein 60 (HSP$_{60}$), heat shock protein 70 (HSP$_{70}$), CA9/MN, laminin5, bm-3a, CDK N2, topoisomerase 2A, microsome maintenance protein-2, microsome maintenance protein-4, microsome maintenance protein-5, survivin, VEGF, p27 (kip1), and p21 (waf).

Embodiments of the invention provide various immunoassays and monoclonal antibodies against HPV viral proteins such that infection by most high-risk HPV types can be detected by a single monoclonal antibody and/or a general pan antibody. The invention provides HPV cell-based ELISA assay to detect the presence of HPV proteins in high throughput format. A method for detecting papillomavirus in a human subject includes conducting one or more immunological assays, such as a cell-based ELISA on a clinical sample from the human subject processed into a mixture of morphologically abnormal and normal human cells. The biological sample may comprise cells obtained from one or more the following: cervical tissues, cervical swabs, body fluids, serum, blood, tumors, cell cultures, biopsies, and combination thereof. The biological sample can be obtained from a group of people as general population for routine screening of cervical cancer.

In one certain embodiments, an automated high throughput HPV cell-based ELISA of the inventions can be used in general screening for HPV infection and early diagnosis for cervical cancer and other cancers, specific detection of invasive cervical cancer, detection of other HPV related cancers, early stage precancerous lesions as well as late stage cancer progression. Various novel monoclonal antibodies against HPV proteins, useful as biomarkers and useful tools for detecting HPV viral proteins, HPV oncoproteins, early screening of cervical cancer, and diagnosing CIN and/or invasive cervical and other cancers, are provided.

The one or more papillomavirus proteins from one or more papillomavirus types present in a clinical sample can be detected by one or more tagged antibodies generated against one or more purified recombinant papillomavirus proteins. The one or more antibodies can be tagged with different agents suitable in the art for detection, wherein the agent may comprise a colorimetric agent, a chemiluminescent agent, a fluorescent chromogen, and combinations thereof. In one embodiment, at least one antibody of the one or more antibodies is capable of recognizing a papillomavirus early protein. The papillomavirus early protein may be, for example, HPV-16 E6 protein, HPV-16 E7 protein, HPV-18 E6 protein, HPV-18 E7 protein, and combinations thereof.

According to certain embodiments, the mixture of human cells can be applied to the microtiter plate from a liquid-based solution. Prior to the microplate, the mixture of cells can be filtered by different pore size to separate cervical cells from others in the mixture. The cells can also be centrifuged through a gradient containing solution to obtain cervical cells from the mixture of collection. The surface of the microtiter plate can be a glass or a plastic surface treated with an agent to retain adherence of cells on the surface. The surface of the microtiter plate can also include a membrane-based filter to allow separation of cervical cells from unwanted blood cells, mucus, debris, etc. The pore size of the membrane can range from 5 micron to 10 micron. The membrane can be pretreated with an agent to allow adherence of cervical cells on the surface. The thin layer of human cells can be, for example, a monolayer of cervical cells.

According to certain embodiments, a normalization step is carried out to normalize the number of cells tested in each well of a microtiter plate. For example, cellularity (=cell pellet in ul/sample solution in mL) can be obtained to normalize cell variation across samples. As another example, after the whole-cell ELISA analysis, the cells on the microtiter plate can be counter-stained by an agent for colorimetric or fluorescent staining of the nuclei to quantify the number of cells tested in each well. As another example, the whole-cell ELISA can comprise use of two or more antibodies, at least one for detecting an HPV oncoprotein, and one for detecting a general cellular protein, for example, beta-actin, as an internal control. This enables normalizing the number of cells between patients, and calculating a ratio for cells expressing HPV specific proteins by HPV specific antibody with one detection, and cells counter stained with the other detection. The ratio obtained from the two detections represented the degree of HPV E6E7 oncoproteins present in the mixture of abnormal and normal cells.

In one embodiment, the detection system for cell-based ELISA can comprise a plate reader with capability for absorbance of visual light, UV light, illuminometer, various wave lengths for excitation and emission of fluorochrome, and combination thereof. In embodiments using a membrane-based filter microtiter plate with a colorimetric substrate, the precipitated colormetric development can be visualized without necessarily using instrumentation. This membrane-based ELISA can also be used with a solution-based substrate for colorimetric or chemiluminescent detection. In another embodiment, the detection system can be a CCD camera or other imager to capture the measurement, which optionally can be obtained using a laser as a source of incident radiation.

In certain embodiments, a cytological Papanicolaou smear assay on a clinical sample can also performed to compare the results of the cytological Papanicolaou smear test with the results of the one or more immunohistological assays. Nucleic acid hybridization assay on a clinical sample can also be performed to detect the presence of a Papillomavirus genome.

Various embodiments generally relate to various methods, detection assays, kits, polyclonal and monoclonal antibodies, polypeptides, recombinant proteins, and nucleic acids useful for detecting HPV infection, including general HPV infection as well as infection by various HPV genotypes, including high-risk HPVs and low-risk HPVs. Various novel monoclonal antibodies against HPV proteins, useful as biomarkers and useful tools for detecting HPV viral proteins, HPV oncoproteins, early screening of cervical cancer, and diagnosing disease stages ≥CIN2 or ≥CIN3 are provided. The tools described herein can also be used in early clinical screening for HPV infection and general diagnosis for cervical cancer and other HPV related cancers.

In one embodiment, the one or more purified recombinant Papillomavirus proteins include Papillomavirus E6 protein, Papillomavirus E7 protein, Papillomavirus L1 protein and combinations thereof. The recombinant Papillomavirus proteins include, but not limited to recombinant HPV-16 E6 proteins, recombinant HPV-16 E7 proteins, recombinant HPV-18 E6 proteins, recombinant HPV-18 E7 proteins, and HPV-16 L1 proteins, recombinant HPV-18 L1 proteins and combinations thereof.

Some embodiments provide various monoclonal antibodies against HPV viral proteins such that infection by high risk and low risk HPV types can be detected by a single monoclonal antibody. Some embodiments also provide HPV non-type specific monoclonal antibodies for detecting one or more HPV types. That is, a single antibody can recognize HPV protein from more than one virus type. We refer to these as pan-specific antibodies. The one or more Papillomavirus types includes high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof.

Definitions for the following terms and abbreviations are set out below:

NILM: Negative for Intraepithelial Lesion of Malignancy. NILM is used when there is no cellular evidence of neoplasia; this may include organisms and/or other non-neoplasm findings such as reactive/reparative changes.

ASC-US: Atypical Squamous Cells of Undetermined Significance. Cells are usually the size of intermediate or superficial squamous cells and have nuclear changes that are suggestive but not diagnostic of LSIL or SIL not otherwise specified.

ASC-H: Atypical Squamous Cells cannot exclude HSIL. Cells are usually the size of metaplastic cells and may be seen singly or in clusters; they are suggestive but not diagnostic of HSIL.

LSIL: Low grade Squamous Intraepithelial Lesion, encompassing: HPV cytopathologic effect/mild dysplasia/CIN 1.

HSIL: High grade Squamous Intraepithelial Lesion, encompassing: moderate dysplasia/CIN 2 and severe dysplasia/CIS/CIN 3 and HSIL with features suspicious for invasion.

Squamous cell carcinoma (SCC): Cancer of the cervix, locally invasive into neighboring tissues, blood vessels, lymph channels and lymph nodes. In its advanced stages it can be difficult to treat and may prove fatal. Depending on the stage or degree of invasion, invasive cancer of the cervix may be treated with local excision, hysterectomy, radical hysterectomy, radiation, and chemotherapy.

Adenocarcinoma: While most cancer of the cervix comes from the squamous cells making up the exterior skin, there is an occasional cancer that arises from the mucous-producing cells which line the endocervical canal leading up into the uterus. This glandular-type is called "adenocarcinoma" as opposed to "squamous cell carcinoma." Adenocarcinoma can be difficult to detect. Unlike squamous cell cancer: Adenocarcinoma precursors, when present, can be difficult to identify on Pap smears. The slow progression of squamous cell dysplasia into squamous cell cancer of the cervix is not as uniform in adenocarcinoma.

Competitive Advantage of the Invention

Attempts to detect the presence of HPV related antibodies in a human subject by ELISA (enzyme linked immunoabsorbent assays) generally lead to extremely low assay sensitivity and thus cannot be developed into a commercially suitable diagnostic test. Nindl, I., Benitez-Bribiesca, L., Berumen, J., N, F., Fisher, S., Gross, G., Lopez-Carillo, L., Muller, M., Tommasino, M., Vazquez-Curiel, A., and Gissmann, L. (1994) Antibodies against Linear and Conformational Epitopes of the Human Papillomavirus (HPV) Type 16 E6 and E7 Oncoproteins in Sera of Cervical Cancer Patients, Arch. Virol. 137, 341-353. Most of these ELISA assays target a single viral protein or short peptide fragments, which were not able to interact well or bind strongly and specifically to antibodies from the human subject. The assay specificity and sensitivity are so low such that even using samples from patients confirmed with HPV associated invasive cervical cancer, only 53% of the patient samples were found positive for HPV infection. Thus, there is no successful ELISA assay available as a diagnostic tool for clinic al samples.

Some embodiments are directed to resolve three challenges that exist in developing E6, or E7 antibodies for CIN2/3. First, HPV proteins are intracellular proteins present in small quantities in clinical samples. Second, the conformation of the HPV protein is sensitive to the process of sample collection. Third, there are many HPV types each with a distinct E6 coding sequence. Therefore, HPV proteins have not been successfully mass produced and purified from HPV infected cultured cell lines to be used as immunogens for antibody production. Known anti-HPV antibodies produced against either small synthetic peptides or denatured recombinant protein are generally unsuitable for use in clinical diagnosis, because they do not necessarily react with the naturally occurring HPV viral proteins in infected human cells. Veress, G., Konya, J., Csiky-Meszaros, T., Czegledy, J., and Gergely, L. (1994) Human Papillomavirus DNA and Anti-HPV Secretory IgA Antibodies in Cytologically Normal Cervical Specimens, *Journal of Medical Virology* 43, pp 201-207; Sun, Y., Shan, K. V., Muller, M., Munoz, N., Bosch, X. F., and Viscidi, P. P. (1994) Comparison of Peptide Enzyme-Linked Immunisorbent Assay and Radioimmunoprecipitation Assay with In Vitro-Translated Proteins for Detecti on fo Seruym Antibodies to Human Papillomavirus Type 16 E6 and E7 Proteins, *Journal of Clinical Microbiology* 1994, pp 2216-2220; Meschede, W., Zumbach, K., Braspenning, J., Scheffner, M., Benitez-Bribiesca, L., Luande, J., Gissmann, L., and Pawlita, M. (1998) Antibodies against Early Protein of Human Papillomaviruses as Diagnostic Markers for Invasive Cervical Cancer, *Journal of Clinical Microbiology*, 475-480; Sehr, P., Zymbach, K., and Pawlita, M. (2001) A Generic Capture ELISA for Recombinant Proteins Fused to Glutathione S-Transferase: Validation for HPV Serology, *Journal of Immunological Methods* 253, 153-162; Matlashewski, G., Banks, L., Wu-Liao, J., Spence, P., Pim, D., and Crawford, L. (1986) The Expression of Human Papillomavirus Type 18 E6 Protin in Bacteria and the Production of Anti-E6 Antibodies, *J. Gen. Virol.* 67, 1909-1916. Another technical challenge relates to protein conformation changes that occur upon formalin fixation and paraffin embedding in human tissue naturally infected with HPV. This contributes to the difficulty in detecting HPV proteins in clinically-relevant samples. The fact that E6 oncoprotein contains numerous cysteine amino acids and the correct topography of the E6 oncoprotein requires formation of many disulfide bonds makes the production and in situ detection of such oncoproteins very difficult. These factors provide an explanation for the fact that the available antibodies produced from denatured recombinant proteins or synthetic peptides do not work sufficiently well to allow their use in reliable in vitro diagnosis. In addition, it was also known that certain immunological assays using small peptides of the E6 protein results in extremely low assay specificity and sensitivity. Nindl, I., Benitez-Bribiesca, L., Berumen, J., N, F., Fisher, S., Gross, G., Lopez-Carillo, L., Muller, M., Tommasino, M., Vazquez-Curiel, A., and Gissmann, L. (1994) Antibodies against Linear and Conformational Epitopes of the Human Papillomavirus (HPV) Type 16 E6 and E7 Oncoproteins in Sera of Cervical Cancer Patients,

*Arch. Virol.* 137, 341-353. Thus, there are no available E6 proteins in native form, purified as immunogens, for generating anti-HPV antibodies capable of detecting viral oncoproteins present in clinical samples for in vitro diagnosis.

The present invention provides a novel approach to viral oncoprotein testing, using a novel combination of tools that include novel antibodies, recombinantly-expressed HPV proteins including but not limited to E6, E7, L1, L2 and a whole-cell assay. The present invention enables the first whole-cell ELISA for detecting intracellular HPV oncoprotein in clinical samples. This whole-cell ELISA enables the detection of HPV oncoproteins as biomarkers for true precancers in the diagnosis and screening of cervical cancer and other HPV associated cancers.

Recombinant HPV E6 and antibody development. Development of E6 antibodies have been hampered by the difficulty of obtaining E6 oncoprotein, which is prone to aggregation. Furthermore, detection of E6 protein in clinical samples is difficult due to sample collection conditions which produce a protein conformational change. We have overcome the technical barriers to produce HPV E6 recombinant protein in a non-denatured, soluble form and have developed highly specific antibodies against HPV E6 oncoproteins. The present invention provides pan anti-HPV E6 antibodies, i.e. single antibodies capable of detecting most prevalent high-risk HPV types in fixed cells. The same method was used to develop recombinant HPV E7 protein and antibody to obtain pan anti-HPV E7 antibodies. The same method was also used to develop recombinant HPV L1 protein and recombinant HPV L2 protein, and antibody to obtain pan anti-HPV L1 and pan anti-HPV L2 antibodies.

Whole cell assay approach. We have also developed IHC and ICC assays to detect E6, E7, and L1 proteins using these types of antibody in fixed clinical samples. Our IHC and ICC study on cervical tissues and exfoliated cervical cytological samples demonstrate the utility of these antibody types that are capable of detecting E6, E7, and L1 proteins in clinical samples. To avoid invasive procedure for biopsy, and to avoid the subjectivity and variability of interpretation of morphology based staining and IHC/ICC results, we developed an objective platform based on whole-cell ELISA, to provide a robust tool for cervical cancer screening. The HPV E6, E7, and L1 whole-cell ELISAs respectively measure intracellular E6, E7, and L1 proteins objectively in a high throughput assay and enable the detection of HPV oncoproteins as biomarkers for true precancers in the diagnosis and screening of cervical cancer and other HPV associated cancers. These assays require no cell lysis, avoid use of detergent that may result in a change of the protein conformation in the process of protein extraction, and enable direct detection of native E6, E7, and L1 proteins in cervical cells. The assays provide an objective test to identify patients with high-grade precursor, thus avoids unnecessary invasive procedure for colposcopy and biopsy. This ELISA format uses more specific and clinical relevant biomarkers to provide an objective, more sensitive, robust, and high throughput test that can be automated to be suitable for routine cervical cancer screening and will provide a binary (presence or absence) or semi-quantitative measurement of E6, E7, and L1 proteins.

At present, there are no commercially-available immunological assays to clinically measure the presence of HPV-associated proteins or antibodies. Embodiments of the invention thus provide a diagnostic tool useful for diagnosis of HPV infection, dysplasia, and HPV related cervical cancer. In addition, the results from the immunological assays as described herein can be used to compare with other commercially-available immunological assays specifically-designed for p53 and RB. It is known that infection high risk type HPVs, such as HPV-16 and HPV-18 may cause cervical cancer due to the expression of E6 and E7, the viral oncoproteins that induce cervical cell malignancy and alter/reduce the expression of p53 and RB endogenous proteins of the host cells, leading to cellular dysfunction and ultimately carcinoma. Thus, it is contemplated to compare the assays results on the levels of all of these proteins altered by HPV infection perform on clinical samples, e.g., cervical tissues, body fluids, serum, etc., from the same human subjects.

FIG. 11 illustrates an example of a method according to one or more embodiments of the invention.

At step 110, clinical sample comprising a population of cells susceptible to infection by a HPV is obtained. The clinical sample is a sample includes cervical cells, cervical tissues, cervical swabs, body fluids, serum, blood, tumors, cell cultures, biopsies, and combination thereof from a living human subject. The clinical sample can be obtained from a group of people as referral due to abnormal Pap test results or as general population for routine screening of cervical cancer.

At step 120, the clinical samples are dispersed in a collection liquid. As an example of whole-cell immunoassay on ELISA plate, cells from cervical scrapes were directly smeared on the surface of well of the microtiter plate for objective measurement. As another example, cervical cells are collected into a liquid based solution, and are processed according to the instructions from the manufactures.

At step 130, the clinical sample is deposited into a container to immobilize the cells on a solid surface. Clinical samples collected by liquid-based solution are processed according to the instructions from the manufactures. The thin layer of cells plated on the well of microtiter plate or other type of surfaces such as glass or plastic surfaces coated or treated for suitable binding, for example, plastic surface treated for cells to bind, or plastic surface treated for protein to bind; glass or plastic surfaces with a thin layer of membrane attached. The surface can also be in a form of beads to maximize the contacting area. Each sample was loaded to a single container. Multiple containers were combined to form a format as a microtiter plate for high-throughput process. The cells immobilized are then fixed, followed by antigen retrieval, blocking, incubated with the various anti-HPV antibodies of the invention.

At step 140, a first antibody (anti-HPV antibody) that specifically binds to an HPV protein expressed by an HPV-infected cell is obtained. The anti-HPV antibodies may be directly labeled with a detection agent or may be indirectly detected by a secondary antibody labeled with a detection agent. Cells on the microtiter plate containing HPV proteins will bind to the anti-HPV antibody in solution. Unbound anti-HPV antibody will be removed by washing, and a secondary antibody with tagged conjugate will be added followed by appropriate substrate to be analyzed by a plate reader.

At step 150, one or more immunological assays on the clinical samples are conducted using the first antibody that specifically binds to an HPV protein expressed by an HPV-infected cell. Unbound anti-HPV antibody will be removed by washing, and a secondary antibody with tagged conjugate will be added followed by appropriate substrate to be analyzed by a plate reader. As an example, the anti-HPV antibodies may be directly tagged with biotin, or may be detected by a secondary antibody tagged with HRP or biotin, or other agents to be detected following appropriate agents used as substrate or may be tagged with fluorochromogen to be directly detected with appropriate reader. The pre-antibody blocking solution may contain certain proteins or BSA, or serum or other agents to block the cells from nonspecific binding of antibody. The post blocking solution may contain similar solution as the pre-antibody blocking solution with less proteins or serum to be used along with primary antibody incubation. The solution containing HPV antibodies may be in concentrated form, or may be in diluted form as ready to use reagent. The solution containing secondary antibodies may be in concentrated form, or may be in diluted form as ready to use reagent.

At step 160, the amount of the, HPV protein that specifically binds to the first antibody expressed in the clinical sample is detected, measured and quantified. Substrate suitable for the readout of the signal intensity that represents the binding of antibody to target protein in the sample is added to the sample to quantity the proteins expressed in the sample. As an example, for colorimetric technique, TMB ELISA substrate or its equivalent is used to detect horseradish peroxidase activity that arises from the binding of the antibody to the protein. Upon the addition of TMB to the sample, it yields a blue color that changes to yellow upon addition of acid stop solution (Max absorbance at 450 nm). The signal intensity was read using colorimetric plate reader. As another example, for chemiluminescent technique, commercially available chemiluminescent substrate is used to detect horseradish peroxidase activity that arises from the binding of the antibody to the protein. Upon the addition of the substrate to the sample, chemiluminescent intensity was read using chemiluminescent plate reader. As still another example, for fluorescent technique, commercially available fluorescent substrate was used to detect horseradish peroxidase activity that arises from the binding of the antibody to the protein. Upon the addition of the substrate to the sample, fluorescent intensity was read using fluorescent plate reader.

At step 170, a disease grade of the clinical sample based on the quantity of the HPV protein expression in the clinical sample is determined. As an example, the expression level of HPV oncoprotein can be quantified by using known amount of HPV recombinant protein as standard curve. A cutoff threshold in signal readout is chosen to quantify the expression level of HPV protein, and is used to determine the positive rate of the assay, and to determine the disease grade of the sample.

The one or more recombinant proteins as described herein can be expressed in various suitable systems, such as bacterial expression systems, viral expression systems, yeast expression systems, mammalian expression systems, e.g., in *E coli*, yeast, baculovirus, and/or mammalian cell cultures, generally known in the field. Although the polypeptides could be obtained by other means, embodiments of the invention provide one or more recombinant proteins mostly in (or close to) their native forms, which may be a much desirable conformation for binding with antibodies from tissues of human subjects with HPV infection in an immunological assay. The recombinant protein obtained is used for the positive control of the assay, also is used as immunogens to raise the antibodies.

HPV recombinant proteins can be any kind of HPV viral proteins, HPV proteins of early genes and/or late genes, including, but not limited to, E2, E6, E7, L1, L2 and can be from various HPV types. Some embodiments provide recombinant proteins, such as recombinant hybrid proteins containing a partial sequence or a full length sequence of HPV oncogenic proteins. For example, full-length E6, E7, and/or L1 polypeptide sequence, which have been found very difficult to obtain and purify due to undesirable aggregation during protein purification, protein instability, low levels of expression, low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus unsuitable as commercialized diagnostic tools.

HPV recombinant proteins were produced to use as immunogens for generating antiserum, and screening of monoclonal antibody from hybridoma cell lines: Cloning and production of various recombinant proteins include genes encoded by HPV 16 E6 and HPV 18 E6 gene, HPV16 E7 and HPV18 E7 gene, HPV16 L1 and HPV18 L1 gene. To provide the recombinant proteins mostly in (or close to) their native forms with much desirable conformation, recombinant HPV E6, E7 or L1 proteins expressed in *E coli* was purified from soluble fraction, then concentrated, and dialyzed with PBS to be used as immunogens. Immunization of mice and fusion was done by standard procedure to select clones met our screening criteria on ELISA. Each hybridoma cell line was grown in tissue culture and injected to mice for ascites production. Ascites were collected, isotyped, and purified by Protein G column for use in HPV immunoassays.

Some embodiments are directed to monoclonal antibodies against HPV proteins. Obtaining high quantity of purified recombinant HPV proteins in native conformation as immunogens becomes the first critical step in generating antibodies specific for detecting HPV proteins in clinical samples. E6 and E7 is known to be very difficult to isolate and purify due to undesirable aggregation during protein purification, protein instability, low levels of expression, and low immunogenic responses of purified proteins. We have overcome the technical barriers to produce HPV E6 and E7 recombinant protein in a non-denatured, soluble form. To demonstrate that the purification method that we have developed results in a conformation closely approximating the native form to bind the anti-HPV antibodies, we have used the HPV infected cervical samples (high risk-HPV positive by PCR) that contain human HPV antibody to test the purified recombinant HPV proteins. Studies of using such purified E6 and E7 recombinant protein to detect HPV infection confirmed the binding of these proteins to anti-HPV antibody produced by human immune response to HPV infection. These results suggest that such purified recombinant HPV proteins are suitable for use as an immunogens to raise antiserum and generate antibodies that can recognize natural HPV viral proteins in vivo. We have used non-denatured, soluble E6 and E7 recombinant proteins for antigenic stimulation and have thereby developed highly specific antibodies against HPV E6 and E7 oncoproteins.

The polyclonal and monoclonal antibodies obtained are useful for diagnosis of HPV infection in cervical biopsies, serum or genital swabs specimen and in assessing disease levels in human or other subjects. In particular, diagnosis using the antibodies of the invention permits identification of patients at high risk for malignant transformation as well as identification of the particular phase of CIN associated with the sample. The antibodies can also be used in analysis of serum to detect HPV virus or to detect the virus in metastases of infected tissue, as well as to monitor the progression of HPV immunotherapy, anti-HPV vaccines, or other therapeutic agents directed to control of HPV infection and/or cervical carcinoma.

Accordingly, some embodiments provides a monoclonal antibody capable of recognizing a common epitope on E6 protein from two different HPV types, both HPV16 and HPV18 by screening antibody-producing hybridoma cells with a purified HPV16 E6 recombinant protein and a purified HPV18 E6 recombinant protein. Some embodiments provide a monoclonal antibody that recognizes a common epitope on HPV 16 E7 and HPV 18 E7 proteins. As examples, the monoclonal antibodies were used to test on various biological samples, cell lines, and/or clinical samples of various grades of epithelial lesions (CIN2, CIN3, LSIL, HSIL, ASC-US) as well as different cervical cancers, squamous cell carcinoma (SCC, a type of common cancer) and adenocarcinoma (ADC, a type of gland cancer).

Exemplary monoclonal antibodies obtained include a type of monoclonal antibody capable of binding to both HPV16 E6 and HPV16 E7 viral proteins; another type of monoclonal antibody capable of binding to all HPV16 E6, HPV16 E7, and HPV16 L1 viral proteins; and another type of monoclonal antibody capable of binding to both HPV18 E6 and HPV18 E7 viral proteins. Accordingly, the monoclonal antibodies produced using methods of the invention are capable of binding to two or more HPV viral proteins from the same HPV type selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof.

These monoclonal antibodies can be used for one or more immunological assays to detect HPV infection and HPV-related cervical cancer and other diseases. The suitable immunological assay may include ELISA (enzyme linked immunoabsorbent assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochemistry for tissues and/or cervical cells, and immunocytochemistry assays followed by flow cytometry.

We have used non-denatured, soluble E6 and E7 recombinant proteins for antigenic stimulation and have thereby developed highly specific antibodies against HPV E6 and E7 oncoproteins.

Initial studies have supported the use of our novel anti-E6 and anti-E7 antibody via different applications: ELISA, Western blot, and immunohistochemistry (IHC) in cervical cancer tissues. The validation results from clinical samples suggest our anti-E7 monoclonal antibody can be used as a biomarker for identification of high-grade dysplasia in cervical tissues, and can be used in reliable clinical diagnostic assays.

There are more than 40 HPV types identified in genital infection with 15 types identified as high-risk type from cervical cancer, among which HPV type 16 accounts for about 50% and type 18 accounts for an additional 20-25% of cervical cancer cases. However, since many HPV infections—including HPV 16 and HPV 18 infections—are self-limited, detection of HPV E6 and E7 oncoprotein in tissue can be the most direct and robust test to identify high-grade dysplasia cells, regardless of HPV types. Our goal was to obtain HPV E7 specific monoclonal antibody capable of reacting with most high-risk HPV types associated with cancer development. We screened hybridoma clones with HPV recombinant proteins from HPV type 16 and type 18 (accounting for about 75% of cervical cancer cases) to identify clones capable of detecting the relevant protein from the majority or all of the high risk HPV types. In addition, we screened hybridoma clones with unrelated HPV proteins to eliminate those with non-specific binding to HPV structural proteins. The purified recombinant human Papillomavirus proteins used in the hybridoma screening include, but are not limited to, HPV 16 E6 protein, HPV 16 E7 protein, HPV 16 L1 protein, HPV 18 E6 protein, and HPV18 E7 protein. Comparing our IHC results with HPV genotyping data from the tissues tested, our anti-E7 antibodies identify most of the common high-risk types, including not only HPV 16 and HPV 18, but also additional high-risk types closely related to type 16 (i.e. type 31, 33, 35, 52, 58) and type 18 (i.e. type 45).

One aspect of the invention provides a method of producing monoclonal antibodies. The method includes obtaining various purified recombinant papillomavirus proteins and screening antibody-producing hybridoma cells with two or more purified recombinant papillomavirus proteins to obtain a monoclonal antibody capable of recognizing a common epitope on the two or more purified recombinant human papillomavirus proteins and binding to the two or more purified recombinant papillomavirus proteins and corresponding papillomavirus viral proteins in biological and clinical samples.

In addition, the monoclonal antibody with binding specificity to two or more human papillomavirus viral proteins is produced by using a method which includes positive selection of the antibody-producing hybridoma cells with two or more purified recombinant papillomavirus proteins and negative selection of the antibody-producing hybridoma cells with non-HPV proteins. For example, the method may include screening antibody-producing hybridoma cells with two or more purified recombinant papillomavirus proteins by selecting the antibody-producing hybridoma cells with positive reactivity to the two or more purified recombinant papillomavirus proteins and with negative reactivity to non-HPV proteins, such that the antibody-producing hybridoma cells generate the monoclonal antibody with binding specificity to the two or more human papillomavirus viral proteins. The two or more purified recombinant papillomavirus proteins may include, for example, HPV 16 E6 protein, HPV 16 E7 protein, HPV 16 L1 protein, HPV 18 E6 protein, HPV18 E7 protein, HPV 18 L1 protein, and combinations thereof.

Another method of the invention includes screening antibody-producing hybridoma cells with a first purified recombinant human papillomavirus protein from a first HPV type and a second purified recombinant human papillomavirus protein from a second HPV type to obtain a monoclonal antibody capable of recognizing a common epitope on human papillomavirus proteins from two or more different HPV types. Still, another method of the invention provides screening antibody-producing hybridoma cells with a first purified recombinant human papillomavirus protein from a first HPV type and a second purified recombinant human papillomavirus protein from a second HPV type to obtain a monoclonal antibody capable of recognizing a specific epitope on only one of the first and the second purified recombinant human papillomavirus proteins and not the other purified recombinant human papillomavirus proteins.

Another aspect of the invention provides a method and a monoclonal antibody capable of binding to two or more HPV viral proteins from different HPV types. The monoclonal antibody is obtained by screening antibody-producing hybridoma cells with two or more purified recombinant papillomavirus proteins by selecting the antibody-producing hybridoma cells with positive reactivity to the two or more purified recombinant papillomavirus proteins from different HPV types and with negative reactivity to non-HPV proteins, such that the antibody-producing hybridoma cells generate the monoclonal antibody with binding specificity to the two or more HPV viral proteins. Exemplary monoclonal antibodies include a type of monoclonal antibody capable of binding to HPV 16 E7 and HPV 18 E7 proteins; another type of monoclonal antibody capable of binding to HPV16 E6 and HPV18 E6 proteins; and another type of monoclonal antibody capable of binding to HPV16 L1 and HPV18 L1 proteins, among others, to be used for various immunological assays.

The monoclonal antibody described herein is a pan antibody which recognizes common epitope among different virus types. HPV 16 and HPV 18 are the most two common types causing cervical cancer. Among 13 HPV high-risk types, two major groups include HPV 16 and its related types such as type 31, 33, 35, 52, 58, and HPV 18 and its related type such as type 45. Although HPV 16 and HPV 18 are distinct group among over 40 HPV types for genital infection, genomic sequence analysis shows homology between HPV 16 and HPV 18 and among other types as shown in Table 1. We screened the antibody with HPV 16 E6 and HPV 18 recombinant protein to obtain the pan antibody capable of binding to HPV 16, 31, 33, 52, 58, and HPV 18, 45. This pan antibody is novel for detection of HPV E6 proteins present in most high-risk type of HPV infection.

TABLE 1

Amino acid sequence homology of L1, E6 and E7 for different HPV Types

|  | L1 | E6 | E7 |
|---|---|---|---|
| HPV 16 v. HPV 18 | 63% | 53% | 42% |
| HPV 16 v. HPV 31 | 81% | 65% | 73% |
| HPV 16 v. HPV 33 | 79% | 62% | 60% |
| HPV 18 v. HPV 31 | 64% | 51% | 38% |
| HPV 18 v. HPV 33 | 65% | 46% | 44% |
| HPV 31 v. HPV 33 | 78% | 57% | 59% |
| HPV 16 v. HPV 6A | 68% | 35% | 56% |
| HPV 16 v. HPV 11 | 68% | 34% | 55% |
| HPV 6A v. HPV 11 | 92% | 81% | 83% |

Still another aspect of the invention provides HPV type-specific monoclonal antibody capable of binding to only a first HPV viral protein, but not a second HPV viral protein different from the first HPV viral protein. Such a monoclonal antibody can be obtained by screening antibody-producing hybridoma cells with positive reactivity to a first purified recombinant papillomavirus protein from a first HPV type and with negative reactivity to a second purified recombinant papillomavirus protein from a second HPV type, wherein the first and second viral proteins correspond to the first and the second purified recombinant papillomavirus proteins of the first and second HPV types. The HPV type-specific monoclonal antibody may be capable of binding to only one viral protein, the first viral protein. The first viral protein may include a viral protein from a HPV type selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof. Exemplary monoclonal antibodies include monoclonal antibodies recognizing only one viral protein selected from the group of HPV 16 E6 protein, HPV 16 E7 protein, HPV 16 L1 protein, HPV 18 E6 protein, HPV18 E7 protein, and HPV 18 L1 protein. Such type of monoclonal antibody produced by the method of the invention can be used to detect the presence of a specific viral protein in one or more immunological assays.

The antibodies as developed herein lend themselves to the high quality and properly purified recombinant proteins encoded by HPV early and late genes, useful in immunological assays to generate very high sensitivity and specificity for screening HPV infection and cervical cancer detection. The monoclonal antibody can be used for one or more immunological assays selected from the group consisting of ELISA (enzyme linked immunoabsorbent assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochmistry for tissues and/or cervical cells, and immunocytological assays followed by flow cytometry, among others. In one embodiment, the one or more immunological assays may be non-invasive with minimal or no additional instrument required.

Known protocols for the production of monoclonal antibodies to HPV are generally unsuitable for the production of anti-HPV monoclonal antibodies and cannot be used in immunocytochemical diagnostic tests for screening general human population. This is because antibodies produced by these protocols will not necessarily react with naturally-occurring HPV protein found in infected human cells. In addition, the epitopes recognized by prior art antibodies will not necessarily be those epitopes which are resistant to the standard procedures involved in the sampling, fixing and storing of clinical specimens.

The purified recombinant proteins were used to raise antiserum, polyclonal and monoclonal antibodies by injecting to animal species and screening with the recombinant proteins for specific binding. Many convenient animal species can be used to prepare the appropriate antisera, and these antisera can be used directly. Suitable animal species include mice, rats, rabbits, guinea pigs, or even larger mammals, such as sheep. For administration to such animals, the recombinant proteins are generally administered in the presence of an adjuvant, usually Freund's complete adjuvant, and the polyclonal sera are harvested periodically by standard techniques.

Monoclonal antibodies may be produced using the method of Kohler and Milstein or by more recent modifications thereof by immortalizing spleen or other antibody-producing cells from injected animals to obtain monoclonal antibody-producing clones. HPV positive and negative human serum samples are useful in screening monoclonal antibody producing hybridoma to ensure the specificity of the monoclonal antibody clones. More than one positive clone reactive with purified E6, E7, and L1 can be obtained and further injection of the obtained cell cultures to mice or other animal source can be used to produce ascites for purifying the monoclonal antibodies, such as by protein A affinity column chromatography. The purified antibody can be used as either the capture or detection probes in our ELISA or to be conjugated with detection enzymes, such as (HRP, AP, etc.) for ELISA substrate detection in an absorbent, fluorescent, or chemiluminescence detection system.

The basic techniques for cloning and for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art.

For example, the one or more immunological-based assays may include antibody-based assay having purified papillomavirus proteins coated on a surface, such as bottom surfaces of a microtiter plate, a membrane, and/or a chip. The surfaces that are not coated can be blocked with non-binding proteins. Then, a sample to be tested, such as a sample (samples from human subjects) likely with antibodies against HPV virus or HPV-associated proteins can bind to the surface by binding to the coated purified papillomavirus proteins. The bound antibody-purified papillomavirus protein complex can be detected by a secondary antibody and a number of commercially available detection systems using colorimetric, chemiluminescent, or fluorescent substrate. One example of secondary antibody is a horse radish peroxidase-conjugated secondary antibody, such as an antibody against-human immunoglobins (specific for IgG, IgA, etc.). The final results can be read by a microplate reader or visualized by eye if colorimetric substrates are used.

As another example, an antigen assay involves coating of a primary antibody, such as a capture antibody having an affinity for binding to an antigen of interest, on a surface, such as bottom surfaces of a microtiter plate, a membrane, a chip, etc. The antigen of interest may be, for example, a papillomavirus protein, an oncoprotein, a capsid protein, which may be encoded by a HPV viral gene, e.g., an early gene or a late gene, etc. After blocking unbound portions on the surface, the clinical sample to be analyzed can be applied to bind with the capture antibody to form an immunocomplex, which can be detected by another primary antibody or a detection antibody by binding to the antigen of interest. Hence, the two primary antibodies or a pair of the capture antibody and the detection antibody interact with the antigen of interest, much like a sandwich. The capture antibody can be the same or different antibody as the detection antibody as long as the two antibodies can specifically bind to the antigen of interest, e.g., a HPV viral protein, a HPV oncoprotein, a capsid protein, among others.

Next, the sandwiched bound antibody-antigen complex can be detected by a secondary antibody, which have an affinity for the detection antibody and facilitate measurement by a standard immunological complex detection system using colorimetric, chemiluminescent, fluorescent and many different kinds of substrates. The final readouts or visualizations can be performed by an instrument with appropriate light absorbance readers or directly visualized by eye and compared the results to a control sample. Positive results indicate binding of the antigen of the interest to the primary antibodies, the capture antibody, and the detection antibody, and thus the presence of the antigen of interest in the clinical sample. In the contrary, negative results indicate no binding of the antigen of the interest to the primary antibodies and thus the absence of the antigen of interest in the clinical sample.

The one or more immunological assays can be used to detect at least three kinds of target proteins of interest, including, but not limited to, antigen, antibody, and antigen/antibody immunocomplex (also referred hereafter as antigen tests, antibody tests, and antigen/antibody immunocomplex tests, respectively), among others.

The formats of the one or more immunological assays may be a microplate format (e.g., 32 wells, 48 wells, 96 wells or 384 wells), a vertical or lateral membrane-based rapid test, a protein chip with multiple spot or multiplexed. The principles of the assays are the same as described above except detection systems vary depending on the substrate chosen for analyzing the results in different readouts or forms by an instrument specific designed for the assays. In addition, the procedures, conditions, binding specificity, developed in one type of immunological assay in one format can be adapted into a different format of the same or a different immunological assay, and/or a different immunological assay in the same or a different forma.

An ELISA procedure can also be carried out in a variety of formats. Methods for enhancement of ELISA sensitivity using several layers of anti-antibodies, streptavidin-biotin complexes and enzyme-anti-enzyme antibody complexes are well known in the art. The solid support or surface for fixation of antigen is usually plastic, as described here, but a variety of other solid supports such as latex or agarose have been described. It is also not necessary for the antigen to be directly fixed onto the solid support/phase. There is for example a commonly used ELISA format that fixes the specific antigen to the solid support via a solid-phase-fixed antibody to the antigen, so-called catching antibody ELISA or sandwich ELISA. A special case of immunoassay which involves a blotting (transfer) of antigen to a solid support in sheet format is termed immunoblotting. Typically, the solid support is nitrocellulose or nylon membranes/sheets, but other supports have been described. Various binding, mixing, incubating, coating, or blotting interactions are involved in an ELISA assay. Prior to an ELISA assay, the antigens or antibodies can be separated according to their sizes by gel electrophoresis or similar methods. Detection of antibodies bound to the specific antigen on the sheet can be carried out in similar ways as for other immunoassays.

The 96-well format is a high throughput screening format useful to optimize assay procedures and conditions. Other format with different number of wells can also be used. Positive controls and negative controls were also performed on, for example, serum samples from donor subjects that are positive for HPV infection and virgin subjects without HPV infection. The immunological assays were found to result in high sensitivity, for example, in detecting E6, E7 and L1 antibodies. Initial titration curves were performed and ELISA assays conditions were optimized.

Assay conditions suitable for binding are those conditions (in terms of salt concentration, pH, detergent, protein concentration, temperature, etc.) which allow for binding to occur, for example, between a capture agent and a target agent, between a primary antibody and a secondary antibody, between a recombinant protein and a protein or antibody that can bind to the recombinant protein, etc., in solid support or in solution. Such conditions, particularly with respect to antibodies and their antigens, are well known in the art (see, e.g., Harlow and Lane (Antibodies: A Laboratory Manual Cold Spring Harbor Laboratory, Cold Spring Harbor, N.Y. (1989))). Conditions suitable for specific binding typically permit binding partners or pairs that have a dissociation constant ($K_D$) of less than about $10^{-6}$ M to bind to each other selectively.

Anti-E6, anti-E7, and anti-L1 capture antibody were attached to the bottoms of the microtiter plate for coating before the purified recombinant proteins were added. Then a detection antibody is used to detect the captured recombinant protein bound to the capture antibody. Optimized capture and detection antibody concentrations were identified. The concentration of the recombinant proteins in the reaction resulting in linearity in the ELISA assay for antigen detection was determined. These sandwiched ELISA assays were repeated multiple times on the same day, as well as on different days to determine assay reproducibility and reliability. Specificity and sensitivity for each assay were determined. Furthermore, the ELISA assay was shown to have selectivity in detecting cervical cancers versus other cancers, for example, to demonstrate non-cross reactivity with samples from ovarian or endometrial cancers. Since it is known that HPV is found in most if not all cervical cancer cells, but is usually not associated with other cancers, the antigen tests as described herein should not detect antigens associated with other cancers. To test for this selectivity, for example, extracts from tissues of ovarian and endometrial cancer cell lines can be tested and can also serve as negative controls in the antigen tests.

As an example of the HPV whole-cell ELISA, basic test procedure is as following:

TABLE 2

HPV whole-cell ELISA

| Step | | in | throughput |
|---|---|---|---|
| 1 | clinical samples collected in liquid based solution | Vial (10-20 ml) | — |
| 2 | transfer to 96-well microplate | microplate | 96 |
| 3 | Fixation | microplate | 96 |
| 4 | Permeabilization | microplate | 96 |
| 5 | add blocking | microplate | 96 |
| 6 | add primary anti-E6 or anti-E7 antibody | microplate | 96 |
| 7 | Wash | microplate | 96 |
| 8 | add conjugated 2nd antibody | microplate | 96 |
| 9 | add substrate | microplate | 96 |
| 10 | Analysis | plate reader | 96 |

Once the human cells from cervical scrapes are processed and fixed into a monolayer or thin layer of cells on the microtiter plate, the whole-cell ELISA assay was performed by blocking the wells of microtiter plate with pre-antibody blocking solution for a period of time followed by the incubation with the HPV antibodies. The plates were then washed 3 to 5 times with PBS or $H_2O$, or other solution to remove any unbound HPV antibody. Then the slides were incubated with the secondary antibody, for example, anti-mouse IgG HRP, followed by washing and binding of appropriate substrate for detection. As an example for the substrate, TMA is oxidized in the presence of peroxidase and hydrogen peroxide resulting in the deposition of a blue solution, at the site of enzymatic activity depending upon the amount of enzyme present. The blue solution indicates the specific binding of HPV antibodies with HPV proteins present in the cells. The assay can be performed at room temperature or higher temperature to accelerate the binding reaction. This HPV whole-cell ELISA assay can be performed manually, or operated by automation, thus provides a powerful tool to screen for HPV infection and detection of HPV oncoproteins in the epithelium cells from cervical scrapes.

To demonstrate that the HPV ELISA assay can identify dysplasia cells from different disease grades, samples from mild, moderate, severe, or invasive of neoplasia were all tested. These samples include but not limited to, for example, CIN1, CIN2, CIN3, LSIL, HSIL or ASC-US. To demonstrate that the whole-cell ELISA assay described herein can be used to test for various sample sources from various grades in various liquid based solutions, different grades of samples in different liquid based solutions were also tested in some embodiments.

Cancer of the cervix is among the most common forms of cancer affecting the reproductive organs. It is locally invasive into neighboring tissues, blood vessels, lymph channels and lymph nodes. In its advanced stages it can be difficult to treat and may prove fatal. Prior to developing cancer of the cervix, there is usually a period of pre-cancerous change that is reversible, known as dysplasia. While most cancer of the cervix comes from the squamous cells making up the exterior skin, there is an occasional cancer that arises from the mucous-producing cells which line on the endocervical canal leading up into the uterus. This glandular-type is called "adenocarcinoma (ADC)" as opposed to "squamous cell carcinoma (SCC)". Unlike squamous cell cancer, adenocarcinoma precursors, when present, can be difficult to identify on Pap smears, thus making adenocarcinoma difficult to detect. The slow progression of squamous cell dysplasia into squamous cell cancer of the cervix is not as uniform in adenocarcinoma. Consequently, adenocarcinoma of the cervix is frequently detected at a more advanced stage than squamous cell carcinoma. Treatment is similar to that of the more common squamous cell cancer. However, since it is more often found at a more advanced stage, more aggressive treatment is often needed. Thus, it becomes critical to detect the presence of the HPV oncoproteins from early screening of adenocarcinoma cells in the liquid-base solutions using the HPV whole-cell ELISA assay described in some embodiments.

Pathological characterization of HPV related neoplasia.

Moderate dysplasia means that the skin of the cervix is growing moderately faster than it should and has progressed beyond the mild stage. A biopsy of the cervix shows immature basal cells growing partway through to the surface of the skin, without significant maturation. Moderate dysplasia is important because there is a much greater risk that these changes will advance, and if untreated, it will progress into invasive cervical cancer. For that reason, moderate dysplasia is known as a "high grade" lesion, or HGSIL. Another synonym for this condition is "CIN2" (Cervical Intraepithelial Neoplasia, Grade II). Moderate dysplasia on a Pap smear usually indicates that further study of the cervix with colposcopy is needed. If moderate dysplasia is confirmed, then it is usually treated. Treatments might include cryosurgery, LEEP, or laser. Following treatment, frequent Pap smears are usually obtained as follow-up to make sure that if there is a recurrence (about 10% chance), that the recurrence is promptly diagnosed and further treatment performed.

If the abnormal cells invade through the basement membrane into the underlying tissues, they are considered cancer. For severe dysplasia, it is not considered as cancer but a pre-cancerous problem as the abnormal cells in dysplasia do not invade through the basement membrane. Thus, by definition, they are not cancer. Carcinoma in situ means that there are abnormal cells extending the full thickness of the skin. These cells individually look just like cancer cells. Carcinoma in situ is considered by many authorities to be clinically equivalent to severe dysplasia, or CIN3, and it should be promptly and carefully evaluated. Treatment might include eliminating the abnormal cells by freezing them (cryosurgery), vaporizing them (laser), or shaving them off with an electrified wire loop (LEEP). In some circumstances, more extensive surgery in the form of a cervical cone biopsy is required to eliminate the problem.

Example 1

HPV Recombinant Protein Expression, Purification, and Preparation to be Used as Immunogens for Generating Antiserum, and Screening for Monoclonal Antibody from Hybridoma Cell Lines HPV recombinant proteins can be any kinds of HPV proteins, HPV proteins of early genes and/or late genes, including, but not limited to, E2, E6, E7, L1, L2 and can be from various HPV types. One aspect of the invention provides recombinant proteins, such as recombinant hybrid proteins containing a partial sequence or a full length sequence of HPV oncogenic proteins. For example, full-length E6, E7, and/or L1 polypeptide sequence, which have been found very difficult to obtain and purify due to undesirable aggregation during protein purification, protein instability, low levels of expression, low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus unsuitable as tools for clinical in vitro diagnostics.

Cloning of an exemplary oncogenic E6 or E7 early gene is described herein. DNA fragment containing the amino acid coding region of the HPV-16 E6. E7 or L1 gene was obtained by polymerase chain reaction (PCR) amplification. The DNA fragment was sub-cloned into a histidine tag expression vector to generate the plasmid DNA for the expression of E6 or E7 recombinant protein. Other types of expression vectors with histidine tag (e.g., $His_6$, $His_8$, etc.), glutathione-S-transferase (GST) fusion, maltose-binding-protein (MBP), among others, was also used. In addition, the DNA fragment can be sub-cloned into other expression systems, i.e. e. baculovirus, yeast, etc to express E6 or E7 recombinant proteins from various HPV types and strains. For example, L1 recombinant protein from HPV 16 expressed in baculovirus was obtained and designated as HPV-16-L1-baculo.

The E6 or E7 recombinant proteins were expressed in E. coli BL21 (DE3) using IPTG driven induction. After two hour induction of protein expression at 37° C., The E6 or E7 recombinant proteins using protocols recommended by the suppliers (Amersham and New England Biolabs, respectively) were obtained and purified to a final concentration of about 1 mg/L. Longer induction time and re-flow through on protein purification column were found to generate higher protein yield, resulting in highly concentrated purified recombinant proteins at a yield of about 2-10 mg/L. The purity of the recombinant GST-E6 or His E6 proteins was estimated to be >90% based on PAGE analysis. Recombinant E6 or E7 fusion proteins was used to detect the presence of E6 or E7 antibody on clinical samples and was also be used as immunogens for production of polyclonal antiserum and monoclonal antibodies.

The basic techniques for cloning and for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art. Details of our purification and characterization procedures for HPV recombinant proteins are described in co-owned U.S. Pat. No. 7,732,166, titled "Detection Method for Human Papillomavirus (HPV) and Its Application in Cervical Cancer," the entire contents of which are hereby incorporated by reference in their entirety.

FIG. 1 C. Gel purification images for recombinant E6 proteins using His-tag Ni-NTA column. The eluents corresponding to lanes 8-11 (oval circled and arrowed) were collected to obtain purified recombinant HPV E6 protein in a non-aggregated monomeric form. FIG. 1C demonstrate the expression of full-length HPV-18 E6 recombinant protein induced by IPTG analyzed by SDS-PAGE. The molecular weight of the resulting His-tagged-HPV18-E6 recombinant protein is about 20.5 KD. The purity of the recombinant E6 proteins was estimated to be about 90% or more based on PAGE analysis. The purified recombinant E6 proteins as shown in FIG. 1C were used in one or more immunological assays, for example, to be used as a detecting antibody in antibody assays, etc. The purified recombinant E6 proteins were also used to as immunogens for generating antiserum, polyclonal antibody, and monoclonal antibodies specific against HPV-16 E6 protein.

Figure 1D:
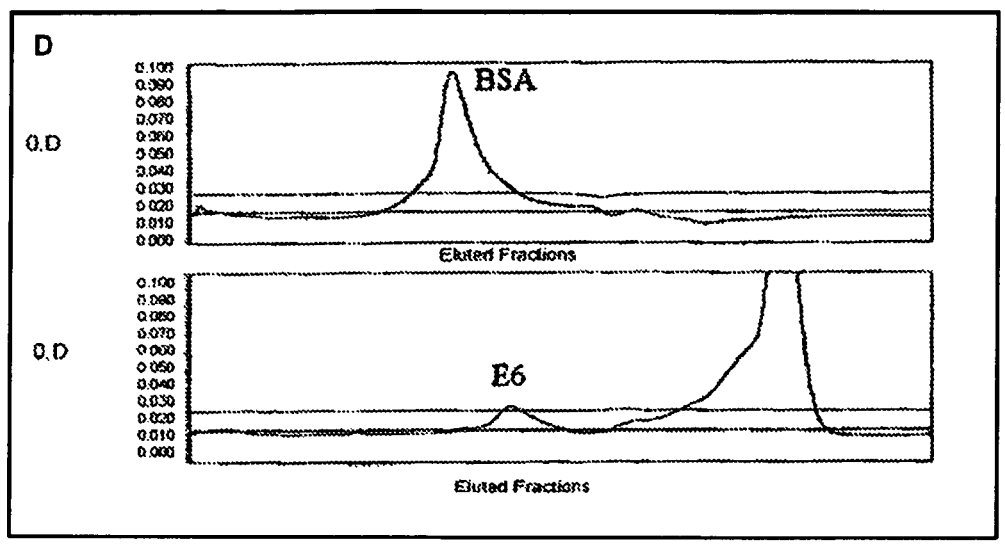

As an another example, FIG. 1D demonstrates the result of gel filtration column chromatography of the purified recombinant E6 protein, demonstrating that the purified recombinant protein HPV-16-E6 is a monomeric soluble protein with molecular size about 20.5 kDa. The purified recombinant E6 protein is eluted later than BSA.

FIG. 1A-FIG. 1B, Gel purification images for recombinant E7 proteins using His-tag Ni-NTA and GST-tag column respectively. The eluents corresponding to lanes 4-5 (oval circled) were collected to obtain purified recombinant HPV E7 protein in a non-aggregated monomeric form. FIG. 1A and FIG. 1B are a SDS-PAGE gel, showing one exemplary purified recombinant His-tagged (FIG. 1A) and GST-tagged (Figure B) HPV-18-E7 proteins. As an example shown in FIG. 1B, the GST-tagged HPV-18-E7 recombinant proteins is purified to homogeneity as a major single band with a molecular weight of 37.2 KDa as indicated by a circle. The molecular weight of the resulting recombinant HPV-18 E7 GST protein is about 37.2 KD. The recombinant HPV-18 E7 GST proteins were obtained and purified to a final concentration of about 1 mg/L. The recombinant HPV-18 E7 HIS proteins were also obtained and purified to a final concentration of about 1 mg/L. Other expression systems were also used to express E7 recombinant proteins from various HPV genotypes types and strains. For example, E7 recombinant protein from HPV-18 was obtained and designated as HPV-18-E7-his. Recombinant E7 fusion proteins or recombinant E7 baculovirus proteins were used to detect the presence of E7 antibody on clinical samples and were also be used as immunogens for production of polyclonal antiserum and monoclonal antibodies.

In general, recombinant proteins from various high risk HPV types and low risk HPV types or strains were obtained by cloning of early and late genes by polymerase chain reaction (PCR) amplification using a pair of forward and reverse primers using procedures as described herein and in various recombinant protein expression systems. For example, a recombinant N-terminal fragment of HPV-16 L1 protein was also obtained by expression in His-tagged expression system. For example, partial and full length L1 recombinant proteins from HPV-16 were obtained from a his-tagged expression system and a baculovirus expression system and designated as HPV-16L1N-his and HPV-16L1-his (baculo-SF9). Recombinant L1 proteins and/or recombinant L1 partial proteins were used to detect the presence of L1 antibody on clinical samples and were also used as immunogens for production of polyclonal antiserum and monoclonal antibodies.

A recombinant N-terminal fragment of HPV 16 L1 protein was also obtained by expression in His-tagged expression system. The molecular weight of the HPV-16 L1 N-terminal recombinant protein about 34 KD. C-terminal fragments can also be obtained. The same techniques were applied to produce recombinant HPV-18 L1 protein, and used as immunogens for generating antiserum, polyclonal and monoclonal antibodies.

Example 2

Anti-HPV Antibody Preparation

Recombinant HPV proteins produced using the techniques as described in Example 1 were used as immunogens for generating antiserum, polyclonal antibodies, and monoclonal antibodies.

The basic techniques for cloning and for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art. Details of our procedures for antibody production the characterization of the produced antibodies, and certain assays are described in co-owned U.S. U.S. Pat. No. 8,865,162, filed on Jun. 10, 2009, titled "Novel Monoclonal Antibodies against HPV Protein," U.S. Pat. No. 8,859,218, filed on Jun. 10, 2009, titled "In situ Detection of Early Stages and Late Stages HPV Infection," U.S. Pre-Grant Publication No. 2010/0003704, filed on Jun. 10, 2009, titled "In situ Detection of Early Stages and Late Stages HPV Infection," and U.S. Pat. No. 8,278,056, filed on Jun. 10, 2009, titled "Detection of Early Stages and Late Stages HPV Infection." The entire contents of each are hereby incorporated by reference for all purposes in their entirety.

FIG. 2. Western blot images of detecting HPV recombinant protein and HPV protein in cell lysate from cervical cancer cell line, and cervical tissues using polyclonal anti-HPV E6 and anti-HPV E7. FIG. 2A, Rabbit anti-HPV 16 E7 antibody (RAb4) and rabbit anti-HPV 18 E7 antibody (RAb2) were used to detect HPV E7 protein expression level in HPV18 infected Hela cells, HPV16 infected CaSki cells, and HPV negative C33A cells. Purified recombinant protein was used as a positive control with dark stain. Anti-beta actin antibody was used as an internal control, which also showed dark stain for all the cell lines. The results indicate that RAb4 detects HPV E7 protein from cell lysate that are HPV18 infected (HeLa) and HPV 16 infected (CaSki). These data suggest that polyclonal anti-HPV 16E7 antibody is crossed reactive with HPV 18 E7 protein. RAb2 detects HPV E7 protein from cell lysate that are HPV18 infected. FIG. 2B, Rabbit anti-HPV16 E6 antibody was used to detect HPV E6 protein in cell lysate extracted from cervical cancer tissues. HPV16E6 and HPV18E6 recombinant protein was used as a positive control and dark stain was obtained (lanes 1 and 2). HPV18 infected HeLa cell lysate also gave dark stain (band 3). Normal cell extract from human cervix gave negative results (lanes 4 and 6). Cancer cell extract from human cervix gave positive results (lanes 5 and 7). These data demonstrate the polyclonal anti-HPV16E6 antibody can detect both HPV 16 and HPV 18 E6 recombinant protein and protein from cervical cancer tissues.

Example 2.6

The Specificity of Anti-HPV Antibodies

One or more immunological assays can be used to test the specificity of the monoclonal antibodies generated by screening the hybridoma cell lines with two or more HPV recombinant proteins. EIA (Enzyme Immuno Assay) and/or Western blots were used as the assay format to test the specificity of the HPV antibodies described herein. Various purified recombinant HPV proteins, including the original screening proteins used for obtaining the anti-HPV antibodies and other proteins not used for screening, were used to coat on the microtiter plate to test the specificity of the obtained anti-HPV antibodies on EIA. Proteins in cell lysate from cervical cancer cell lines (with or without HPV infection) were also used to test the specificity of the anti-HPV antibodies by western blot. To confirm the binding and reactivity of the HPV antibodies with proteins from HPV infected cell lines, western blot is very useful to demonstrate specific protein bands corresponding to the proteins present in the HPV-infected cell lines. These western blots proteins bands can be compared to recombinant HPV proteins at their expected molecular weight positions on SDS-PAGE gels. Cell lysate from cervical cancer cell lines, including HeLa cell line (HPV18 positive), SiHa cell line (HPV16 positive) and C33A cell line (non-HPV infected) were used to demonstrate detection of HPV E6, E7, or L1 by the HPV monoclonal antibody on western blot.

Figure 3:
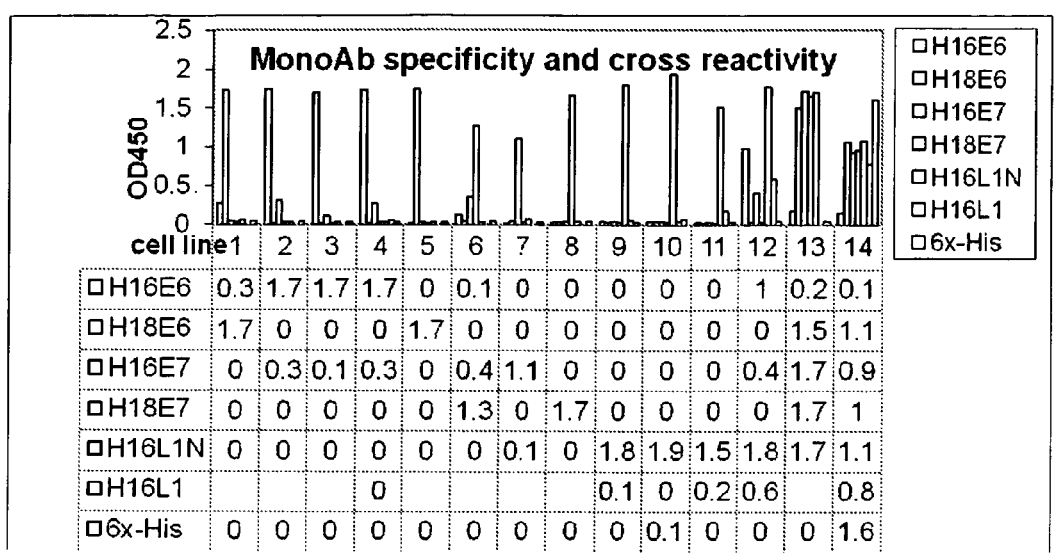
FIG. 3 illustrates cross reactivity of anti-HPV E6, anti-HPV E7, and anti-HPV L1 antibodies from various hybridoma clones (cell lines 1 to 14) to various HPV proteins as labeled in the legend according to one embodiment of the invention. 6×His was used as the negative control.

FIG. 3 shows the cross reactivity of anti-HPV E6, anti-HPV E7, and anti-L1 antibodies from various hybridoma clones to various HPV proteins. 6×His was used as the negative control. These data demonstrate the monoclonal antibodies described in this invention include HPV type-specific, and non-type specific clones capable of binding to HPV recombinant proteins.

Figure 4:
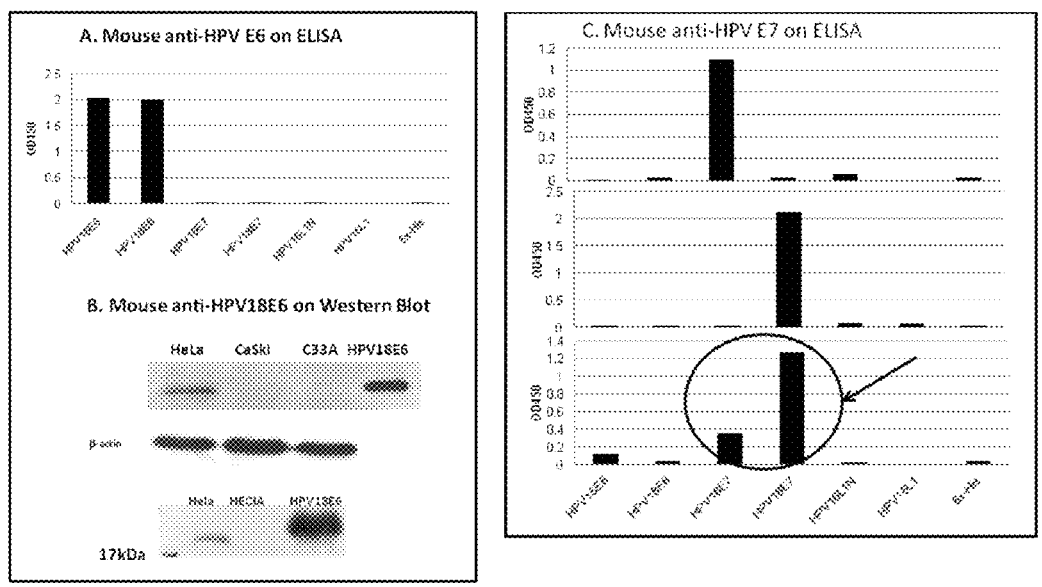
FIG. 4A provides an exemplary ELISA result using mouse monoclonal anti-HPV E6 antibody to detect various HPV proteins from various HPV types.
FIG. 4B provides an exemplary Western blot result using mouse monoclonal anti-HPV 18E6 antibody on various cell lines according.
FIG. 4C provides an exemplary ELISA result using mouse monoclonal anti-HPV E7 antibody to detect various HPV proteins from various HPV types.
Figure 5A:
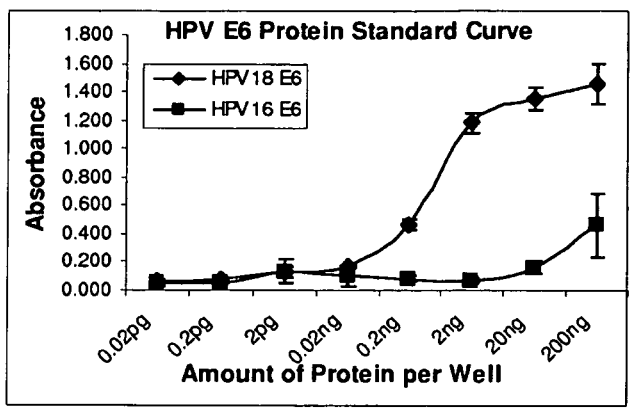
FIG. 5A provides an exemplary standard curve for HPV18 E6 recombinant protein and HPV16 E6 recombinant protein using a mouse monoclonal anti-E6 antibody by colorimetric method.
Figure 5B:
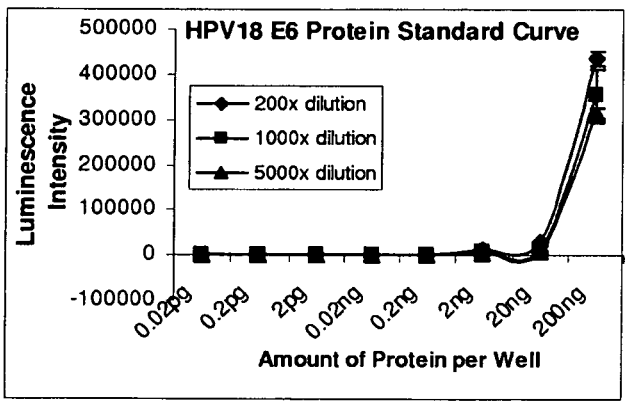
FIG. 5B provides an exemplary standard curve for HPV18 E6 protein with various dilutions of monoclonal anti-E6 antibody using luminescent method.
Figure 5C:
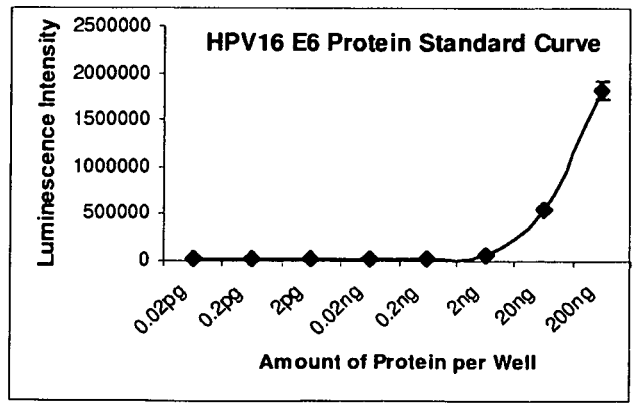
FIG. 5C provides an exemplary standard curve for HPV16 E6 protein detected by a mouse monoclonal anti-E6 antibody using luminescent method.
Figure 5D:
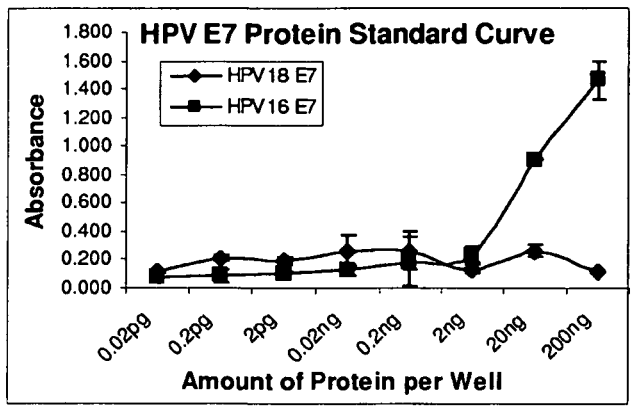
FIG. 5D provides an exemplary standard curve for HPV18 E7 and HPV16 E7 recombinant protein using a monoclonal anti-E7 antibody by colorimetric method.
Figure 5E:
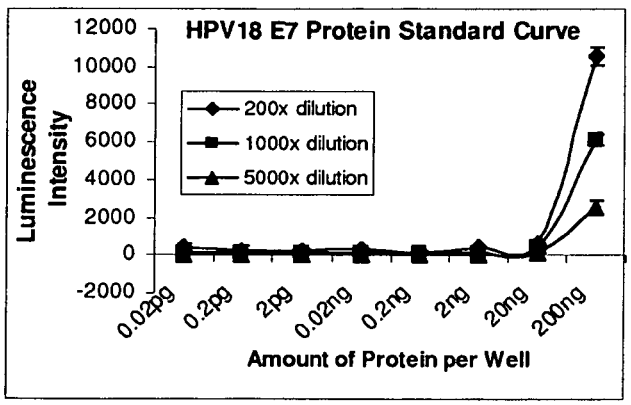
FIG. 5E provides an exemplary standard curve for HPV 18 E7 recombinant protein with various dilutions of a monoclonal anti-E7 antibody using luminescent method.
Figure 5F:
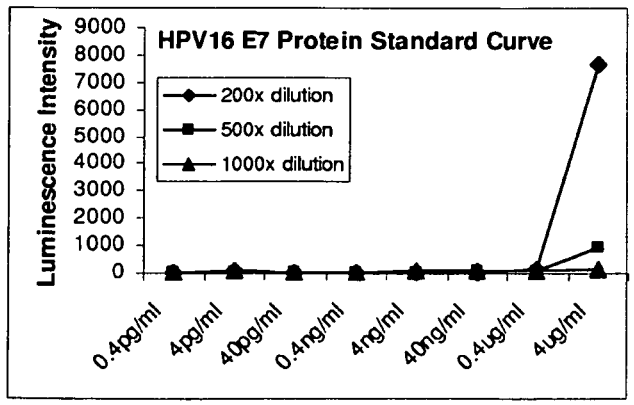
FIG. 5F provides an exemplary standard curve for HPV16 E7 recombinant protein detected by anti-E7 antibody using luminescent method.

FIG. 4A shows the ELISA results using mouse anti-HPV E6 antibody to detect various HPV proteins. Specific binding was obtained with HPV16E6 and HPV 18E6 proteins. FIG. 4B. Western blot results using mouse anti-HPV18E6 antibody on various cell lines. Positive stain was obtained on HPV18 infected HeLa cell lines. Recombinant HPV 18E6 protein was used as a positive control. Anti-beta actin antibody was used as an internal positive control. FIG. 4C. ELISA results using mouse anti-HPV E7 antibody to detect various HPV proteins. Specific binding was obtained with HPV16E7 and HPV18E7 proteins.

To demonstrate a monoclonal antibody capable of binding to tow or more HPV viral proteins from different HPV type as described in this invention, a monoclonal antibody capable of reacting with recombinant E6 proteins of HPV 16 and HPV18 was also obtained. FIG. 4A shows the specificity of a monoclonal antibody with common epitope capable of reacting with recombinant HPV16 E6 and HPV18E6 proteins on EIA. The recombinant protein coated on microtiter plate to be detected by the antibody described herein is in native form. These data demonstrate the monoclonal antibody reacts strongly to native form of recombinant HPV16 E6 and HPV18E6 proteins, but non-reactive to native form of recombinant HPV E7 nor HPV L1 proteins. These data indicate that this antibody contains HPV E6 common epitope capable of reacting with native form of recombinant HPV16 E6, and HPV18 E6 proteins. FIG. 4B shows the results of a Western blot using cell lysate from various cervical cancer cell lines to react with the same monoclonal antibody tested in FIG. 4A binding with recombinant E6 proteins of HPV 16 and HPV18. Both the cell lysate and recombinant proteins shown a single band as detected by the monoclonal antibody around the standard molecular weight marker of 17 kDa demonstrate the detection of HPV E6 protein (about 18 kDa) from cervical cancer cell line in HeLa (HPV18), but not C33A (non-HPV infection) cell line. The bands on the recombinant protein lanes shown with expected molecular weight indicate that the monoclonal antibody reacts strongly to denatured HPV18E6 recombinant proteins.

As another example to demonstrate a monoclonal antibody capable of binding to two or more HPV viral proteins from different HPV type as described in this invention, FIG. 4C (circled) shows the specificity of a monoclonal antibody capable of reacting with both recombinant HPV16 E7 and HPV18E7 protein on EIA. The recombinant protein coated on microtiter plate detected by the antibody described herein is in native form. These data demonstrate the monoclonal antibody described herein reacts strongly to native form of recombinant HPV16 E7 and HPV18 E7 proteins, but non-reactive to native form of recombinant HPV E6 nor HPV L1 proteins. These data indicate that this antibody contains HPV E7 common epitope capable of reacting with native form of HPV16 E7, and HPV18 E7 proteins.

To demonstrate a monoclonal antibody capable of binding to only a first HPV viral protein, but not a second HPV viral protein different from the first HPV viral protein, FIG. 4C ($1^{st}$ graph) shows the specificity of a monoclonal antibody capable of reacting with recombinant HPV16 E7 but not with other recombinant HPV proteins on EIA. Data indicate the specificity of this monoclonal antibody containing specific epitope is capable of reacting with HPV 16 E7 only, and does not cross-react with HPV 18 E7 or other recombinant HPV proteins on EIA. The recombinant protein coated on microtiter plate detected by the antibody described herein is in native form. These data demonstrate the monoclonal antibody described herein reacts strongly to native form of recombinant HPV16 E7 proteins, but does not cross-react to native form of recombinant HPV E6 or L1 proteins. These data also indicate that this antibody contains HPV16 E6 specific epitope capable of reacting with HPV16 E7 protein only. FIG. 4C ($2^{nd}$ graph) shows the specificity of a monoclonal antibody capable of reacting with recombinant HPV18 E7 but not with other recombinant HPV proteins on EIA.

Procedures described in Example 2 provide techniques to produce and characterize at least the monoclonal and polyclonal antibodies raised against at least the purified recombinant HPV 16 E6 protein, HPV 16 E7 protein, HPV 16 L1 protein, HPV 18 E6 protein, HPV18 E7 protein, HPV 18 L1 protein, and combinations thereof. Results described in Example 2 demonstrate the specific binding of these antibodies to at least the HPV 16 E6 protein, HPV 16 E7 protein, HPV 16 L1 protein, HPV 18 E6 protein, HPV18 E7 protein, HPV 18 L1 protein, and combinations thereof. Data demonstrate creation of pan antibodies, each one of which is capable of detecting HPV protein from at least two or HPV types.

Example 3

Detailed Procedures for Sample Collection and Preparation

Detailed procedures for sample collection and preparation for use in whole-cell ELISA assay described in the instant Application are described in this Example.

The samples used for whole-cell ELISA as described in various examples in the instant invention include but not limited to recombinant proteins, cultured cell lines and clinical samples.

The recombinant proteins used were obtained and characterized following the procedures provided in Example 1. The cultured cell lines used were obtained from in vitro cell culture constituents.

The clinical samples used were obtained from living human subjects. The human subjects from whom the sample was obtained falls to the following categories: 1. Healthy human subjects, from whom the samples was obtained during routine physical exams and used as a part of routine screening. 2. Human subjects who were susceptible to HPV, (e.g., as determined by family history; exposure to certain environmental factors; etc.). 3. Human subjects who had symptoms of abnormality (e.g., cervical warts, or the like). 4. Human subjects who have been provisionally diagnosed as having cervical disease (e.g. as determined by other tests based on, e.g., pap smears, hybrids capture, PCR tests, etc.).

The clinical samples used for whole-cell ELISA as described in various examples in the instant invention were derived from cervical scrapes obtained from the human subject. Samples as used herein thus include a material or mixture of materials, typically, although not necessarily, in fluid form, i.e., aqueous. All samples were taken from female patients during their scheduled visits for gynecological examinations. After inserting a speculum to a human subject, a brush or a cotton swab was inserted in the endocervix and rotated to obtain endocervical cells, i.e., the cervical scrapes. The brush or swab was then removed and immediately deposited to the preservative solutions. Various preservative solutions have been used, including but not limited to commercially available and clinically used ThinPrep© (Hologic, Inc.) preservative solution and SurePath© (BD Biosciences Inc.) preservative solution.

Example 4

Detailed Procedures for Whole-Cell ELISA Assay

Detailed procedures associated with various assay conditions used in whole-cell ELISA assay as described in the instant Application are described in this Example.

As an example, proteins, cells, or clinical samples (hereinafter sample) were used for the whole-cell ELISA assay. Samples can be directly deposited to the wells of microtiter plate or to a collection vial containing fixation and preservative agents in solution. Prior to the assay, samples have been used without any pre-treatment, or with various pre-treatments including but not limited to antigen retrieval procedures, cell condensation procedures, or combinations thereof.

Antigen retrieval procedures were performed by treating the samples in various buffered solutions at various temperatures for various time periods. The temperatures that have been used ranging from room temperature to 100° C. or higher, i.e. 120 C. The buffered solutions that have been used include high pH Tris buffer (pH=9-10) and low pH citrate buffer (pH=~6). The treating time that has been used ranging from 5 minutes to 45 minutes.

Cell condensation was performed using the following procedures. Sample in the collection liquid was centrifuged or allowed to sit without disturbance for 30 min to 2 hours for the cells to settle down on the bottom of the collection vial. Part of the supernatant was then removed to concentrate the sample.

After single treatment, combined treatment or no treatment, samples were dispensed to the surface of the container for the assay. Various surfaces used include but not limited to glass or plastic surfaces coated or treated for suitable binding specificity, for example, plastic surface treated for cells to bind, or plastic surface treated for protein to bind; glass or plastic surfaces with a thin layer of membrane attached. The surface can also be in a form of beads to maximize the contacting area. Each sample was loaded to a single container. Multiple containers were combined to form a format as a microtiter plate for high-throughput process.

After dispensing the samples to the surface of the container, the sample was immobilized on the surface. Various conditions for immobilization have been used. The immobilization was carried out allowing the samples to sit on the surface without disturbance. The immobilization time ranged from 10 minutes to 24 hours. The immobilization temperature ranged from 4° C. to 37° C.

After immobilization, the samples were fixed. Various conditions for fixation have been used. The fixation solutions used include 100% methanol, 100% ethanol and 100% acetone. The fixation time used ranged from immediate air-blow dry to 24 hours or until the fixation solution was completed evaporated without assistance. The fixation temperature used ranged from 4° C. to room temperature to.

After fixation, the samples were permeabilized to destruct the cell membrane for the antibody get into the cells to allow the accessibility of the antibody binding to the antigen intracellularly. Various permeabilization agents have been used, including but not limited alcohol based solution such as chilled (−20° C.) 90% methanol in deionized $H_2O$, and detergent based solution such as saponin, triton, NP-40, tween-20, and digitonin Various concentrations for each detergent-based permeabilization agent have been used (all diluted with deionized $H_2O$): 0.1% to 5% for NP40, 0.1% to 2.5% for tween-20, 0.001% to 0.5% for saponin, 0.1% to 2.5% for digitonin, and 0.01% to 1% for triton. Various temperatures for permeabilization have been used, from room temperature to 0° C. Various permeabilization time have been used, from 5 minutes to 30 minutes. Incubation was carried out under gentle shaking.

Washing solution was used along the assay procedures; in general before the addition of a new solution for the purpose of eliminate the residual solution from the previous step. Various washing solutions have been used, including deionized water, phosphate buffer saline, and phosphate buffer saline containing tween-20. Various concentrations of tween-20 have been used, ranging from 0.1% to 1%. Various washing time have been used, ranging from immediate disposal to 5 minutes. Washing procedures have been performed allowing the samples to incubate without disturbance, or with gentle shaking. Washing procedure has been used for 2 to 4 repeats.

After permeabilization, the solution in the container was disposed. The samples were washed with the washing solution. The samples were then incubated with 3% $H_2O_2$ to block endogenous hydrogen peroxidase that may otherwise cause increased background signal. The 3% $H_2O_2$ solution has been prepared using deionized $H_2O$, 100% methanol or phosphate buffer saline. The incubation time has been used ranging from 10 minutes to 30 minutes. After incubation, the solution in the container was disposed and the samples were washed.

The samples were then incubated in the blocking solution to block the non-specific binding site on the samples and the surface to eliminate non-specific binding. Various blocking conditions have been used. Blocking solutions that have been used includes normal goat serum, casein buffer, and commercially available assay diluents and assay buffer. Incubation time that has been used ranging from 1 hour to 24 hours. Blocking temperatures that have been used include room temperature and 4° C. Incubation was carried out under gentle shaking. The blocking solution was disposed after incubation.

Primary antibody that binds to the recombinant protein or the protein of interest that is expressed in the sample was added to the samples. Various conditions have been performed. Various polyclonal or monoclonal anti-HPV E6 or anti-HPV E7 antibodies have been used. Various dilutions of the antibodies have been used, ranging from 1:50 dilution to 1:1000 dilution. Various diluents have been used, including 10% normal goat serum, casein buffer and assay diluents. Various incubation time lengths have been performed, ranging from 1 hour to 24 hours. Various incubation temperatures have been performed, including room temperature and 4° C. Incubation was carried out under gentle shaking. The primary antibody solution was disposed after incubation. The samples were washed with the washing solution.

Secondary antibody that binds to the primary antibody was added to the samples. Various conditions have been performed. Various secondary antibodies have been used, including antibodies conjugated with biotin or horse radish peroxidase (HRP). Various dilutions of the secondary antibodies have been used, ranging from 1:125 to 1:1000 dilutions for the biotinylated antibodies, and 1:125 to 1:250 for the HRP-conjugated antibodies. Various diluents haven used, including phosphate buffer saline, normal goat serum, casein buffer, and commercially available assay diluents. Various incubation times have been performed, ranging from 30 minutes to 1 hour. Incubation was carried out under gentle shaking. The secondary antibody solution was disposed after incubation. The samples were washed with the washing solution.

If the biotinylated secondary antibody was used, the samples were then incubated with streptavidin conjugated HRP solution. Various incubation conditions have been performed. Various dilutions of the HRP solutions have been performed, ranging from 1:250 to 1:600 dilutions. Various incubation times have been performed, ranging from 45 minutes to one hour. Various diluents haven used, including phosphate buffer saline, normal goat serum, casein buffer, and commercially available assay diluents. Incubation was carried out under gentle shaking. After incubation, the solution was disposed. The samples were washed with the washing solution.

Substrate suitable for the readout of the signal intensity that represents the binding of antibody to target protein in the sample was added to the sample to obtain the measurement of the quantity of the protein or the protein expressed in the sample. Various substrates have been used. All the substrates are commercially available and preparation of the substrates was according to the instruction provided. Incubation was carried out under gentle shaking.

For colorimetric technique, TMB ELISA substrate or its equivalence was used to detect horseradish peroxidase activity that arises from the binding of the antibody to the protein. Upon the addition of TMB to the sample, it yields a blue color that changes to yellow upon addition of acid stop solution (Max absorbance at 450 nm). The signal intensity was read using colorimetric plate reader.

For chemiluminescent technique, commercially available chemiluminescent substrate was used to detect horseradish peroxidase activity that arises from the binding of the antibody to the protein. Upon the addition of the substrate to the sample, chemiluminescent intensity was read using chemiluminescent plate reader.

For fluorescent technique, commercially available fluorescent substrate was used to detect horseradish peroxidase activity that arises from the binding of the antibody to the protein. Upon the addition of the substrate to the sample, fluorescent intensity was read using fluorescent plate reader.

Example 5

Whole-Cell ELISA Assay Performed on Cultured Cells

To demonstrate the feasibility of the whole-cell ELISA assay described in the instant Application, assay procedures as described in Example 4 was applied to cultured cells, with which the cell population and cell number is more uniformed.

As an example, whole cell ELISA was performed using anti-HPV E7 antibody to detect the expression level of HPV E7 oncoprotein in HPV positive cell line Hela and HPV negative cell line C33a. Hela cells and C33a cells were obtained from cell culture constituents. Various concentrations of the cell culture solution was prepared: approximately 9000 Hela cells, 4500 Hela cells, 40000 C33a cells and 20000 C33a cells per 50 μL. Duplicates of 50 μl of each concentration of each cell line were dispensed to the clear, polystyrene coated, flat bottom and high binding 96-well microtiter plate. Cells were immobilized for 30 minutes at room temperature. After immobilization the solution was disposed, and the cells were fixed using 25 μL of 100% ethanol with immediate air-blow dry at room temperature. After fixation, the cells were permeabilized with 100 μl of chilled (−20° C.) 90% methanol in deionized water for 5 minutes at room temperature with gentle shaking. After permeabilization, the solution in the container was disposed and the cells were washed with phosphate buffer saline for 2 times of 5 minutes under gentle shaking. 100 μl of 3% $H_2O_2$ were added to the sample and incubated for 20 minutes at room temperature with gentle shaking to block endogenous hydrogen peroxidase. After the incubation was completed, the solution was disposed and the cells were washed three times of 5 minutes each time with gentle shaking. The cells were then incubated in 100 μl of 10% normal goat serum for one hour at room temperature with gentle shaking for blocking the non-specific binding site on the samples and the surface of the microtiter plate to eliminate non-specific binding. 50 μl of the anti-HPV E7 antibody were used in 1:200 dilution in 10% normal goat serum to incubate the samples for 1 hour under room temperature with gentle shaking. After the incubation was completed, the solution was disposed and the samples were washed with PBS washing solution for 3 times of 5 minutes each under gentle shaking. 50 μl of the biotinylated secondary antibody was then added using 1:500 dilution in 5% normal goat serum and incubated the samples for 30 minutes under room temperature with gentle shaking. After the incubation was completed, the solution was disposed and the samples were washed with PBS washing solution for 3 times of 5 minutes each under gentle shaking. 50 μl of the streptavidin conjugated HRP solution was then added using 1:600 dilution in PBS and incubated the samples for 45 minutes under room temperature with gentle shaking. After the incubation was completed, the solution was disposed and the samples were washed with PBS washing solution for 3 times of 5 minutes each under gentle shaking. 50 μl of TMB substrate was then added to incubate the sample under room temperature without disturbance for 10 minutes. 25 μl of the acid stop solution was then added to stop the enzymatic reaction and the signal intensity was read out using colorimetric plate reader. The assay was repeated for at least 2 times to confirm reproducibility. Whole cell ELISA results are shown in FIG. 6A.

Figure 6A:
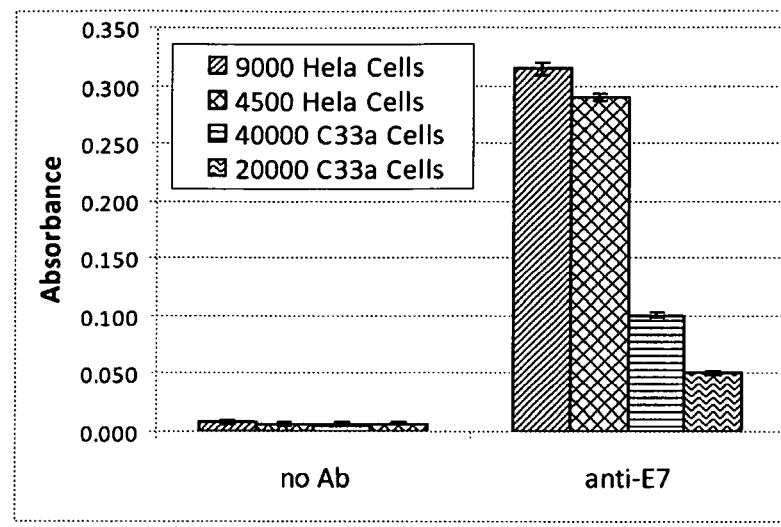
FIG. 6A provides exemplary whole-cell ELISA results with and without anti-HPV E7 antibody showing averaged absorbance of HPV whole-cell ELISA for cervical cancer cell lines.

FIG. 6A shows the averaged absorbance for cell lines without normalization with and without anti-HPV E7 antibody. Each reading corresponds to total cells in the ELISA well and the cell numbers are shown in the legend. Signal intensity for the HPV-positive HeLa cells is significantly higher than that for the HPV-negative C33a cells, despite the fact that a significant higher amount of HPV-negative C33a cells were loaded. Assay performed with no primary antibody was used as a negative control. Negligible signal intensity was produced.

Figure 6B:
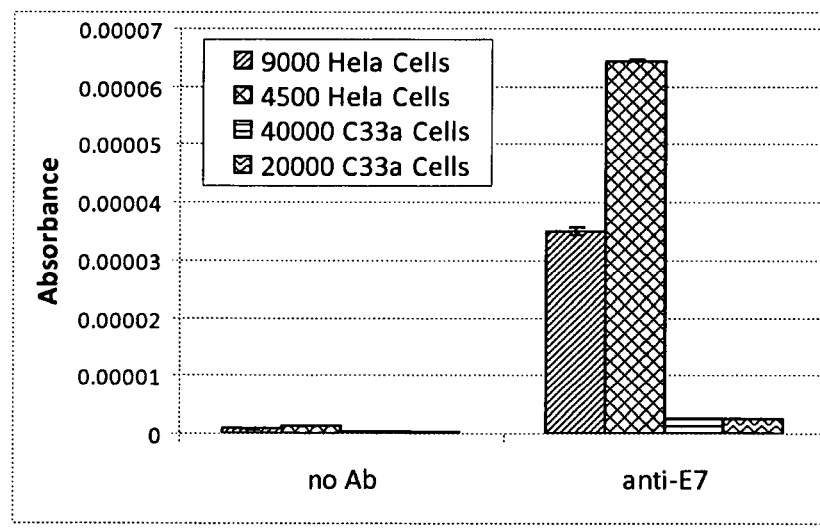
FIG. 6B provides exemplary whole-cell ELISA results with and without anti-HPV E7 antibody for cervical cancer cell lines showing averaged absorbance from FIG. 6A and normalized to intensity per cell for HPV positive Hela cells and HPV negative C33a cells.

Normalization was performed and the data is shown in FIG. 6B. Averaged absorbance for HPV positive Hela cells and HPV negative C33a cells with and without anti-HPV E7 antibody. The reading is normalized and corresponds to the absorbance per cell. The difference in signal intensity between the HPV-positive HeLa cells and the HPV-negative C33a cells further increased as compared to the data shown in FIG. 6A without normalization.

As another example, whole-cell ELISA assay was performed using various concentrations of the HPV-positive HeLa cells and the HPV-negative C33a cells. Concentrations for Hela cells used are 1250 cells, 2500 cells, 3750 cells and 5000 cells per 50 μl. Concentrations for C33a cells used are 2500 cells, 5000 cells, 10000 cells, and 20000 cells per 50 μl. The same assay procedures as described in [0203] were used. Anti-HPV E7 antibody was used with a dilution of 1:200 in 10% normal goat serum. The assay was repeated for at least 2 times to confirm reproducibility. The data generated was plotted to generate a titration curve for both HeLa and C33a cells.

Figure 6C:
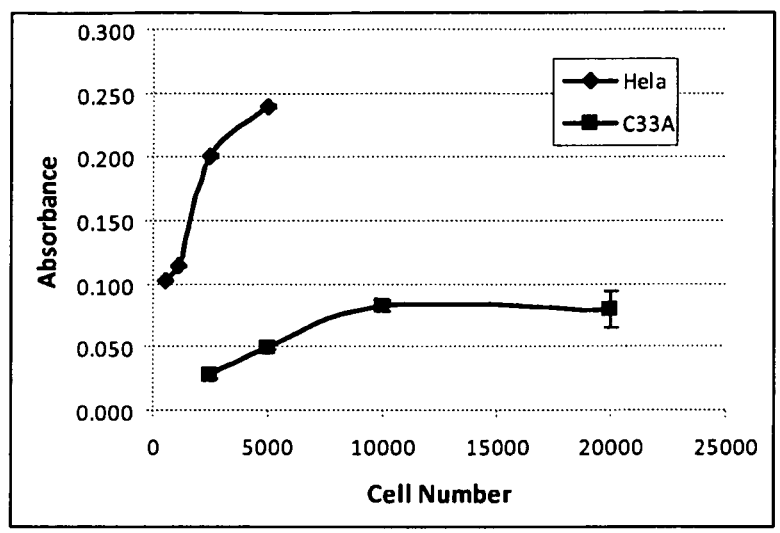
FIG. 6C provides exemplary titration curves for HPV positive Hela cells and HPV negative C33a cells on whole-cell ELISA using an anti-HPV E7 antibody and colorimetric absorbance detection method.

FIG. 6C shows the titration curves for HPV positive Hela cells (diamond dots) and HPV negative C33a cells (square dots) against anti-HPV E7 antibody using colorimetric method measuring absorbance without cell number normalization. Readings present corresponding to the average reading per ELISA well. The difference in absorbance between the HPV-positive and HPV-negative cell lines occurs when 5000 cells were used for the assay. Signal intensity for C33a saturated when using higher cell numbers beyond 10000 cells per well, indicating that the cells loaded to the surface of the container were likely over-saturated.

Figure 6D:
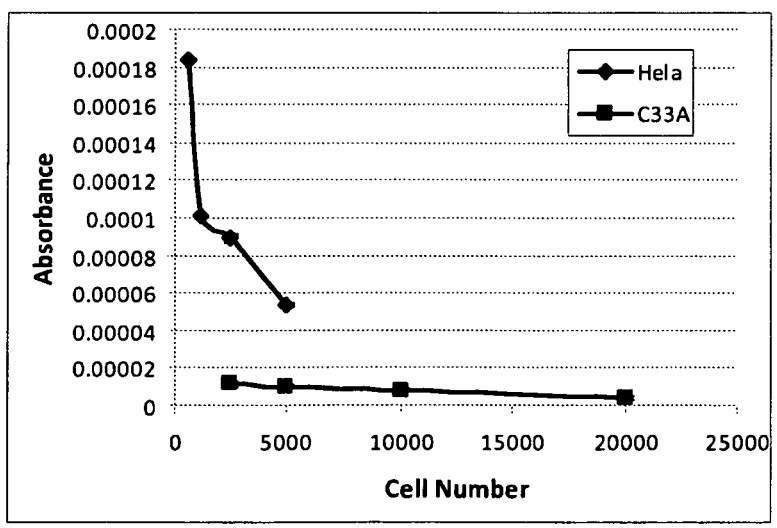
FIG. 6D illustrates normalized intensity per cell based on FIG. 6C titration curves for HPV positive Hela cells and HPV negative C33a cells.

Cell number normalization was performed and the results are shown in FIG. 6D. Titration curves for HPV positive Hela cells (diamond dots) and HPV negative C33a cells (square dots) using colorimetric method measuring absorbance. Readings from FIG. 6C are normalized based on the cell numbers thus corresponding to the average reading per cell. Data for HPV-positive HeLa cells shows that signal intensity was optimal when the amount of cells used for the assay was not too high. Data for HPV-negative C33A cells shows that regardless of the amount of cells used for the assay, signal intensity retains minimal, confirming that this particular cell line is HPV-negative.

As another example, whole-cell ELISA assay was performed using anti-HPV E6 antibody to detect the expression level of HPV E6 oncoprotein in clinical cancer samples, cultured HPV-positive HeLa and SiHa cells, and HPV-negative C33a cells using the similar procedures as described in [0203]. Clinical cancer samples were used as is, i.e., as collected in the collection solution without cell number normalization and the collection liquid is SurePath® preservative solution. Concentrations for all three cultured cell lines used are 36000 cells, 27000 cells, 1800 cells and 9000 cells per 50 μl. Anti-HPV E6 antibody was used with a dilution of 1:200 in 10% normal goat serum. The assay was repeated for at least 2 times to confirm reproducibility. The data generated was plotted to show the relative absorption intensity as presented in FIG. 6E.

Figure 6E:
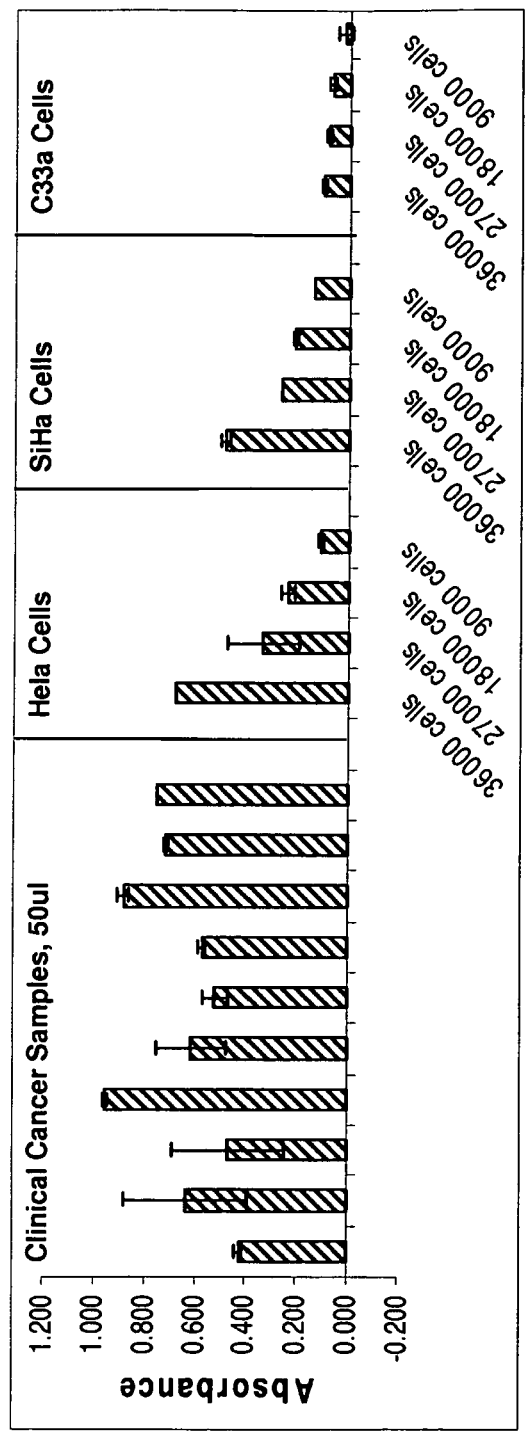
FIG. 6E. provides exemplary whole-cell ELISA results showing absorbance from cell-based ELISA experiments using a mouse monoclonal anti-HPV E6 antibody detecting HPV E6 oncoprotein present in clinical cancer samples, HPV positive Hela cells and SiHa cells, and but not in HPV negative C33a cells.

FIG. 6E shows the absorbance obtained from whole-cell ELISA assay using anti-HPV E6 antibody for HPV E6 antigen capture for clinical cancer samples, HPV positive Hela cells and SiHa cells, and HPV negative C33a cells. Clinical cancer samples show high absorbent signals. Intensities of absorbance for HPV positive Hela and SiHa cells are in proportional to the cells number. 36000 HeLa or SiHa cells gave comparable signal intensity to what obtained for the clinical cancer samples. Intensities of HPV negative C33a cells are low.

Altogether, data provided in this example as shown in FIG. 6 demonstrate that whole-cell ELISA assay using anti-HPV E6 or anti-HPV E7 antibody allows the detection of the expression level of HPV E6 or HPV E7 oncoproteins in cultured cells and clinical cancer samples. Specific binding of one or more anti-HPV antibodies raised against purified recombinant HPV proteins to an HPV protein expressed by an HPV-infected cell was detected. The level of an HPV protein expression by an HPV-infected cell was detected and quantified based on absorption signal intensity. The quantified expression level of an HPV protein expressed by an HPV-infected cell was normalized based on the measured cell numbers in the cultured cell samples used in the whole-cell ELISA assay.

Example 6

Detection of HPV Oncoprotein Expression Level in Clinical Samples Using Whole-Cell ELISA Assay To demonstrate that the whole-cell ELISA assay can be used for screening and diagnosis of HPV-associated infections, whole-cell ELISA assay was performed on various groups of clinical cytology samples, including clinical cytology samples with histology diagnosis, blind clinical cytology samples without histology diagnosis, cervical cancer samples, and normal cervical cytology samples. These clinical cytology samples were either in ThinPrep® preservative solution or SurePath® preservative solution.

Figure 7:
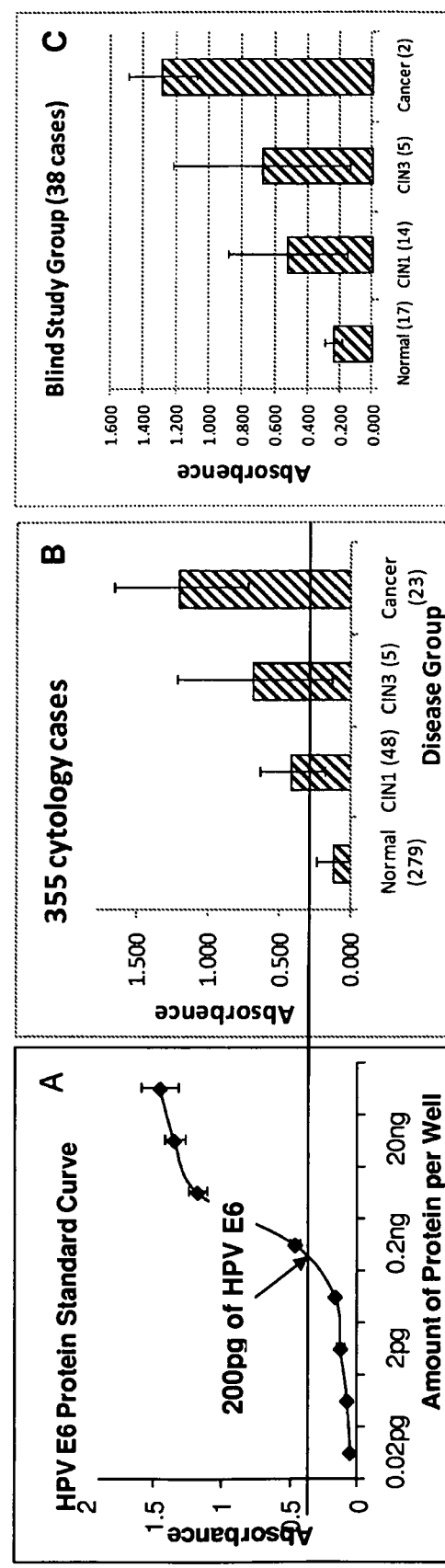
FIG. 7A provides an exemplary standard curve for HPV18 E6 recombinant protein using monoclonal anti-E6 antibody by colorimetric method.
FIG. 7B provides an exemplary bar graph of HPV whole-cell ELISA results using the same monoclonal anti-E6 antibody used in FIG. 7A to detect HPV E6 oncoprotein present in clinical samples for total 355 clinical cytology samples.
FIG. 7C shows results of a blind study with 38 cases of clinical samples tested on HPV whole-cell ELISA using the same monoclonal anti-HPV E6 monoclonal antibody used in FIGS. 7A and 7B.

As an example, whole cell ELISA was performed using anti-HPV E6 antibody to detect the expression level of HPV E6 oncoprotein in clinical samples. Total 355 clinical cytology samples were used. Duplicates of 50 µl of each sample were dispensed to the clear, polystyrene coated, flat bottom and high binding 96-well microtiter plate. Cells were immobilized for 30 minutes at room temperature. After immobilization the solution was disposed, and the cells were fixed using 25 µL of 100% ethanol with immediate air-blow dry at room temperature. After fixation, the cells were permeabilized with 100 µl of chilled (−20° C.) 90% methanol in deionized water for 5 minutes at room temperature with gentle shaking. After permeabilization, the solution in the container was disposed and the cells were washed with phosphate buffer saline for 2 times of 5 minutes under gentle shaking. 100 µl of 3% $H_2O_2$ were added to the sample and incubated for 20 minutes at room temperature with gentle shaking to block endogenous hydrogen peroxidase. After the incubation was completed, the solution was disposed and the cells were washed three times of 5 minutes each time with gentle shaking. The cells were then incubated in 100 µl of 10% normal goat serum for one hour at room temperature with gentle shaking for blocking the non-specific binding site on the samples and the surface of the microtiter plate to eliminate non-specific binding. 50 µl of the anti-HPV E6 antibody were used in 1:200 dilution in 10% normal goat serum to incubate the samples for 1 hour under room temperature with gentle shaking. After the incubation was completed, the solution was disposed and the samples were washed with PBS washing solution for 3 times of 5 minutes each under gentle shaking. 50 µl of the biotinylated secondary antibody was then added using 1:500 dilution in 5% normal goat serum and incubated the samples for 30 minutes under room temperature with gentle shaking. After the incubation was completed, the solution was disposed and the samples were washed with PBS washing solution for 3 times of 5 minutes each under gentle shaking. 50 µl of the streptavidin conjugated HRP solution was then added using 1:600 dilution in PBS and incubated the samples for 45 minutes under room temperature with gentle shaking. After the incubation was completed, the solution was disposed and the samples were washed with PBS washing solution for 3 times of 5 minutes each under gentle shaking. 50 µl of TMB substrate was then added to incubate the sample under room temperature without disturbance for 10 minutes. 25 µl of the acid stop solution was then added to stop the enzymatic reaction and the signal intensity was read out using colorimetric plate reader. The assay was repeated for at least 2 times to ensure data quality and reproducibility. Whole cell ELISA results are shown in FIG. 7.

FIG. 7A. Standard curve of the average absorption intensity obtained from whole cell absorbance ELISA using anti-HPV E6 monoclonal antibody to measure the expression level of recombinant HPV E6 proteins. FIG. 7B. Average absorption intensity obtained from 355 clinical samples. Bars are shown with standard deviation as the error bars for clinical cytology samples (sample number=355) grouped by histology stages: 279 normal samples, 48 CIN1 samples, 5 CIN3 samples and 23 cervical cancer samples. The expression level of HPV E6 protein can be estimated by corresponding to the HPV E6 protein standard curve as described in FIG. 5 (shown again as FIG. 7A). Out of the 355 clinical cytology samples, 38 samples were blind cytology samples with no result regarding their histology stages. Data for these 38 samples are shown in FIG. 7C. In FIG. 7C, bar graphs of one blind study (right panel) and combined total study (right panel) showing the average absorption intensity obtained from whole cell absorbance ELISA using anti-HPV E6 monoclonal antibody to measure the expression level of HPV E6 proteins. Bars are shown with standard deviation as the error bars for clinical cytology samples. Graph at left shows one representative blind study with 17 normal (WNL), 14 CIN1, 5 CIN3 and 2 cancer (SCC) samples. A cutoff threshold was set at 0.341 to estimate the expression level of HPV E6 in order to determine the positive rate of the assay, and to determine the infection stage of the sample. Results from both graphs are comparable, demonstrating that using the whole cell absorbance ELISA as described in the Application generates reproducible data. By comparing with the titration curve (FIG. 7A, top left panel) and these data can be used for screening and for determining the infection stage of the clinical samples.

Whole-cell ELISA data obtained with the 355 clinical samples can be plotted as a histogram to show the individual absorption intensity and the distribution of these signal intensity. FIG. 8A is a histogram showing the individual absorption intensity for each clinical sample obtained from whole cell absorbance ELISA using anti-HPV E6 monoclonal antibody to measure the expression level of HPV E6 proteins. There are total 279 normal, 48 CIN1, 5 CIN3, and 23 cervical cancer (CxCa) samples in the study. The data demonstrate that the whole cell absorbent ELISA as described in the Application, can differentiate clinical cases with different cervical disease grades based on their absorbance intensity that represent the expression level of HPV E6 protein. Statistical analysis was performed on the data obtained using clinical samples, as shown in FIG. 8B. FIG. 8B shows the summary of the ROC curve (receiver operating characteristic) obtained by analyzing total of 355 cytology samples. ROC analysis is a correlation plot of the true positive rate, or sensitivity and the false positive rate, or 1-specificity. This analysis provides a tool to select possibly optimal models and to discard suboptimal ones independently from the class distribution. This figure is generated with 1-sensitivity as the y-axis and specificity as the x-axis. The large space on the right bottom corner indicates that the model chosen in this study provide high sensitivity and high specificity. The value of RA (ROC area) in the table indicates the test performance, i.e. RA≥0.9 is excellent, 0.9>RA≥0.8, is good, etc. Our ROC analysis results gives a large space on the right bottom indicate that this instant example of study has very high sensitivity and high specificity.

As another example, whole cell ELISA was performed using anti-HPV L1 antibody to detect the expression level of HPV E6 oncoprotein in clinical samples. Using the same procedure as described in [0214], total of 82 clinical samples were tested. Representative data is summarized in Table 3.

TABLE 3

Examples of ELISA test results of representative clinical samples using anti-HPV L1 antibody.

| Sample ID | Pap Diagnosis | HPV L1 ELISA OD | HPV E6 ELISA OD | HPV E7 ELISA OD |
|---|---|---|---|---|
| OH001 | HSIL | 0.392 | 0.157 | 0.191 |
| OH002 | HSIL | 0.389 | 0.164 | 0.392 |
| OH003 | HSIL | 0.398 | 1.333 | 0.069 |
| OH004 | HSIL | 0.806 | 1.718 | 0.397 |
| OH005 | HSIL | 0.484 | 1.633 | 0.167 |
| OH006 | HSIL | 0.730 | 0.792 | 0.196 |
| OH007 | HSIL | 0.702 | 1.939 | 0.438 |
| OH008 | HSIL | 0.327 | 0.017 | 0.149 |
| OH009 | HSIL | 0.381 | 0.033 | 0.206 |
| OH010 | HSIL | 0.385 | 0.953 | 0.000 |
| OH011 | HSIL | 0.432 | 1.607 | 0.082 |
| OH012 | HSIL | 0.583 | 1.547 | 0.201 |
| OH013 | Negative | 0.019 | 0.144 | 0.000 |
| OH014 | Negative | 0.081 | 0.086 | 0.044 |
| OH015 | Negative | 0.005 | 0.005 | 0.068 |
| OH016 | Negative | 0.023 | 0.000 | 0.004 |
| OH017 | Negative | 0.008 | 0.011 | 0.027 |

The procedures described in this Example demonstrate the feasibility of the whole-cell ELISA assay described in the instant Application on clinical samples that comprise a population of fixed cells susceptible to infection by a HPV. The results provided in this Example demonstrate that specific binding of one or more anti-HPV antibodies raised against purified recombinant HPV proteins to an HPV protein expressed by an HPV-infected cell under conditions that promote specific binding of the antibody to an HPV protein expressed by the population of cells from the clinical samples was detected. The level of an HPV protein expression by an HPV-infected cell was detected and quantified based on absorption signal intensity. The quantified expression level of an HPV protein expressed by an HPV-infected cell was compared to a predetermined HPV protein express level threshold and to an HPV protein standard curve. The predetermined HPV protein expression level threshold is associated with a cancer or a pathological stage of transformation in the clinical sample. The HPV types detected in the total 355 cases include type 8, 16, 18, 33, 35 and 69, as summarized in Table 4. These data demonstrate the pan antibody used in the whole-cell ELISA described herein is capable of detecting HPV oncoproteins from clinical samples with most high-risk types of HPV infection.

TABLE 4

Examples of ELISA test results of representative clinical samples correlating to HPV genotype.

| Sample ID | HPV Test | HPV Typing | Pap Diagnosis | HPV E6 ELISA OD |
|---|---|---|---|---|
| OH021 | positive | 18, 58 | WNL | 1.029 |
| OH022 | positive | 16 | CIN 1 | 0.391 |
| OH023 | positive | 53 | CIN 1 | 0.900 |
| OH024 | positive | 58 | CIN 3 | 0.467 |
| OH025 | positive | 16 | Ca-SCC | 1.028 |
| OH026 | positive | 16 | Ca-SCC | 0.654 |
| OH027 | positive | 18 | Ca-SCC | 1.472 |
| OH028 | positive | 33 | Ca-SCC | 1.240 |
| OH029 | positive | 16 | Ca-SCC | 1.703 |
| OH030 | negative | negative | WNL | 0.086 |
| OH031 | negative | negative | WNL | 0.093 |

Example 7

Normalization of Whole-Cell ELISA Data

Various methods to normalization of cell density in clinical samples used for the whole-cell ELISA assay described in the instant Application.

Example 7.1

Cellularity normalization before assay: normalizing cell density in the clinical samples before the assay to allow the samples loaded on each well of microtiter plate for ELISA assay contain about the same level of cell density. It was performed according to the following procedures. Individual sample in the collection liquid was allowed to sit without disturbance for at least 30 min to 2 hours for the cells to settle down on the bottom of the collection vial. The volume of the cell pallet was measured and the density of the cells, i.e., the cellularity of the sample, was obtained by calculating the ratio of the pallet volume (µl) to the total volume of the solution (ml). Normalization was performed by concentrating or diluting the samples to bring their cellularity to the same. As an example, samples upon normalization have the same cellularity. As another example, samples with cellularity of 25 or above were used as it is. Samples with cellularity lower than 25 were normalized to bring the cellularity to 25.

TABLE 5

Example of cell density measurements and normalization of the cell density in clinical samples.

| Sample ID | Cell Pellet Vol. (µl) | Sample Solution Vol. (ml) | Cell Density (Cellularity) | Normalization Factor | Solution Removed (ml) | Normalized Cell Density |
|---|---|---|---|---|---|---|
| OH041 | 50 | 12.5 | 4.0 | 6.3 | 10.5 | 25 |
| OH042 | 50 | 12 | 4.2 | 6.0 | 10.0 | 25 |
| OH043 | 100 | 13 | 7.7 | 3.3 | 9.0 | 25 |
| OH044 | 50 | 12.5 | 4.0 | 6.3 | 10.5 | 25 |
| OH045 | 100 | 7 | 14.3 | 1.8 | 3.0 | 25 |
| OH046 | 25 | 12 | 2.1 | 12.0 | 11.0 | 25 |
| OH047 | 25 | 11 | 2.3 | 11.0 | 10.0 | 25 |
| OH048 | 25 | 13.5 | 1.9 | 13.5 | 12.5 | 25 |
| OH049 | 250 | 12.5 | 20.0 | 1.3 | 2.5 | 25 |
| OH050 | 600 | 14.5 | 41.4 | 1 | 0 | 41.4 |

Example 7.2

Cell number normalization using housekeeping genes as internal positive controls: as an example, anti-β-actin was used as the internal positive control to reference the cell numbers deposited in the surface of the container. Actins are highly conserved proteins that are involved in cell motility, structure and integrity. β-actin antibody has been widely used as loading controls in immunoassays as it has been identified to remain the same proportion of total cell protein. Normalization using anti-β-actin was performed according to the following procedures. Duplicate samples were loaded on the surface in the container, and the assay was performed using the same assay procedures as described in Example 4. Upon the completion of blocking procedures, one set of the duplicate samples were incubated with the anti-HPV primary antibody, while the other set of the duplicate samples were incubated with anti-β-actin antibody. After the completion of the incubation, the rest of the assay procedures were carried out for both duplicates. Various conditions for anti-β-actin antibody incubation have been performed. Various dilutions of the anti-β-actin antibody have been used, ranging from 1:50 to 1:400 dilutions. Various incubation times have been used, ranging from 1 hour to 24 hours. Various incubation temperatures have been used, ranging from room temperature to 4° C.

As an example, whole cell ELISA was performed using anti-β actin antibody to detect the expression level of β-actin protein in HPV positive cell line Hela and HPV negative cell line C33a. Hela cells and C33a cells were obtained from cell culture constituents. Various concentrations of the cell culture solution was prepared to be approximately 1250 cells, 2500 cells, 5000 cells and 10000 cells per 50 µL. Duplicates of 50 µl of each concentration of each cell line were dispensed to the clear, polystyrene coated, flat bottom and high binding 96-well microtiter plate. Cells were immobilized for 30 minutes at room temperature. After immobilization the solution was disposed, and the cells were fixed using 25 µL of 100% ethanol with immediate air-blow dry at room temperature. After fixation, the cells were permeabilized with 100 µl of chilled (−20° C.) 90% methanol in deionized water for 5 minutes at room temperature with gentle shaking. After permeabilization, the solution in the container was disposed and the cells were washed with phosphate buffer saline for 2 times of 5 minutes under gentle shaking. 100 µl of 3% $H_2O_2$ were added to the sample and incubated for 20 minutes at room temperature with gentle shaking to block endogenous hydrogen peroxidase. After the incubation was completed, the solution was disposed and the cells were washed three times of 5 minutes each time with gentle shaking. The cells were then incubated in 100 µl of 10% normal goat serum for one hour at room temperature with gentle shaking for blocking the non-specific binding site on the samples and the surface of the microtiter plate to eliminate non-specific binding. 50 µl of the anti-β actin antibody were used in 1:200 dilution and 1:400 dilution in 10% normal goat serum to incubate the samples for 1 hour under room temperature with gentle shaking. After the incubation was completed, the solution was disposed and the samples were washed with PBS washing solution for 3 times of 5 minutes each under gentle shaking. 50 µl of the biotinylated secondary antibody was then added using 1:500 dilution in 5% normal goat serum and incubated the samples for 30 minutes under room temperature with gentle shaking. After the incubation was completed, the solution was disposed and the samples were washed with PBS washing solution for 3 times of 5 minutes each under gentle shaking. 50 µl of the streptavidin conjugated HRP solution was then added using 1:600 dilution in PBS and incubated the samples for 45 minutes under room temperature with gentle shaking. After the incubation was completed, the solution was disposed and the samples were washed with PBS washing solution for 3 times of 5 minutes each under gentle shaking. 50 µl of TMB substrate was then added to incubate the sample under room temperature without disturbance for 10 minutes. 25 µl of the acid stop solution was then added to stop the enzymatic reaction and the signal intensity was read out using colorimetric plate reader. The assay was repeated for at least 2 times to ensure data quality and reproducibility. Whole cell ELISA results are shown in FIG. 9A.

Figure 9A:
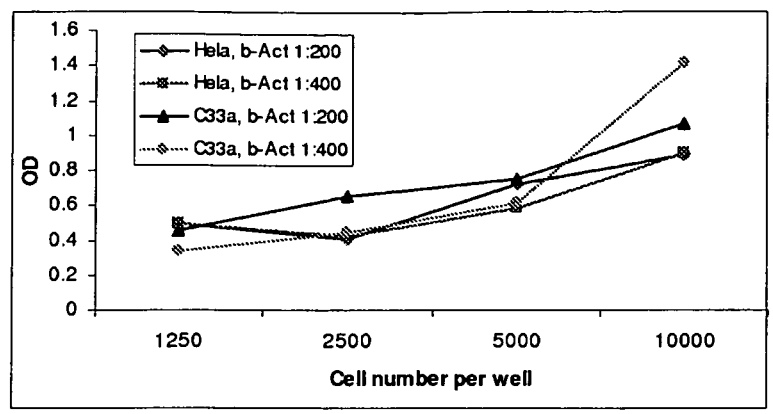

FIG. 9A shows the Absorption intensity (OD) for cell lines obtained from whole cell ELISA using anti-β actin antibody to detect the expression level of β-actin protein in HPV positive cell line Hela (diamond and square dots) and HPV negative cell line C33a (triangle and circle dots). The results show that the absorption intensity increases with the number of cells loaded in the microtiter plate wells regardless whether it is an HPV positive or negative cell line. Different concentration of the β-actin antibody has also been tested. 200 and 400 dilutions provided minimum difference in absorption intensity for fixed amount of cells loaded in the wells. The results indicated that β-actin can be used as a standard to quantify the amount of cells immobilized in the microtiter wells in the whole cell ELISA as described in the Application.

As another example, whole cell ELISA was performed using anti-HPV E6 antibody and anti-β actin antibody in parallel to detect the expression level of HPV E6 oncoprotein and β-actin protein in HPV positive cell line Hela and HPV negative cell line C33a for a side-by-side comparison. Hela cells and C33a cells were obtained from cell culture constituents. Cells from cultured cell lines were counted and prepared to be approximately 7500 cells per 50 µL. Two sets of duplicates of 50 µl of each concentration of each cell line were dispensed to the clear, polystyrene coated, flat bottom and high binding 96-well microtiter plate. Cells were immobilized for 30 minutes at room temperature. After immobilization the solution was disposed, and the cells were fixed using 25 µL of 100% ethanol with immediate air-blow dry at room temperature. After fixation, the cells were permeabilized with 100 µl of chilled (−20° C.) 90% methanol in deionized water for 5 minutes at room temperature with gentle shaking. After permeabilization, the solution in the container was disposed and the cells were washed with phosphate buffer saline for 2 times of 5 minutes under gentle shaking. 1000 of 3% $H_2O_2$ were added to the sample and incubated for 20 minutes at room temperature with gentle shaking to block endogenous hydrogen peroxidase. After the incubation was completed, the solution was disposed and the cells were washed three times of 5 minutes each time with gentle shaking. The cells were then incubated in 100 µl of 10% normal goat serum for one hour at room temperature with gentle shaking for blocking the non-specific binding site on the samples and the surface of the microtiter plate to eliminate non-specific binding. 50 µl of the anti-β actin antibody were used in 1:200 dilution in 10% normal goat serum for one set of the duplicate samples. 50 µl of the anti-HPV E6 antibody were used in 1:200 dilution in 10% normal goat serum for another set of the duplicate samples. All the samples were incubated for 1 hour under room temperature with gentle shaking. After the incubation was completed, the solution was disposed and the samples were washed with PBS washing solution for 3 times of 5 minutes each under gentle shaking. 50 µl of the biotinylated secondary antibody was then added using 1:500 dilution in 5% normal goat serum and incubated the samples for 30 minutes under room temperature with gentle shaking. After the incubation was completed, the solution was disposed and the samples were washed with PBS washing solution for 3 times of 5 minutes each under gentle shaking. 50 µl of the streptavidin conjugated HRP solution was then added using 1:600 dilution in PBS and incubated the samples for 45 minutes under room temperature with gentle shaking. After the incubation was completed, the solution was disposed and the samples were washed with PBS washing solution for 3 times of 5 minutes each under gentle shaking. 50 µl of TMB substrate was then added to incubate the sample under room temperature without disturbance for 10 minutes. 25 µl of the acid stop solution was then added to stop the enzymatic reaction and the signal intensity was read out using colorimetric plate reader. The assay was repeated for at least 2 times to confirm reproducibility. Whole cell ELISA results using anti-beta-actin antibody for cervical cancer cell lines are shown in FIG. 9A.

Figure 9B:
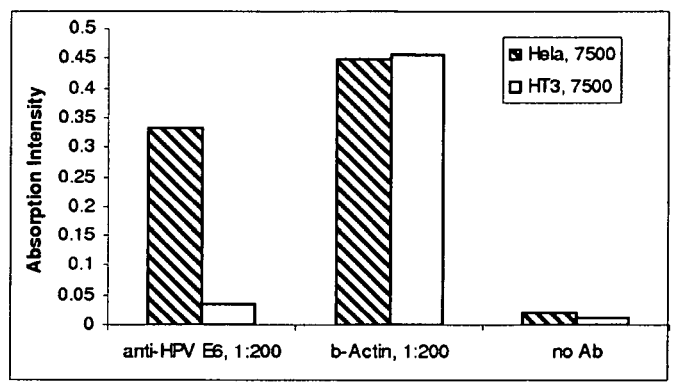
FIG. 9B provides an exemplary whole-cell ELISA result shown as absorption intensity for 7500 Hela cells and 7500 HT3 cells using anti-HPV E6 antibody and anti-β actin.
Figure 9C:
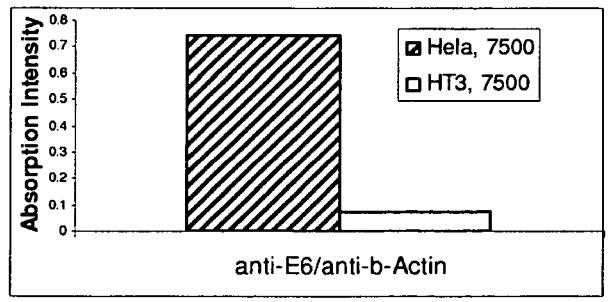
FIG. 9C provides an exemplary whole-cell ELISA result shown as ratio of the absorption intensity using anti-HPV E6 antibody and anti-β actin antibody for 7500 Hela cells and 7500 HT3 cells. β-actin was used as a reference used to normalize the signal intensity from the clinical samples that often contains various numbers of cells.

FIG. 9B shows the absorption intensity for 7500 Hela cells (striped bars, HPV positive cell line) and 7500 HT3 cells (solid bars, HPV negative cell line) obtained from whole cell ELISA using anti-HPV E6 antibody and anti-β actin antibody to detect the expression level of HPV E6 and β-actin protein in the cells. Cell samples with no primary antibody added were used as a control, which shows minimum signal intensity. The results show that there is a significant difference in absorption intensity between Hela and HT3 cells when using anti-HPV E6 antibody, indicating a differential expression level in HPV E6 protein in those two cell lines. In contract, when using β actin antibody, the difference in absorption intensity between the two cell lines is negligible, indicating that β-actin remains the same level of total cell protein and can be used as a standard to normalize the amount of cells immobilized in the surface of the container for the whole cell ELISA assay, thus to quantify the amount of HPV proteins as described in the Application. Since the signal intensity raised from anti-β-actin is in proportion to the total cell protein, the signal intensity raised from anti-HPV E6 from samples with various cell numbers can be normalized based on the signal intensity raised from anti-β-actin antibody. FIG. 9C shows ratio of absorption intensity from anti-HPV E6 to anti-β-actin for 7500 Hela cells (striped bars, HPV positive cell line) and 7500 HT3 cells (solid bars, HPV negative cell line) obtained from whole cell ELISA using anti-HPV E6 antibody and anti-β actin antibody to detect the expression level of HPV E6 and β-actin protein in the cells. Anti-β-actin antibody was used to normalize the signal intensity associated with HPV protein expression from various numbers of cells immobilized in the microtiter wells in the whole cell ELISA as described in the Application. We then normalize the expression level of HPV protein in the cells based on the amount of β-actin detected by anti-β-actin antibody in the cells per well. These data demonstrated that β-actin can be used as a reference used to normalize the signal intensity from the clinical samples that often contains various numbers of cells.

Normalization of the signal intensity using β-actin as the reference was then tested on clinical samples with each likely consisting of various amounts of cell numbers. Following the same protocol as described in [0228], whole cell ELISA was performed using anti-HPV E6 antibody and anti-β actin antibody to in parallel detect the expression level of HPV E6 oncoprotein and β-actin protein in 16 clinical samples. Without the pre-assay normalization as described in Example 5.1, two sets of duplicates of 50 µl of each sample were dispensed to the clear, flat bottom and high binding 96-well microtiter plate. Samples were immobilized for 30 minutes at room temperature. After immobilization the solution was disposed, and the samples were fixed using 25 µL of 100% ethanol with immediate air-blow dry at room temperature. After fixation, the samples were permeabilized with 100 µl of chilled (−20° C.) 90% methanol in deionized water for 5 minutes at room temperature with gentle shaking. After permeabilization, the solution in the container was disposed and the cells were washed with phosphate buffer saline for 2 times of 5 minutes under gentle shaking. 100 µl of 3% $H_2O_2$ were added to the sample and incubated for 20 minutes at room temperature with gentle shaking to block endogenous hydrogen peroxidase. After the incubation was completed, the solution was disposed and the cells were washed three times of 5 minutes each time with gentle shaking. The samples were then incubated in 100 µl of 10% normal goat serum for one hour at room temperature with gentle shaking for blocking the non-specific binding site on the samples and the surface of the microtiter plate to eliminate non-specific binding. 50 µl of the anti-β actin antibody were used in 1:200 dilution in 10% normal goat serum for one set of the duplicate samples. 50 µl of the anti-HPV E6 antibody were used in 1:200 dilution in 10% normal goat serum for another set of the duplicate samples. All the samples were incubated for 1 hour under room temperature with gentle shaking. After the incubation was completed, the solution was disposed and the samples were washed with PBS washing solution for 3 times of 5 minutes each under gentle shaking. 50 µl of the biotinylated secondary antibody was then added using 1:500 dilution in 5% normal goat serum and incubated the samples for 30 minutes under room temperature with gentle shaking. After the incubation was completed, the solution was disposed and the samples were washed with PBS washing solution for 3 times of 5 minutes each under gentle shaking. 50 µl of the streptavidin conjugated HRP solution was then added using 1:600 dilution in PBS and incubated the samples for 45 minutes under room temperature with gentle shaking. After the incubation was completed, the solution was disposed and the samples were washed with PBS washing solution for 3 times of 5 minutes each under gentle shaking. 50 µl of TMB substrate was then added to incubate the sample under room temperature without disturbance for 10 minutes. 25 µl of the acid stop solution was then added to stop the enzymatic reaction and the signal intensity was read out using colorimetric plate reader. The assay was repeated for at least 2 times to confirm reproducibility. Whole cell ELISA results are shown in FIG. 10.

To demonstrate that β-actin can be used as reference to normalize variation of cell numbers present among the clinical samples, 16 representative clinical samples were tested on whole-cell ELISA assay in duplicated sets. The first set of samples was tested using anti-HPV E6 antibody. The second set of samples was tested using anti-β-actin antibody. Data set analyzed from $1^{st}$ and $2^{nd}$ set separately is defined as a single marker experiment (FIG. 10A). Data analyzed from both sets in ratio of the two markers is defined as a dual marker experiment (FIG. 10B) FIG. 10 shows a comparison of screening method using (A) single marker, anti-HPV E6 antibodies and (B) dual markers, anti-HPV E6 and anti-β-actin antibodies. In FIG. 10A, single marker screening was used. Absorption intensity (OD) data were obtained from whole cell ELISA using anti-HPV E6 antibodies to screen 16 clinical samples. HPV positivity was defined when OD is higher than 0.400. Eight samples were tested as HPV positive and eight as HPV negative. In FIG. 10B, dual marker screening was used. Absorption intensity (OD) data were obtained from whole cell ELISA using anti-HPV E6 and anti-β-actin antibodies to screen the same 16 clinical samples tested in (A). HPV positivity was defined when the ratio of the OD of anti-E6 to anti β-actin is higher than 2.0. The same eight samples that were tested positive in the single marker screening remain positive while using the dual marker screening method, and the other eight remain negative. These results demonstrated that anti-β-actin antibody can be used to normalize the amount of cells immobilized in the microtiter wells in the whole cell ELISA assay as described in the Application. By using anti-β-actin antibody, it allows the signal intensity associated with samples with various amount of cells to be normalized based on the signal intensity obtained using anti-β-actin antibody.

Example 7.3

Normalization Using Cell Stain, as an Example, Trypan Blue Staining

After the assay was completed and the ELISA data was obtained from the plate reader, the solution in the container was disposed. The samples were washed. 50 μl of trypan blue solution was dispensed in the container. The samples were incubated in the trypan blue solution for 5 minutes and the solution was disposed afterwards. The darkness of the cell staining was observed, which represents the amount of cells deposited on the surface in the container. The amount of the cells in the samples thus can be estimated and the ELISA data can be normalized according to the cell numbers.

The procedures described in this Example demonstrate various methods for cell number normalization in clinical samples to allow measurement or quantification of HPV protein expression levels in the clinical samples. Based on the detection of specific binding of the anti-HPV antibodies to the HPV protein in the normalized cells immobilized on the microtiter plate from the clinical samples, this methods enable accurate quantitative analysis of HPV proteins present in clinical samples Example 8

Quantification of the Express Level of HPV Proteins in the Samples

The whole-cell ELISA assay described in the instant invention detects the expression of HPV oncoproteins in the samples of interest in the form of signal readout based on the specific binding of those oncoproteins to the antibodies raised against purified recombinant HPV proteins. Thus, quantification of the expression level of the HPV oncoproteins can be achieved by comparing the signal intensity obtained from the samples to the signal intensity obtained from HPV recombinant proteins with known concentrations.

ELISA assay was performed on purified recombinant HPV proteins with various concentrations. Purified recombinant HPV proteins were obtained and characterized using the procedures as described in Example 1. Serial dilution of the protein from 200ng per 50 μl to 0.02 pg per 50 μl was made in phosphate buffer saline. Triplets of 50 μl of the samples of each dilution were dispensed to the clear, polystyrene coated, flat bottom and high binding 96-well microtiter plate. Protein samples were immobilized for 24 hours at 4° C. The solution was disposed after immobilization. The samples were incubated in 100 μl of 10% normal goat serum at room temperature for 2 hours to block the non-specific binding site on the samples and the surface of the microtiter plate to eliminate non-specific binding. 50 μl of the primary antibody, either anti-HPV E6 or anti-HPV E7 antibodies were used in 1:200 dilution in 10% normal goat serum to incubate the samples for 1 hour under room temperature with gentle shaking. After the incubation was completed, the solution was disposed and the samples were washed with PBS washing solution for 3 times of 5 minutes each under gentle shaking. 50 μl of the biotinylated secondary antibody was then added using 1:500 dilution in 5% normal goat serum and incubated the samples for 30 minutes under room temperature with gentle shaking. After the incubation was completed, the solution was disposed and the samples were washed with PBS washing solution for 3 times of 5 minutes each under gentle shaking. 50 μl of the streptavidin conjugated HRP solution was then added using 1:600 dilution in PBS and incubated the samples for 45 minutes under room temperature with gentle shaking. After the incubation was completed, the solution was disposed and the samples were washed with PBS washing solution for 3 times of 5 minutes each under gentle shaking. 50 μl of TMB substrate was then added to incubate the sample under room temperature without disturbance for 10 minutes. 25 μl of the acid stop solution was then added to stop the enzymatic reaction and the signal intensity was read out using colorimetric plate reader. The assay was repeated for at least 2 times to ensure data quality and reproducibility. Signal intensity data was graphed against the corresponding concentration of the protein and the absorbance protein standard curve was generated.

The assay was also carried out using the white, polystyrene coated, flat bottom and high binding 96-well microtiter plate with the same procedures as described above. 50 μl of the chemiluminescent substrate was used for chemiluminescent signal readout. Signal intensity data was graphed against the corresponding concentration of the protein and the chemiluminescent protein standard curve was generated.

FIG. 5 shows the results for protein standard curves for HPV E6 and HPV E7 protein. Anti-HPV E6 monoclonal antibody was used to detect the presence of HPV E6 protein. Anti-HPV E7 monoclonal antibody was used to detect the presence of HPV E7 protein. FIG. 5A: Standard curve for HPV18 E6 protein (diamond dots) and HPV16 E6 protein (square dots) using colorimetric method; FIG. 5B: standard curve for HPV18 E6 protein with varies dilution (diamond dots: 200× dilution, square dots: 1000× dilution, and triangle dots: 5000× dilution) using luminescent method; and FIG. 5C: standard curve for HPV16 E6 protein using luminescent method. FIG. 5D: Standard curve for HPV18 E7 protein (diamond dots) and HPV16 E7 protein (square dots) using colorimetric method; FIG. 5E: standard curve for HPV18 E7 protein with varies dilution (diamond dots: 200× dilution, square dots: 1000× dilution, and triangle dots: 5000× dilution) using luminescent method; and FIG. 5F: standard curve for HPV16 E7 protein using luminescent method. These standard curves were used for estimating the amount of HPV E6 or HPV E7 protein expressed in clinical samples. Based on the amount of HPV E6 or HPV E7 protein expressed, the clinical samples were categorized to different stages of cervical cancer development. The methods described in this invention enable quantification HPV protein in clinical samples correlated to disease grade.

The procedures and results described in this Example demonstrate methods of generating HPV protein standard curves for at least HPV18 E6, HPV18 E7, HPV16 E6 and HPV 16 E7 using absorption and luminescent signal intensity that represent quantity of HPV protein expression level obtained from the specific binding of anti-HPV antibody to the purified recombinant HPV protein. These HPV protein standard curves were used to compare to the signal intensity obtained for clinical samples to estimate the HPV protein expression level in the HPV-infected cells in the clinical samples used in the whole-cell ELISA assay as described in the instant Application.

To analyze the HPV IHC results from each subject of invasive cancer, Table 6 shows data from 24 cases of invasive cancer samples with IHC score for staining of cytoplasm (C), and nucleus (N) using C, or N followed by the % of staining using the anti-HPV E7 antibody. Additional anti-HPV antibodies including another anti-E7 antibody, Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies was also shown in Table 6. Results of HPV DNA typing were also shown on the table for its corresponding case.

As shown in Table 6, both nucleus and cytoplasmic staining are found in all the subjects of tumor cells from SCC and ADE stained by the anti-E7 antibody. However, there is more staining (percentage stained) found in the cytoplasm of tumor cells comparing the staining of nuclear of tumor cells. The detection of HPV E7 protein in its adjacent normal epithelium cells was only found in nucleus, but not found in the cytoplasm of the epithelial cells. The staining of cytoplasm appears most distinguishable tumor cells compared to its corresponding normal adjacent cells. These data demonstrate expression of HPV E7 proteins was detected in the cytoplasm and nuclear of tumor cells of SCC and ADE tissues. The localization of the E7 proteins expressed in the cytoplasm of tumor cells, but not in the normal epithelium or stroma cells appears tumor specific. HPV E7 proteins present in the nucleus of normal adjacent epithelium and tumor cells detected by the anti-HPV E7 antibody indicate HPV infection with oncoproteins expression. Similar staining pattern was also found when used other anti-HPV antibodies as shown in Table 6. Data indicate that the HPV IHC assay as described herein can detect HPV early gene such as E6, E7, and late gene such as L1 proteins present in the tumor cells of cervical cancer tissues.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least HPV-16, HPV-18, HPV-33, HPV-45, etc, which are cancer-related HPV types (high risk HPV types). The single anti-E7 monoclonal antibody can also detect HPV infection by two or more HPV types, such as the combination of HPV 11, HPV-16, HPV-18, HPV-52, HPV-58, HPV-51, HPV-59, etc., which include high risk, low risk, and non-oncogenic α-papillomaviruses. However, infection by multiple HPV types contains at least one type is high-risk HPV type. These data indicate that the anti-E7 antibody described in this invention is non-type specific, thus provides a powerful tool to detect HPV E7 proteins from most common high-risk HPV types in the cervical cancer.

TABLE 6

IHC staining results (stained %) and HPV DNA typing for 12 SCC biopsy samples and 12 ADC biopsy samples (C: Cytoplasmic; N: Nucleus; Dys: dysplasia or tumor cells).

| Sample # | HPV type | Anti E7 | | | | Another anti-E7 Dys (%) | Anti-E6 Dys (%) | Another anti-E6 Dys. (%) | Anti-L1 Dys. (%) |
|---|---|---|---|---|---|---|---|---|---|
| | | Dys (% stained) | | Normal epith. (% stained) | | | | | |
| | | C | N | C | N | C | C | C | C |
| SCC-1 | 18 | 85 | 85 | 0 | 20 | 12.5 | 10 | 70 | 55 |
| SCC-2 | 16, 52 | 90 | 85 | 0 | 25 | 15 | 15 | 10 | 55 |

TABLE 6-continued

IHC staining results (stained %) and HPV DNA typing for 12 SCC biopsy samples and 12 ADC biopsy samples (C: Cytoplasmic; N: Nucleus; Dys: dysplasia or tumor cells).

| Sample # | HPV type | Anti E7 | | | | Another anti-E7 Dys (%) | Anti-E6 Dys (%) | Another anti-E6 Dys. (%) | Anti-L1 Dys. (%) |
|---|---|---|---|---|---|---|---|---|---|
| | | Dys (% stained) | | Normal epith. (% stained) | | | | | |
| | | C | N | C | N | C | C | C | C |
| SCC-3 | 16 | 60 | 65 | 0 | 40 | 5 | 0 | 10 | 20 |
| SCC-4 | 16 | 92 | 50 | 0 | 40 | 5 | 0 | 10 | 85 |
| SCC-5 | 16, 52, 58 | 92 | 55 | 0 | 50 | 20 | 5 | 15 | 88 |
| SCC-6 | 18, 52, 58 | 90 | 60 | | | 25 | 18 | 10 | 70 |
| SCC-7 | 16, 52 | 92 | 75 | 0 | 30 | 30 | 5 | 10 | 20 |
| SCC-8 | 16, 58 | 10 | 10 | 0 | 5 | 0 | 0 | 10 | 50 |
| SCC-9 | no DNA | 95 | 60 | 0 | 40 | 25 | 8 | 15 | 8 |
| SCC-10 | 18 | 92 | 65 | 0 | 60 | 45 | 25 | 20 | 65 |
| SCC-11 | 16, 58 | | | 0 | 80 | 5 | | 0 | 0 |
| SCC-12 | 33 | 95 | 90 | 0 | 0 | 30 | 1 | 20 | 55 |
| ADE-1 | 16, 18 | 30 | 20 | 0 | 50 | 15 | 25 | 20 | 82 |
| ADE-2 | no DNA | 62 | 40 | 0 | 30 | 35 | 70 | 35 | 78 |
| ADE-3 | 16 | 20 | 30 | 0 | 20 | 35 | 55 | 60 | |
| ADE-4 | 16, 18 | 80 | 80 | 0 | 0 | 10 | 5 | 0 | 90 |
| ADE-5 | 51, 52 | 95 | 80 | 0 | 50 | 10 | 70 | 15 | 92 |
| ADE-6 | 11, 16, 52 | | | 0 | 40 | 5 | 0 | 0 | 15 |
| ADE-7 | 18 | 50 | 40 | 0 | 60 | 25 | 20 | 20 | 75 |
| ADE-8 | 18 | 85 | 60 | 0 | 40 | 15 | 50 | 15 | 82 |
| ADE-9 | 45 | 82 | 55 | 0 | 30 | 30 | 2 | 20 | 40 |
| ADE-10 | 18 | 15 | 10 | 0 | 40 | 15 | 15 | 5 | 70 |
| ADE-11 | 18, 59 | 70 | 0 | 0 | 50 | 15 | 8 | 5 | 65 |
| ADE-12 | 18 | | | | | | | | 30 |

To analyze the HPV IHC results from each subject of CIN3, Table 7 shows data from 30 cases of CIN 3 samples with IHC score for staining of cell membrane (M), cytoplasm (C), and nucleus (N) using M, C, or N followed by the % of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies was also shown in Table 6. Results of HPV DNA typing were also shown on the table for its corresponding case.

As shown in Table 7, nucleus staining are found in the dysplasia cells of all the CIN3 samples tested while only certain proportion of cases found staining of cytoplasm by the anti-E7 antibody. The results indicate that there is more staining found in the cytoplasm than in the nuclear of dysplasia cells. As shown previously in invasive cancer tissues, HPV E7 protein in its adjacent normal epithelium cells was only found in nucleus, but not found in the cytoplasm of the epithelial cells. The staining of cytoplasm appears most distinguishable in dysplasia cells compared to its corresponding normal adjacent cells. The localization of the E7 proteins expressed in the cytoplasm of dysplasia cells, but not in the normal epithelium or stroma cells appears HSIL specific. These data demonstrate expression of HPV E7 proteins can be detected in the cytoplasm and nuclear of dysplasia cells of CIN3 tissues. HPV E7 proteins present in the nucleus of normal adjacent epithelium and dysplasia cells detected by the anti-HPV E7 antibody indicate HPV infection with oncoproteins expression. For the cases with high level expression of HPV E7 proteins detected in the cytoplasm of dysplasia cells, it may suggest specific indication of dysplasia progression. Similar staining pattern was also found when used other anti-HPV antibodies as shown in Table 7. Data indicate that the HPV IHC assay as described herein can detect HPV early gene such as E6, E7, and late gene such as L1 proteins present in the dysplasia cells of CIN3.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least HPV-16, HPV-18, HPV-31, HPV-33, HPV-39, HPV-58, etc, which are cancer-related HPV types (high risk HPV types). The single anti-E7 monoclonal antibody can also detect HPV infection by two or more HPV types, such as the combination of HPV-16, HPV-18, HPV-33, HPV-39, HPV-52, HPV-58, etc., which include most common high-risk HPV. These data indicate that the anti-E7 antibody described in this invention is non-type specific, thus provides a powerful tool to detect HPV E7 proteins from most common high-risk HPV types in the CIN3 tissues.

TABLE 7

IHC staining results (stained % and score; 0-3) and HPV DNA typing of 30 CIN 3 samples (M: Membrane; C: Cytoplasmic; N: Nucleus; Dys: Dysplasia).

| | | anti-E7 | | | | | | Anti-E6 Dys. (%) | Another anti-E7 Dys. (%) | Anti-L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 31 | 33 | 0 | 80 | 80 | 0 | 0 | 50 | 70 | 40 | 80 |
| 32 | 16 | 0 | 80 | 80 | | | 60 | 0 | 0 | 5 |
| 33 | 16, 58 | | | | 0 | 0 | 60 | | | |
| 34 | 31 | 0 | 50 | 70 | 0 | 0 | 50 | 0 | 0 | 10 |
| 35 | 16, 39 | 0 | 70 | 90 | 0 | 0 | 40 | 0 | 10 | 30 |
| 36 | 31 | 0 | 70 | 60 | 0 | 0 | 50 | 0 | 20 | 20 |
| 37 | 39 | 0 | 0 | 40 | 0 | 0 | 0 | 0 | 0 | 0 |
| 38 | 16 | | | | 0 | 0 | 40 | | | |
| 39 | 16 | 0 | 60 | 70 | 0 | 0 | 40 | 0 | | 0 |
| 40 | 58 | 0 | 90 | 90 | 0 | 0 | 50 | 50 | 0 | 30 |
| 41 | 16 | 0 | 0 | 50 | 0 | 0 | 50 | 0 | 20 | 20 |
| 42 | 16 | 0 | 70 | 70 | 0 | 0 | 30 | 0 | 0 | |
| 43 | 33 | 0 | 0 | 90 | 0 | 0 | 50 | 0 | 0 | 5 |
| 44 | 52 | 0 | 70 | 80 | 0 | 0 | 50 | 70 | 10 | 50 |
| 45 | 51, 52 | 0 | 90 | 90 | 0 | 0 | 30 | 80 | 50 | 10 |
| 46 | 16 | 0 | 0 | 80 | 0 | 0 | 50 | 0 | 0 | 5 |
| 47 | 16 | 0 | 60 | 80 | 0 | 0 | 50 | 30 | 10 | 20 |
| 48 | 16, 58 | 0 | 0 | 80 | 0 | 0 | 50 | 0 | 0 | 10 |
| 49 | 31 | 0 | 80 | 60 | | | 50 | 70 | 40 | 40 |
| 50 | 16 | 0 | 0 | 60 | 0 | 0 | 30 | 0 | 20 | 20 |
| 51 | 6 | | | | 0 | 0 | 20 | | 0 | |
| 52 | 16, 18, 33, 39 | 0 | 0 | 20 | 0 | 0 | 30 | 0 | 0 | 0 |
| 53 | 51, 52, 58 | 0 | 70 | 60 | 0 | 0 | | 60 | 60 | 40 |
| 54 | 16, 45 | 0 | 0 | 70 | 0 | 0 | 50 | 0 | 20 | 20 |
| 55 | 16 | 0 | 0 | 75 | 0 | 0 | 50 | 0 | 0 | 0 |
| 56 | 33, 52 | 0 | 0 | 80 | 0 | 0 | 50 | 0 | 0 | 10 |
| 57 | 16 | 0 | 0 | 50 | 0 | 0 | 40 | 0 | 0 | 0 |
| 58 | 33 | 0 | 0 | 80 | 0 | | | 0 | 20 | 10 |
| 59 | 16 | 0 | 0 | 60 | 0 | 0 | 20 | 0 | 10 | 5 |
| 60 | 16, 52, 58 | 0 | 70 | 80 | 0 | 0 | 50 | 70 | 0 | 20 |

To analyze the HPV IHC results from each subject of CIN2, Table 8 shows data from 30 cases of CIN 2 samples with IHC score for staining of cell membrane (M), cytoplasm (C), and nucleus (N) followed by the % of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of dysplasia cells using other anti-HPV antibodies was also shown in Table 8. Results of HPV DNA typing were also shown in the table for its corresponding case.

TABLE 8

IHC staining results (stained % and score; 0-3) and HPV DNA typing for 30 biopsy samples (CIN2). (M: membrane; C: cytoplasmic; N: nucleus; Dys: dysplasia)

| | | Anti-E7 | | | | | | another | | |
|---|---|---|---|---|---|---|---|---|---|---|
| | | Dysplasia (% stained) | | | Normal epithelium (% stained) | | | Anti-E6 Dys. (%) | anti-E7 Dys. (%) | Anti-L1 Dys. (%) |
| ID # | HPV type | M | C | N | M | C | N | Cyto | Cyto | Cyto |
| 1 | 6 | 0 | 80 | 80 | 0 | 0 | 30 | 70 | 40 | 80 |
| 2 | 31 | 0 | 0 | 90 | | | | 0 | 40 | 0 |
| 3 | 52 | 0 | 25 | 50 | 0 | 0 | 70 | 0 | 20 | 20 |
| 4 | 16 | 0 | 0 | 40 | 0 | 0 | 30 | 0 | 5 | 0 |
| 5 | 58 | 0 | 0 | 50 | 0 | 0 | 10 | 0 | 0 | 0 |
| 6 | 52 | 0 | 80 | 70 | 0 | 0 | 50 | 0 | 5 | 0 |
| 7 | 53 | 0 | 0 | 80 | 0 | 0 | 30 | 0 | 10 | 10 |
| 8 | 52 | 0 | 50 | 90 | 0 | 0 | 20 | 60 | 10 | 20 |
| 9 | 31 | 0 | 80 | 80 | 0 | 0 | 50 | 70 | 20 | 40 |
| 10 | 16 | 0 | 50 | 80 | 0 | 0 | 50 | 60 | 20 | 10 |
| 11 | no DNA | 0 | 0 | 50 | 0 | 0 | 70 | 0 | 0 | 10 |
| 12 | 33 | 0 | 60 | 60 | 0 | 0 | 50 | 0 | 10 | 30 |
| 13 | no DNA | 0 | 70 | 80 | 0 | 0 | 70 | 0 | 20 | 10 |
| 14 | 52 | 0 | 0 | 70 | 0 | 0 | 70 | 0 | 30 | 20 |
| 15 | no DNA | 0 | 0 | 70 | 0 | 0 | 50 | 0 | 20 | 5 |
| 16 | 52 | 0 | 0 | 10 | 0 | 0 | 30 | 0 | 0 | 5 |
| 17 | 52 | 0 | 0 | 60 | 0 | 0 | 80 | 0 | 0 | 5 |
| 18 | 16 | 0 | 50 | 60 | 0 | 0 | 30 | 50 | 10 | 20 |
| 19 | 16 | 0 | 50 | 70 | | | | 0 | 10 | 20 |
| 20 | 52, 44 | 0 | 50 | 80 | 0 | 0 | 40 | 0 | 30 | 30 |
| 21 | 16 | 0 | 0 | 50 | 0 | 0 | 50 | 0 | 20 | 20 |
| 22 | 16, 18, 6 | 0 | 0 | 40 | 0 | 0 | 0 | 0 | 10 | 0 |
| 23 | 16, 31 | 0 | 0 | 30 | 0 | 0 | 60 | 0 | 0 | |
| 24 | 6 | 0 | 0 | 80 | 0 | 0 | 50 | 0 | 10 | 5 |
| 25 | 16 | 0 | 0 | 10 | 0 | 0 | 60 | 0 | 0 | 0 |
| 26 | 58 | 0 | 0 | 40 | 0 | 0 | 40 | 0 | 10 | 5 |
| 27 | 16, 39, 52 | | | | 0 | 0 | 70 | | 0 | |
| 28 | 6 | 0 | 0 | 50 | 0 | 0 | 70 | 0 | 10 | 5 |
| 29 | 16 | 0 | 0 | 70 | 0 | 0 | 5 | 0 | 10 | 20 |
| 30 | 66, 68, | 0 | 0 | 30 | 0 | 0 | 60 | 0 | 10 | 0 |

As shown in Table 8, nucleus staining are found in the dysplasia cells of all the CIN2 samples tested while only certain proportion of cases found staining of cytoplasm by the anti-E6 or anti-E7 antibody. The results indicate there is more staining of nucleus than cytoplasm of dysplasia cells found in CIN2 samples. As shown previously in SCC, ADC, and CIN3, HPV E7 protein in its adjacent normal epithelium cells was only found in nucleus, but not found in the cytoplasm of the epithelial cells. The staining of cytoplasm in CIN2 using anti-E6 antibody appears most distinguishable in dysplasia cells compared to its corresponding normal adjacent cells. The localization of the E6 proteins expressed in the cytoplasm of dysplasia cells, but not in the normal epithelium or stroma cells appears HSIL specific. These data demonstrate expression of HPV E6 proteins can be detected in the cytoplasm and nuclear of dysplasia cells of CIN2 tissues. For the cases with high level expression of HPV E6 proteins detected in the cytoplasm of dysplasia cells, it may suggest dysplasia progression. Similar staining pattern was also found when used other anti-HPV antibodies as shown in Table 8. The HPV IHC assay as described herein can be used to detect HPV early gene such as E6, E7, and late gene such as L1 proteins present in the dysplasia cells of CIN2.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least, HPV-16, HPV-18, HPV-31, HPV-52, HPV-58, etc, which are cancer-related HPV types (high risk HPV types) and HPV6, HPV 53 which are not high-risk HPV types. The single anti-E7 monoclonal antibody can also detect HPV infection by two or more HPV types, such as the combination of HPV6, HPV-16, HPV-18, HPV-31, HPV-39, HPV-44, HPV-52, HPV-58, HPV-66, HPV-68, etc., which include most common high-risk HPV as well as low risk HPV types. These data indicate that the anti-E7 antibody described in this invention is non-type specific, able to detect HPV E7 proteins from common high-risk HPV types as well as low risk types in the CIN2 tissues. It is possible that formation of dysplasia cells is resulted from expression of oncoproteins, rather than genotyping of HPV types. It explains regression may occur for those infection by high-risk types with no detection of oncoproteins in cytoplasm. Thus, the HPV IHC assay described herein provides additional clinical information, not only for detection of HPV infection, but also for indication of dysplasia progression.

Figure 12A:
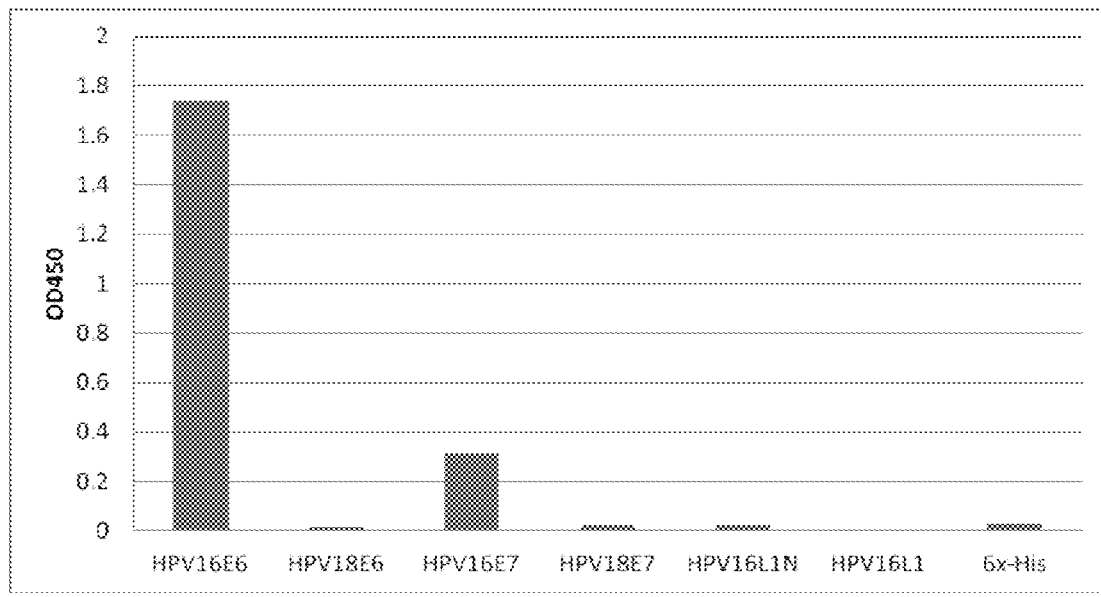
FIG. 12A shows the specificity of a monoclonal antibody capable of reacting with both HPV 16 E6 and HPV 16 E7 recombinant proteins (different HPV proteins from the same HPV type) and recognizing a common epitope on the different HPV16 E6 and HPV16 E7 proteins from the same HPV 16 type as assayed on EIA (enzyme immuno assays) according to one embodiment of the invention.
Figure 12B:
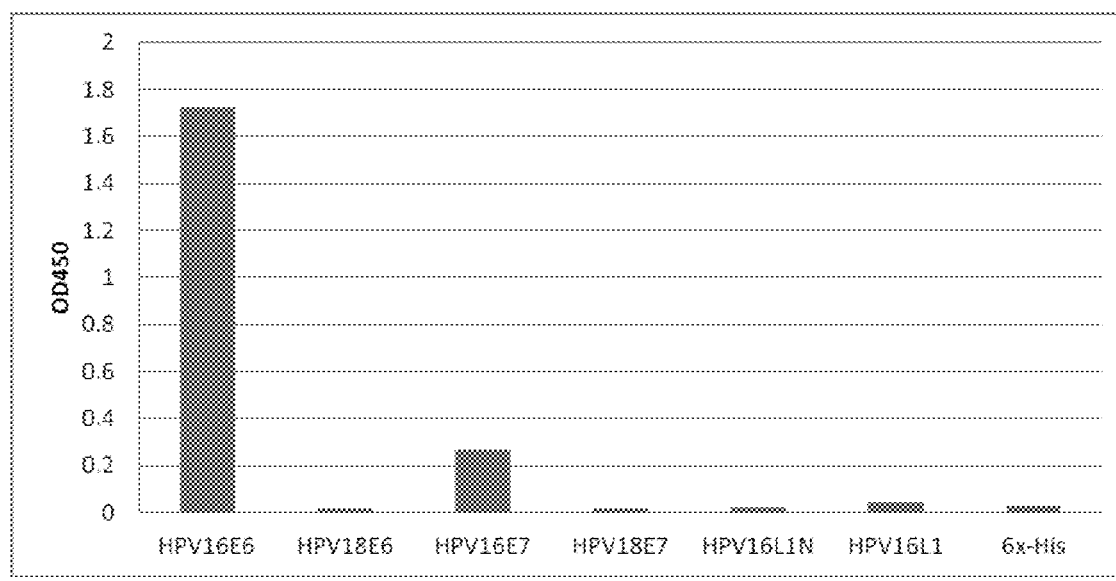
FIG. 12B shows the specificity of another monoclonal antibody capable of reacting with both HPV 16 E6 and HPV 16 E7 recombinant proteins and recognizing a common epitope on the HPV 16 E6 and HPV16 E7 proteins as assayed on EIA according to one embodiment of the invention.

To demonstrate a monoclonal antibody capable of binding to two or more HPV viral proteins from the same HPV type as described in this invention, FIG. 12A and FIG. 12B show the specificity of a monoclonal antibody, capable of reacting with both recombinant HPV16 E6 and HPV16E7 proteins on EIA. These data demonstrate the monoclonal antibody described herein reacts specifically to HPV16E6 and HPVE7, but not reactive to neither HPV16L1, nor HPV18 E6 or HPV18E7. FIG. 12A and FIG. 12B represent two different clones of hybridoma cells, each clone being capable of producing a monoclonal antibody recognizing a common epitope on both HPV16 E6 and HPV16 E7 proteins.

Figure 13:
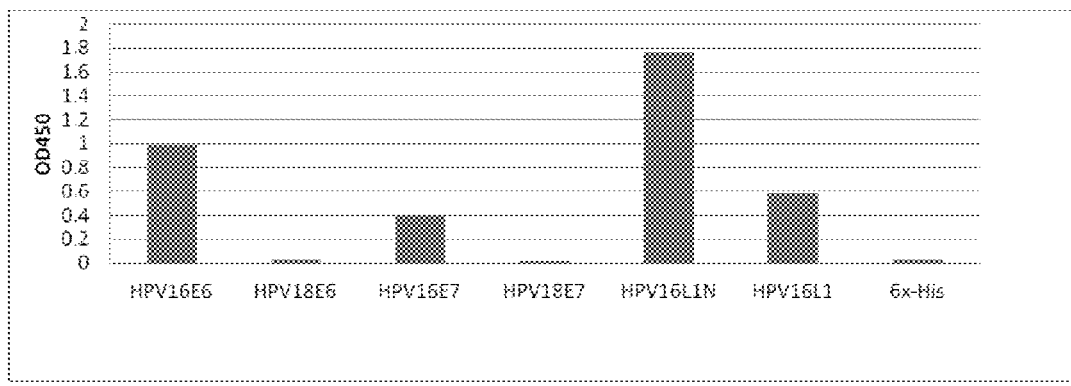
FIG. 13A shows the specificity of a monoclonal antibody capable of reacting with HPV16 E6, E7, L1 & L1 N-terminal recombinant proteins (different HPV proteins from the same HPV type) and recognizing a common epitope on the different E6, E7, L1, and L1 N-terminal proteins from the same HPV 16 type as assayed on EIA according to another embodiment of the invention.

To demonstrate a monoclonal antibody capable of binding to an early HPV viral protein and a late HPV viral proteins from the same HPV type as described in this invention, FIG. 13A shows the specificity of a monoclonal antibody capable of reacting with recombinant HPV E6, HPV E7 and HPV L1 proteins on EIA. The recombinant protein coated on microtiter plate to be detected by the antibody described herein is in native form. These data demonstrate the monoclonal antibody described herein reacts strongly to native forms of recombinant HPV16 E6 and L1 proteins, and weakly to native form of recombinant HPV16 E7 protein, but non-reactive to native form of recombinant HPV18 E6 or HPV18 E7. These data indicate that this antibody contains a HPV 16 common epitope to be recognized by native form of HPV16E6, HPV16E7 and HPV protein.

Figure 14:
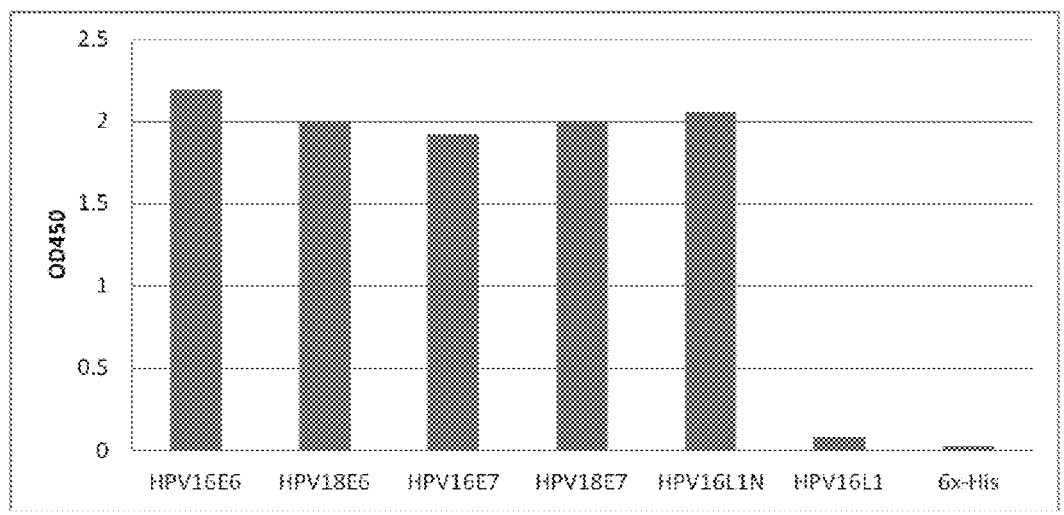
FIG. 14A shows the specificity of a monoclonal antibody capable of binding to all of the recombinant HPV16 E6, E7, L1 N-terminal proteins as well as HPV18 E6 and E7 proteins (HPV proteins from different HPV types) and recognizing a common epitope on the E6, E7, L1 N-terminal proteins from HPV16 and HPV18 as assayed on EIA according to another embodiment of the invention.

To demonstrate a monoclonal antibody capable of binding to an early HPV viral protein and a late HPV viral proteins from different HPV type as described in this invention, FIG. 14A shows the specificity of a monoclonal antibody capable of reacting with recombinant E6, E7 and L1 proteins from both HPV16 and HPV 18 on EIA. These data demonstrate this monoclonal antibody reacts specifically to all of the recombinant E6, E7 and L1 proteins of HPV16, and the recombinant E6 and E7 proteins of HPV18, but not to its common his-tag peptide. These data indicate that this antibody contains a common epitope shared by HPV16 and HPV18, as evidenced by its ability to react with all of the recombinant HPV16 E6, HPV16 E7, HPV16 L1, HPV18 E6, and HPV18 E7 proteins.

Figure 15:
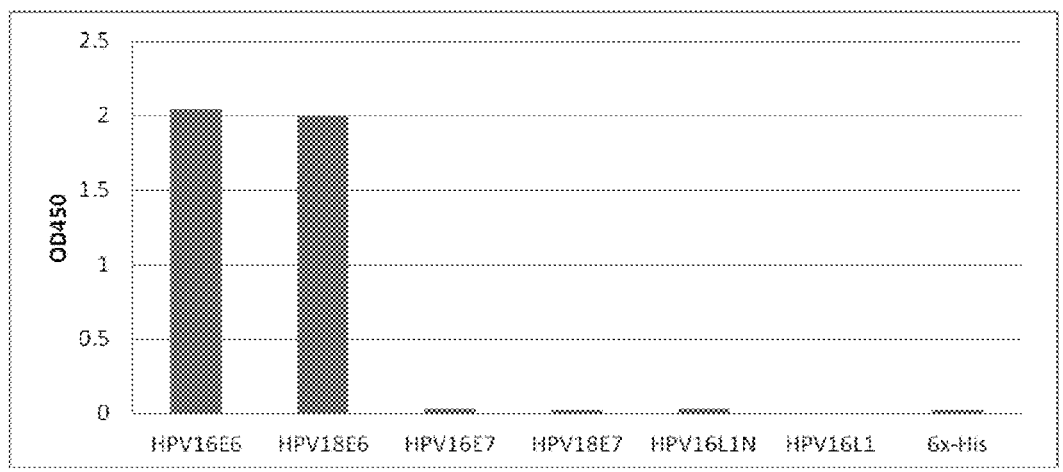
FIG. 15A shows the specificity of a monoclonal antibody capable of binding to two E6 recombinant proteins (HPV16 E6 and HPV18 E6, E6 proteins from different HPV types) and recognizing a common epitope on the two E6 proteins from different HPV types as assayed on EIA according to another embodiment of the invention.

To demonstrate a monoclonal antibody capable of binding to tow or more HPV viral proteins from different HPV type as described in this invention, a monoclonal antibody capable of reacting with recombinant E6 proteins of HPV 16 and HPV18 is also the obtained. FIG. 15A shows the specificity of a monoclonal antibody with common epitope capable of reacting with recombinant HPV16 E6 and HPV18E6 proteins on EIA. The recombinant protein coated on microtiter plate to be detected by the antibody described herein is in native form. These data demonstrate the monoclonal antibody reacts strongly to native form of recombinant HPV16 E6 and HPV18E6 proteins, but non-reactive to native form of recombinant HPV E7 nor HPV L1 proteins. These data indicate that this antibody contains HPV E6 common epitope capable of reacting with native form of recombinant HPV16 E6, and HPV18 E6 proteins.

Figure 16:
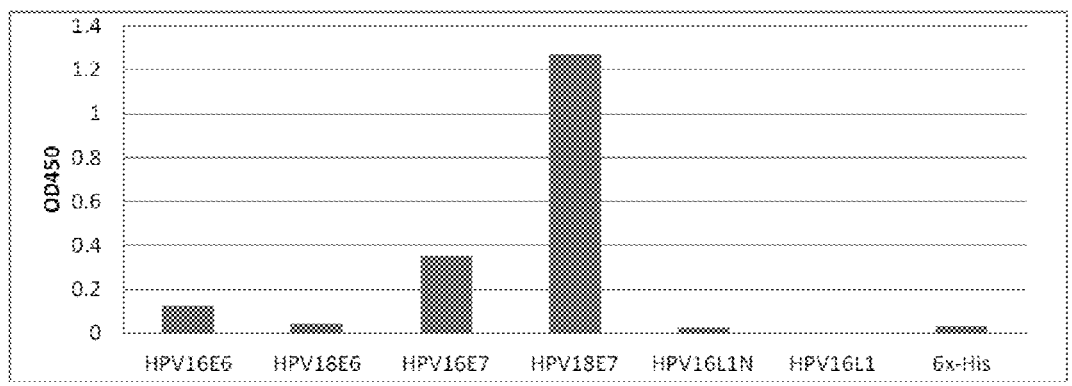
FIG. 16 shows the specificity of a monoclonal antibody capable of reacting with two recombinant HPV16 E7 and HPV18 E7 proteins (E7 proteins from different HPV types) and recognizing a common epitope on the two E7 proteins from different HPV types as assayed on EIA.

As another example to demonstrate a monoclonal antibody capable of binding to tow or more HPV viral proteins from different HPV type as described in this invention, FIG. 16 shows the specificity of a monoclonal antibody capable of reacting with both recombinant HPV16 E7 and HPV 18E7 protein on EIA. The recombinant protein coated on microtiter plate detected by the antibody described herein is in native form. These data demonstrate the monoclonal antibody described herein reacts strongly to native form of recombinant HPV16 E7 and HPV18 E7 proteins, but non-reactive to native form of recombinant HPV E6 nor HPV L1 proteins. These data indicate that this antibody contains HPV E7 common epitope capable of reacting with native form of HPV16 E7, and HPV18 E7 proteins.

Figure 17A:
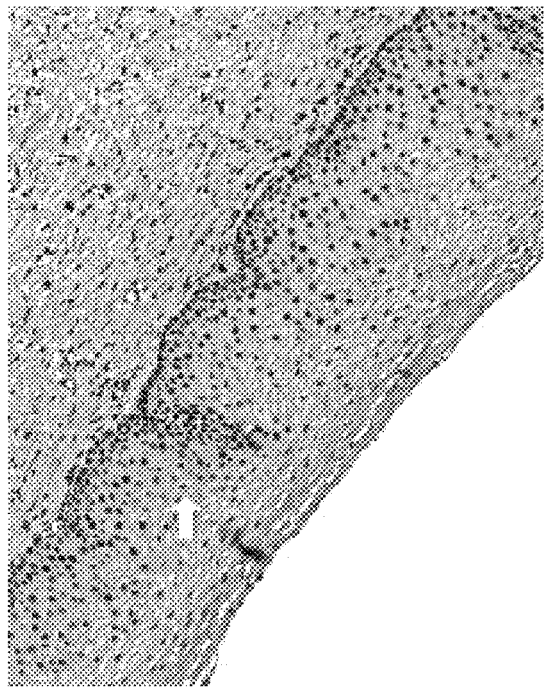
FIG. 17A shows the representative staining image of the dysplasia cells of CIN2 tissues using an anti-E6 monoclonal antibody in an immunohistocytostaining (IHC) assay.
Figure 17B:
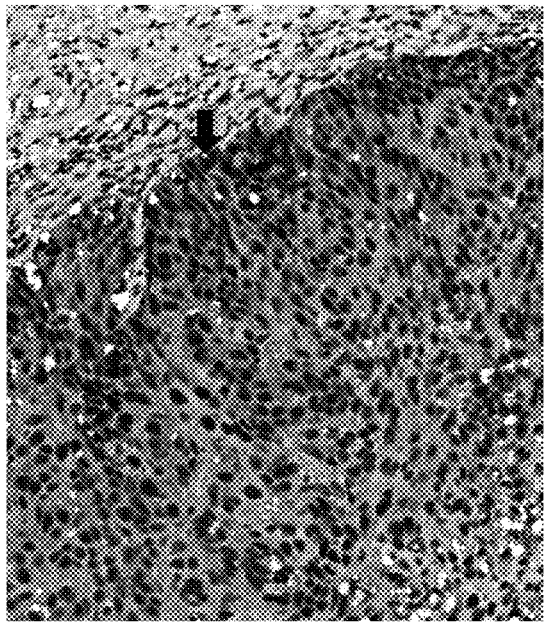
FIG. 17B shows the representative staining image of the adjacent normal epithelium from the dysplasia tissue of the CIN2 sample of FIG. 17A.
Figure 17D:
FIG. 17D shows the representative staining image of the dysplasia epithelium of another CIN3 sample stained by the same anti-E6 monoclonal antibody as used in FIG. 17A in an IHC assay.
Figure 17C:
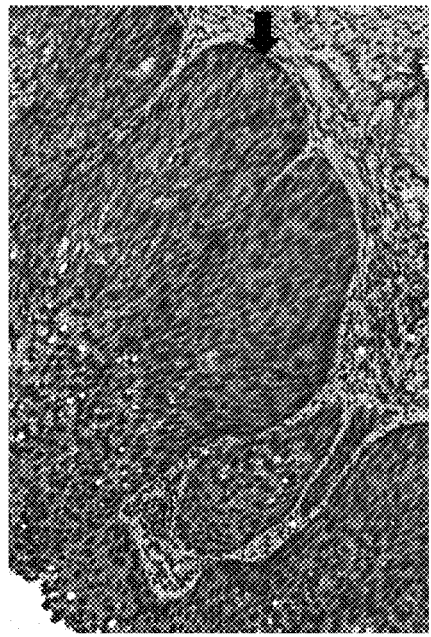
FIG. 17C shows the representative staining image of the dysplasia epithelium of a CIN3 sample stained by the same anti-E6 monoclonal antibody as used in FIG. 17A in an IHC assay, demonstrating specific IHC staining in the nuclear and cytoplasm of dysplasia cells by the anti-E6 monoclonal antibody.

FIG. 17A shows the representative image of the dysplasia cells of CIN2 tissues stained by immunohistocytostaining (IHC) using an anti-E6 monoclonal antibody. FIG. 17B shows the representative image of the adjacent normal epithelium from the dysplasia tissue of the CIN2 sample of FIG. 17A. FIG. 17C-17D shows the representative image of the dysplasia epithelium of two CIN3 samples stained by IHC using the same anti-E6 monoclonal antibody. These data suggest the IHC staining by E6 monoclonal antibody is specific in the nuclear and cytoplasm of dysplasia cells.

Figure 18B:
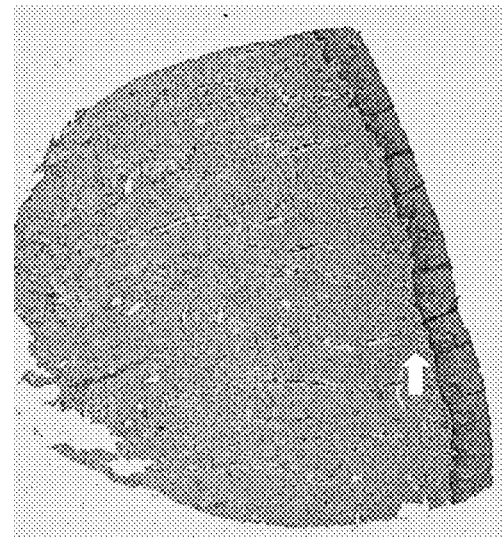
FIG. 18B shows the representative staining image of the normal epithelium (about 15 mm away from the tumor tissue) adjacent the SCC tissue of FIG. 18A.
Figure 18D:
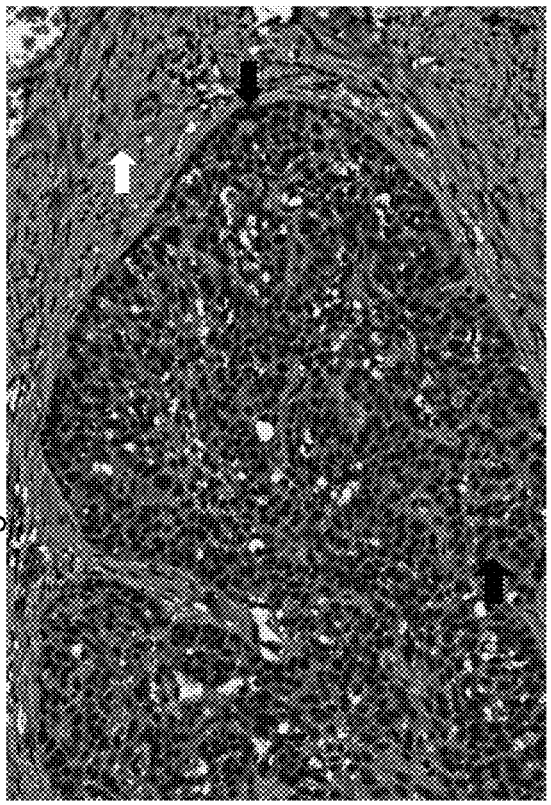
FIG. 18D shows the magnified representative image of the tumor cells from FIG. 18C to view the staining of the cytoplasm of the tumor cells.
Figure 18A:
FIG. 18A shows the representative staining image of the squamocarcinoma (SCC) tissue from tissue microarray using an anti-E7 monoclonal antibody in an immunohistocytostaining (IHC) assay.
Figure 18C:
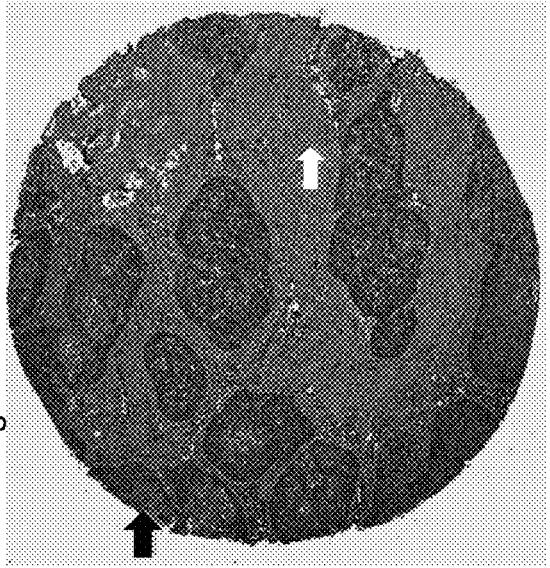
FIG. 18C shows the representative staining image of another SCC sample stained by the same anti-E7 monoclonal antibody as used in FIG. 18A in an IHC assay, demonstrating specific IHC staining in the tumor cells by the anti-E7 monoclonal antibody.

As an another example, FIGS. 18A-18D show IHC staining of squamous cell carcinoma demonstrated by mouse monoclonal HPV E7 antibody. Results indicate expression of E7 oncoprotein can be detected in the tumor cells of SCC tissue. Solid Black arrows indicate the specific staining of E7 protein in dysplasia cells, while empty clear arrows indicate the normal cells with no stain. Highly magnified images indicate localization of the E7 proteins expressed in the cytoplasm of tumor cells, but not in the normal epithelium, or stroma cells. These data suggest the IHC staining by E7 monoclonal antibody is specific in the cytoplasm of tumor cells. FIG. 18A shows the representative image of the squamocarcinoma (SCC) tissue from tissue microarray stained by IHC using an anti-E7 monoclonal antibody. FIG. 18B shows the representative image of the normal epithelium (15 mm away from the tumor tissue) of the SCC subject from FIG. 18A. FIG. 18C shows the representative image of another SCC sample from tissue microarray stained by IHC using the same anti-E7 monoclonal antibody. FIG. 18D shows the magnified representative image of the tumor cells stained in cytoplasm from FIG. 18C.

Figure 19C:
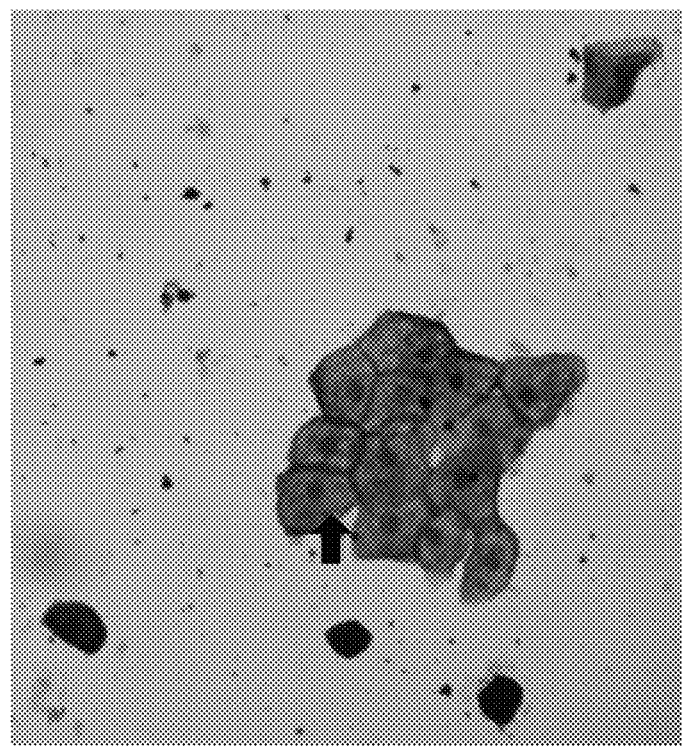
FIG. 19C shows the representative image of cervical cells from an adenocarcinoma (ADC) cervical scrape sample prepared by thin prep and stained by the same anti-E6 antibody shown in FIG. 19B in an ICC assay.
Figure 19B:
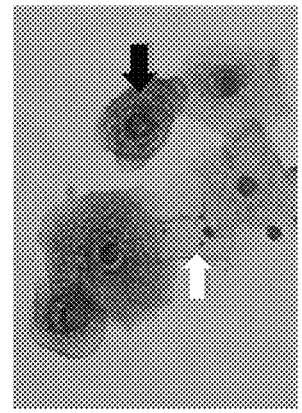
FIG. 19B shows the representative staining image of cervical cells from a CIN3 cervical scrape sample prepared by thin prep and stained by a mouse monoclonal anti-E6 antibody in an ICC assay.
Figure 19A:
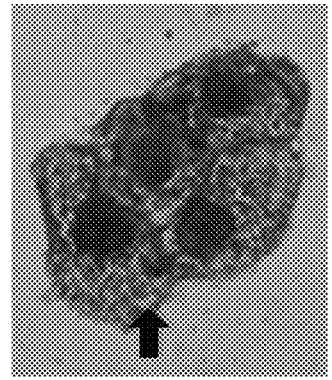
FIG. 19A shows the representative staining image of cervical cells from a CIN2 cervical scrape sample prepared by thin prep and stained by a mouse monoclonal anti-HPV E7 antibody in an immunocytochemistry (ICC) assay.

As an example, FIG. 19A-19C demonstrate immunocytochemistry assay using anti-HPV antibody. FIG. 19A shows the representative image of cervical cells from a CIN2 cervical scrape sample prepared by thin prep and stained by ICC using a mouse monoclonal anti-HPV E7 antibody. FIG. 19B shows the representative image of cervical cells from a CIN3 cervical scrape sample prepared by thin prep and stained by ICC using a mouse monoclonal anti-E6 antibody. FIG. 19C shows the representative image of cervical cells from an adenocarcinoma (ADC) cervical scrape sample prepared by thin prep and stained by ICC using the same anti-E6 antibody shown in FIG. 19B.

HPV Monoclonal Antibody Development:

Recombinant HPV E6, E7 or L1 proteins expressed in *E coli* was purified, concentrated, and dialyzed with PBS to be used as immunogen Immunization of mice was performed by following the standard procedure. Titer of serum was tested by ELISA followed by periodical boosting and bleeding. When the titer reaches optimal, fusion was done using standard procedure.

1). Hybridoma screening: To obtain hybridoma cell line producing HPV monoclonal antibody with specificity described in this invention, fusion clones were screened against not only the immunogen but also related or unrelated proteins as well. Two or more purified HPV recombinant proteins were used to screen against each hybridoma clones to obtain the specificity of each monoclonal antibody described herein.

As an example of hybridoma screening, a monoclonal antibody was obtained by screening antibody-producing hybridoma cells with two or more purified recombinant human papillomavirus proteins such that the monoclonal antibody is capable of reacting with the two or more purified recombinant human papillomavirus proteins. The two or more purified recombinant human papillomavirus proteins described herein consists of HPV 16 E6 protein, HPV 16 E7 protein, HPV 16 L1 protein, HPV 18 E6 protein, HPV18 E7 protein, HPV 18 L1 protein, and combinations thereof.

The two or more purified recombinant human papillomavirus viral proteins are HPV early proteins such that the monoclonal antibody is capable of reacting with the two or more human papillomavirus early proteins. For example, the selected hybridoma cell line produced a monoclonal antibody recognizing a common epitope on both HPV16 E6 and HPV16 E7 proteins. As another example, the selected hybridoma cell line produced a monoclonal antibody recognizing a common epitope on both HPV18 E6 and HPV18 E7 proteins.

As another example, the two or more purified recombinant human papillomavirus proteins comprise a purified recombinant human papillomavirus early protein and a purified recombinant human papillomavirus late protein such that the monoclonal antibody is capable of reacting with a common epitope on the purified recombinant human papillomavirus early protein and the purified recombinant human papillomavirus late protein. The purified recombinant human papillomavirus early protein consists of HPV 16 E6 protein, HPV 16 E7 protein, HPV 18 E6 protein, HPV18 E7 protein, and combinations thereof, and the purified recombinant human papillomavirus late protein consists of HPV 16 L1 protein, HPV 18 L1 protein, and combinations thereof.

For example, the selected hybridoma cell lines produced a monoclonal antibody recognizing a common epitope on HPV16 E6, HPV16 E7, and HPV16 L1 proteins or a common epitope on HPV16 E6 and HPV18 E6 proteins or a common epitope on HPV16 E7 and HPV18 E7 proteins or a common epitope on HPV16 E6, HPV16 E7, HPV16 L1, HPV18 E6, and HPV18 E7 proteins as described in the drawings of this invention.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types are selected from the group consisting of HPV 16, and HPV 18. The two or more different HPV types can also be selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof. As an example, the first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a specific epitope on only one of the first and the second purified recombinant human papillomavirus proteins and not the other purified recombinant human papillomavirus protein. The first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

2). Hybridoma cell line stocks: positive clones with desired reactivity on ELISA were selected and cloned down to single cell. Each single clone was then grown up by tissue culture. When the cell numbers reach millions of cell per ml, the cells were frozen down and kept at −80C or in liquid nitrogen as stock for each cell line.

3). Ascites production: each cell line was grown in tissue culture and injected to mice for ascites production. Ascites were collected and processed for Ig purification by protein G column Purified Ig from each cell line was isotyped and used for HPV immunoassays.

An object of the invention is to develop immune-responsive or antibody-reactive recombinant proteins derived from early genes and/or late genes of various HPV types and strains. It is a further object to provide these recombinant proteins in a chemically pure form. It is a still further object to provide simple, rapid, less expensive and more sensitive assays/tests for diagnosing not only HPV infection, but also most, if not all, HPV-associated neoplasm.

Cloning and production of recombinant proteins encoded by HPV genes: Recombinant proteins encoded by early HPV genes and late HPV genes are obtained. Recombinant proteins can be obtained by itself or as hybrid proteins fused transcriptionally or translational to a portion of a full length DNA fragment for a HPV gene of interest. The DNA sequence of the HPV gene of interest may be derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6: GI:9627356; HPV51-E6: GI:9627155; HPV52-E6: GI:9627370; HPV56-E6: GI:9627383; HPV59-E6:

GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Cloning and production of various recombinant proteins encoded by HPV-16, early E6 gene: Cloning of an exemplary oncogenic E6 early gene from an exemplary HPV type, HPV-16, is described herein. A 474 base pair (b.p.) DNA fragment (SEQ ID NO. 1) containing the 157 amino acid coding region (SEQ ID NO. 2) of the HPV-16 E6 gene was obtained by polymerase chain reaction (PCR) amplification. Primers were used for cloning, for example, a pair of forward and reverse primers, 5' cgcGGATCCcaccaaaagagaactgcaatgtttc 3' (SEQ ID NO. 3) and 5' cccAAGCTTttacagctgggtttctctacgtg 3' (SEQ ID NO. 4), respectively. The DNA sequence of the isolated DNA fragment was confirmed by comparing with the sequence from Gene Bank database. All cloning procedures are carried out according to the protocols described in "Molecular Cloning", A Laboratory Manual, eds. Sambrook, Fritsch and Maniatis, Cold Spring Harbor Laboratory Press, 1989. In addition, E6 DNA fragments from different strains of HPV-16 can also be cloned from different clinical samples or sources.

The obtained 474 base pair (b.p.) DNA fragment was subcloned into a histidine tag expression vector, pQE30, in order to express a his-tagged recombinant HPV-16 E6 protein. The resulting plasmid DNA is designated, pQE30/HPV16-E6 for the expression of His-tagged-HPV 16-E6 recombinant protein. The DNA sequence and the amino acid sequences of the resulting his-tagged recombinant HPV-16 E6 protein are shown as SEQ ID NO. 5 (a 510 base pair (b.p.) DNA fragment) and SEQ ID NO. 6 (a 169 amino acid fusion protein), respectively.

Cloning and production of recombinant proteins encoded by HPV-16 early E7 gene: Cloning of an exemplary oncogenic E7 early gene from an exemplary HPV type, HPV-16, is described herein. A 294 base pair (b.p.) DNA fragment (SEQ ID NO. 7) containing the 99 amino acid coding region (SEQ ID NO. 8) of the HPV-16 E7 gene was obtained by polymerase chain reaction (PCR) amplification. Primers were used for cloning, for example, a pair of forward and reverse primers, 5' cgcGGATCCcatggagatacacctacattgc 3' (SEQ ID NO. 9) and 5' ccgGAATTCtttatggtttctgagaacagatgg 3' (SEQ ID NO. 10), respectively. The DNA sequence of the isolated DNA fragment was confirmed by comparing with the sequence from Gene Bank database. In addition, E7 DNA fragments from different strains of HPV-16 can also be cloned from different clinical samples or sources.

The obtained 294 base pair (b.p.) DNA fragment was subcloned into a GST expression vector in order to express a recombinant HPV-16 E7 GST fusion protein. The DNA sequence and the amino acid sequences of the resulting recombinant HPV-16 E7 GST protein are shown as SEQ ID NO. 11 (a 972 base pair (b.p.) DNA fragment) and SEQ ID NO. 6 (a 323 amino acid fusion protein), respectively. The molecular weight of the resulting recombinant HPV-16 E7 GST protein is about 37.2 KD. The recombinant HPV-16 E7 GST proteins were obtained and purified to a final concentration of about 1 mg/L. Other expression systems can also be used to express E7 recombinant proteins from various HPV types and strains. Recombinant E7 fusion proteins or recombinant E7 baculovirus proteins were used to detect the presence of E7 antibody on clinical samples and were also be used as immunogens for production of polyclonal antiserum and monoclonal antibodies.

What is claimed is:

1. A method for quantifying an HPV protein expressed by a human papillomavirus (HPV) infected cell in a clinical sample, comprising the steps of:
    receiving a clinical sample, said clinical sample comprising a population of cells susceptible to infection by an HPV protein, wherein
        the population of cells are whole-cells;
    depositing said clinical sample onto a substrate without lysing said population of cells;
    contacting said clinical sample with a solution comprising a monoclonal antibody that specifically binds to the HPV protein in situ under conditions that promote specific binding of said monoclonal antibody to the HPV protein expressed by one or more cells in said population of cells from said obtained clinical sample, wherein
        the monoclonal antibody specifically binds to two or more native HPV proteins from different HPV types, wherein
            the two or more native HPV proteins are native E7 proteins from different HPV types or native E6 proteins from different HPV types, and
            the monoclonal antibody is capable of binding in situ to said proteins in a clinical sample;
    determining, in a solution phase, the amount of said monoclonal antibody bound to said clinical sample; and
    quantifying the HPV protein in said clinical sample using the amount of said monoclonal antibody bound to said clinical sample.

2. The method of claim 1, wherein said clinical sample comprises cells dispersed in a collection liquid.

3. The method of claim 1, further comprising measuring a cell density of said clinical sample.

4. The method of claim 3, further comprising normalizing the cell density of said clinical sample.

5. The method of claim 1, wherein said substrate is selected from the group consisting of a membrane, a bead, and a microtiter well surface.

6. The method of claim 1, further comprising comparing said quantified HPV protein to a predetermined HPV protein expression level threshold.

7. The method of claim 1, further comprising normalizing said quantified HPV protein according to the number of cells present in said clinical sample.

8. The method of claim 1, further comprising comparing said quantified HPV protein to an HPV protein standard curve.

9. The method of claim 2, wherein
    said clinical sample comprises fixed cells; and
    said collection liquid comprises fixative agents.

10. The method of claim 2, wherein said cells are obtained from a cervical swab or a cervical scrape.

11. The method of claim 2, wherein said cells are obtained from an oral swab, an oral scrape, an anal swab, or an anal scrape.

12. The method of claim 1, wherein said HPV protein comprises an HPV protein selected from the group consisting of one or more HPV E6 proteins, one or more HPV E7 proteins and combination thereof.

13. The method of claim 1, wherein said substrate is a microtiter well surface.

14. The method of claim 1, wherein the determining step further comprises contacting, in the solution phase, the monoclonal antibody bound to said clinical sample with a secondary antibody comprising a label that specifically binds to said monoclonal antibody.

15. The method of claim 14, wherein said label is selected from the group consisting of a direct label and an indirect label.

16. The method of claim 1, wherein said monoclonal antibody comprises a label.

17. The method of claim 16, wherein said label is selected from the group consisting of a direct label and an indirect label.

18. The method of claim 1, wherein the monoclonal antibody comprises an enzymatic label, and said determining step comprises quantifying, in a solution phase, a chromogenic substrate produced by the enzymatic label.

19. The method of claim 1, wherein the monoclonal antibody comprises a fluorescent label, and said determining step comprises quantifying, in a solution phase, a fluorescence signal.

20. The method of claim 1, further comprising assessing risk of an HPV-related precancer of cancer disease grade in said clinical sample based on said quantified HPV protein.

21. The method of claim 20, wherein said HPV-related cancer is cervical cancer.

22. The method of claim 15, wherein the secondary antibody comprises an enzymatic label, and said determining step comprises quantifying, in a solution phase, a chromogenic substrate produced by the enzymatic label.

23. The method of claim 1, wherein the method for quantifying an HPV protein expressed by an HPV infected cell in a clinical sample, comprising the steps of:

receiving a liquid-based cervical swab clinical sample, wherein the clinical sample comprising a population of whole-cells susceptible to infection by a HPV;

measuring a cell density of the clinical sample;

normalizing the cell density in the clinical sample;

depositing said clinical sample onto a microtiter well surface without lysing the population of cells;

contacting, in a solution phase, the biotinylated monoclonal antibody with a solution comprising an enzymatic molecule, contacting, in a solution phase, the enzymatic molecule with a solution comprising a substrate molecule that reacts with the enzymatic molecule to produce a chromogenic product;

determining, in a solution phase, the amount of the chromogenic product;

quantifying the HPV protein in the clinical sample using the amount of the chromogenic product determined in the solution;

normalizing the quantified HPV protein according to the number of cells present in the clinical sample;

comparing the quantified HPV protein to a predetermined HPV protein expression level threshold assessing risk of an HPV-related precancer or cancer disease grade in the clinical sample based on the quantified HPV protein.

* * * * *